(12) United States Patent
Grimaldi et al.

(10) Patent No.: US 9,611,245 B2
(45) Date of Patent: Apr. 4, 2017

(54) DIARYLALKYLAMINE REV-ERB ANTAGONISTS AND THEIR USE AS MEDICAMENTS

(71) Applicant: FONDAZIONE ISTITUTO ITALIANO DI TECNOLOGIA, Genoa (IT)

(72) Inventors: Benedetto Grimaldi, Genoa (IT); Esther Torrente, Genoa (IT); Rita Scarpelli, Genoa (IT); Giovanni Bottegoni, Genoa (IT); Tiziano Bandiera, Genoa (IT); Marina Veronesi, Genoa (IT)

(73) Assignee: Fondazione Istituto Italiano Di Tecnologia, Genoa (IT)

( * ) Notice: Subject to any disclaimer, the term of this patent is extended or adjusted under 35 U.S.C. 154(b) by 3 days.

(21) Appl. No.: 15/027,951

(22) PCT Filed: Oct. 9, 2014

(86) PCT No.: PCT/EP2014/071654
§ 371 (c)(1),
(2) Date: Apr. 7, 2016

(87) PCT Pub. No.: WO2015/052283
PCT Pub. Date: Apr. 16, 2015

(65) Prior Publication Data
US 2016/0237057 A1    Aug. 18, 2016

(30) Foreign Application Priority Data
Oct. 9, 2013 (IT) .............................. TO2013A0816

(51) Int. Cl.
| C07D 333/20 | (2006.01) |
| C07D 309/14 | (2006.01) |
| C07D 211/58 | (2006.01) |
| C07D 295/08 | (2006.01) |
| C07D 295/16 | (2006.01) |

(52) U.S. Cl.
CPC .......... *C07D 333/20* (2013.01); *C07D 211/58* (2013.01); *C07D 295/08* (2013.01); *C07D 295/16* (2013.01); *C07D 309/14* (2013.01)

(58) Field of Classification Search
CPC .. C07D 333/20; C07D 295/08; C07D 295/16; C07D 211/58
See application file for complete search history.

(56) References Cited

FOREIGN PATENT DOCUMENTS

| WO | WO 2007/065261 A1 | 6/2007 |
| WO | WO 2013/033310 A1 | 3/2013 |
| WO | WO 2013/045519 A1 | 4/2013 |

OTHER PUBLICATIONS

Compound CAS RN 1385962-20-8, Ukrorgsyntez Ltd, Aug. 3, 2012.*
International Search Report and Written Opinion, mailed Dec. 5, 2014, for PCTAN PCT/EP2014/071654, 12 pages.
Kojetin et al., "Identification of SR8278 a Synthetic Antagonist of the Nuclear Heme Receptor REV-ERB," *ACS Chem. Biol.* 6: 131-134, 2011.
Anzulovich et al., "*Elovl3*: a model gene to dissect homeostatic links between the circadian clock and nutritional status," *Journal of Lipid Research* 47: 2690-2700, 2006.
Borgs et al "Cell 'circadian' cycle," *Cell Cycle* 8(6): 832-837, Mar. 15, 2009.
Burke et al., "Transcriptional repression by the orphan steroid receptor RVR/Rev-erbβ is dependent on the signature motif and helix 5 in the E region: functional evidence for a biological role of RVR in myogenesis," *Nucleic Acids Research* 24(18): 3481-3489, 1996.
Chini et al., "DBC1 (Deleted in Breast Cancer 1) modulates the stability and function of the nuclear receptor Rev-erbα," *Biochem J.* 451: 453-461, 2013.
Cho et al., "Regulation of circadian behaviour and metabolism by REV-ERB-α and REV-ERB-β," *Nature* 485: 123-127, May 3, 2012.
Erren et al., "Schichtarbeit and Krebs," *Deutsches Ärzteblatt* 107(38): 657-662, Sep. 24, 2010, 8 pages.
Gibbs et al., "The nuclear receptor REV-ERBα mediates circadian regulation of innate immunity through selective regulation of inflammatory cytokines," *PNAS* 109(2): 582-587, Jan. 10, 2012.
Grimaldi et al., "PER2 Controls Lipid Metabolism by Direct Regulation of PPARγ," *Cell Metab.* 12(5): 509-520, Nov. 3, 2010.
Harding et al., "The Orphan Receptor Rev-ErbAα Activates Transcription via a Novel Response Element," *Molecular and Cellular Biology* 13(5): 3113-3121, May 1993.
Kourtidis et al., "An RNA Interference Screen Identifies Metabolic Regulators *NR1D1* and *PBP* as Novel Survival Factors for Breast Cancer Cells with *ERBB2* Signature," *Cancer Res.* 70(5): 1783-1792, 2010.
Mormont et al., "Circadian-System Alterations During Cancer Processes: A Review," *Int. J Cancer* 70: 241-247, 1997.

(Continued)

*Primary Examiner* — Yong Chu
(74) *Attorney, Agent, or Firm* — Seed IP Law Group LLP

(57) ABSTRACT

The present invention relates to compounds of Formula (I) or pharmaceutically acceptable salts or solvates thereof: It further discloses a pharmaceutical composition comprising the compounds of Formula (I) and their uses as antiproliferative and pro-apoptotic agents for cancer therapy.

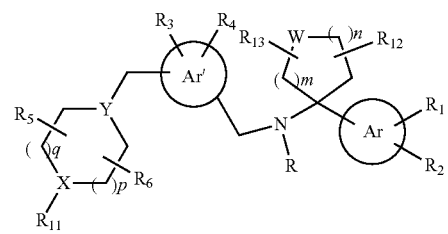

11 Claims, 1 Drawing Sheet

(56) References Cited

OTHER PUBLICATIONS

Mormont et al., "Cancer Chronotherapy: Principles, Applications, and Perspectives," *Cancer* 97: 155-169, 2003.
Ozturk et al., "Loss of cryptochrome reduces cancer risk in *p53* mutant mice," *PNAS* 106(8): 2841-2846, Feb. 24, 2009.
Phelan et al., "Structural Analysis of Rev-erbα Bound to NCoR Reveals a Unique Mechanism of Nuclear Receptor-Corepressor Interaction," *Nat. Struct. Mol. Biol.* 17(7): 808-814, Jul. 2010.
Ripperger et al., "REV-ERB-erating nuclear receptor functions in circadian metabolism and physiology," *Cell Research* 22: 1319-1321, 2012.
Solt et al., "Regulation of circadian behaviour and metabolism by synthetic REV-ERB agonists," *Nature* 485: 62-68, May 3, 2012.
Teboul et al., "How nuclear receptors tell time," *J. Appl. Physiol.* 107: 1965-1971, 2009.
Trauernicht et al., "DBC-1 mediates endocrine resistant breast cancer cell survival," *Cell Cycle* 9(6): 1218-1219, Mar. 15, 2010.
Trump et al., "Optimized Chemical Probes for REV-ERBα," *J. Med. Chem.* 56(11): 4729-4737, Jun. 13, 2013.
Wang et al., "The Orphan Nuclear Receptor Rev-erbα Regulates Circadian Expression of Plasminogen Activator Inhibitor Type 1," *The Journal of Biological Chemistry* 281(45): 33842-33848, Nov. 10, 2006.
Content et al., "Optimization of the Manufacturing Route to PF-610355 (1): Synthesis of Intermediate 5," *Org. Process Res. Dev.* 17: 193-201, 2013.
De Koning et al., "Development of a Potential Manufacturing Route to PF-00610355: A Novel Inhaled $\beta_2$-Adrenoreceptor Agonist," *Org. Process Res. Dev.* 15: 1256-1265, 2011.
Ellman et al., "N-*tert*-Butanesulfinyl Imines: Versatile Intermediates for the Asymmetric Synthesis of Amines," *Acc. Chem. Res.* 35: 984-995, 2002.
Grant et al., "GSK4112, a Small Molecule Chemical Probe for the Cell Biology of the Nuclear Heme Receptor Rev-erbα," *ACS Chem. Biol.* 5(10): 925-932, 2010.
Kojetin et al., "A Role for Rev-erbα Ligands in the Regulation of Adipogenesis," *Curr. Pharm. Des.* 17: 1-4, 2011.
McMahon et al., "Highly Stereoselective Addition of Organometallic Reagents to N-*tert*-Butanesulfinyl Imines Derived from 3- and 4-Substituted Cyclohexanones," *Org. Lett.* 6(10): 1645-1647, 2004.
Paschos et al., "The Role of Clock Genes in Pharmacology," *Annu. Rev. Pharmacol. Toxicol.* 50: 187-214, 2010.
Sahar et al., "Circadian Clock and Breast Cancer," *Cell Cycle* 6(11): 1329-1331, 2007.

\* cited by examiner

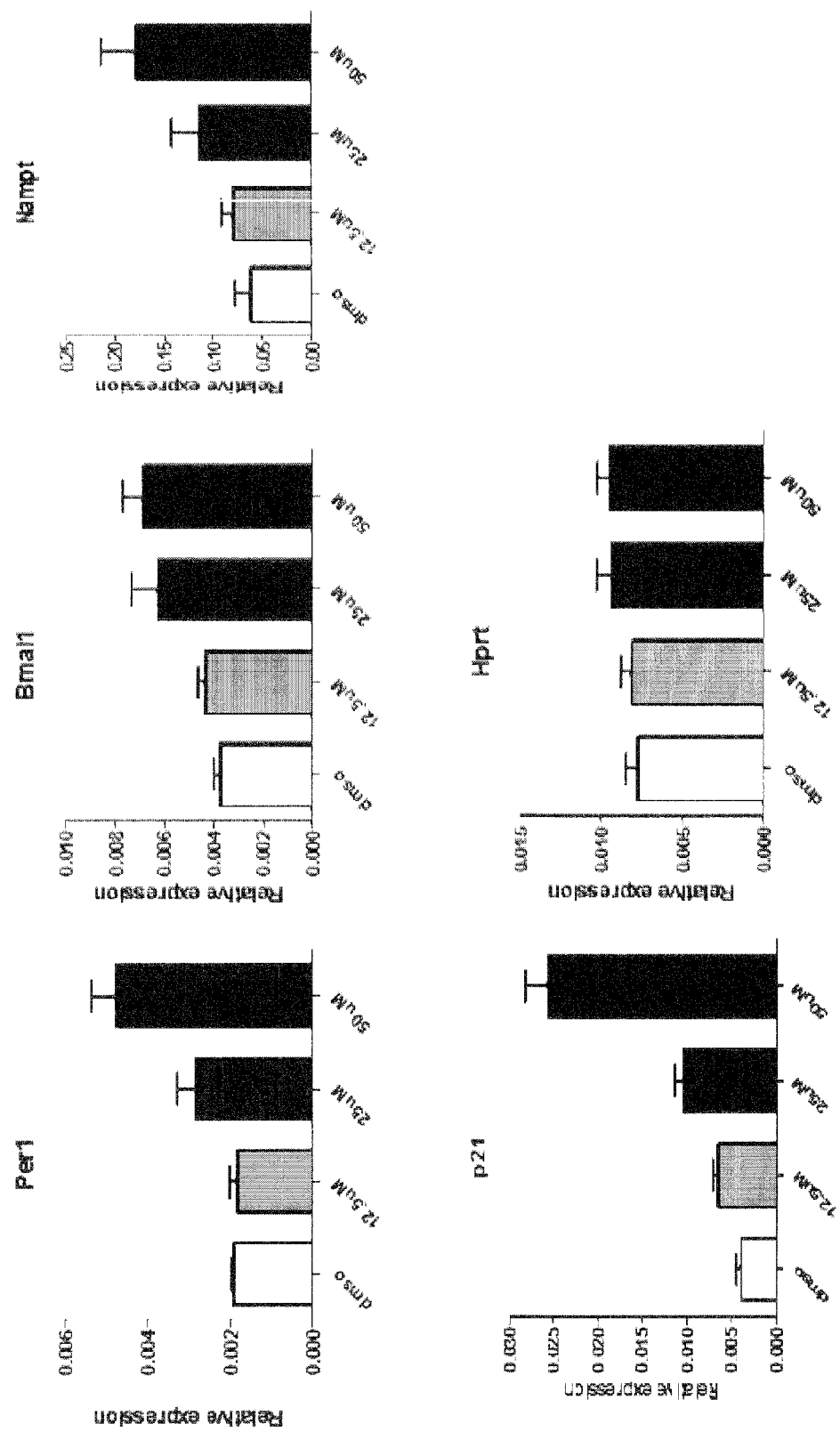

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Primer sequence

<400> SEQUENCE: 1
cagtgctcct gttcctgcat c         21

<210> SEQ ID NO 2
<211> LENGTH: 19
<212> TYPE: DNA
<213> ORGANISM: Artificial Sequence
<220> FEATURE:
<223> OTHER INFORMATION: Primer sequence

<400> SEQUENCE: 2
cccgccaact gcagaatct           19

<210> SEQ ID NO 3
<211> LENGTH: 20
<212> TYPE: DNA
<213> ORGANISM: Artificial Sequence
<220> FEATURE:
<223> OTHER INFORMATION: Primer sequence

<400> SEQUENCE: 3
ccagaggccc ctaactcctc          20

<210> SEQ ID NO 4
<211> LENGTH: 21
<212> TYPE: DNA
<213> ORGANISM: Artificial Sequence

```
<220> FEATURE:
<223> OTHER INFORMATION: Primer sequence

<400> SEQUENCE: 4
tggtctgcca ttggatgatc t                                              21

<210> SEQ ID NO 5
<211> LENGTH: 20
<212> TYPE: DNA
<213> ORGANISM: Artificial Sequence
<220> FEATURE:
<223> OTHER INFORMATION: Primer sequence

<400> SEQUENCE: 5
gagttcaaca tcctcctggc                                                20

<210> SEQ ID NO 6
<211> LENGTH: 20
<212> TYPE: DNA
<213> ORGANISM: Artificial Sequence
<220> FEATURE:
<223> OTHER INFORMATION: Primer sequence

<400> SEQUENCE: 6
tcacggcatt caaagtagga                                                20

<210> SEQ ID NO 7
<211> LENGTH: 20
<212> TYPE: DNA
<213> ORGANISM: Artificial Sequence
<220> FEATURE:
<223> OTHER INFORMATION: Primer sequence

<400> SEQUENCE: 7
aaggtgaagg tcggagtcaa                                                20

<210> SEQ ID NO 8
<211> LENGTH: 20
<212> TYPE: DNA
<213> ORGANISM: Artificial Sequence
<220> FEATURE:
<223> OTHER INFORMATION: Primer sequence

<400> SEQUENCE: 8
aatgaagggg tcattgatgg                                                20

<210> SEQ ID NO 9
<211> LENGTH: 17
<212> TYPE: DNA
<213> ORGANISM: QArtificial Sequence
<220> FEATURE:
<223> OTHER INFORMATION: Primer sequence

<400> SEQUENCE: 9
gttatggcga cccgcag                                                   17

<210> SEQ ID NO 10
<211> LENGTH: 20
<212> TYPE: DNA
<213> ORGANISM: Artificial Sequence
<220> FEATURE:
<223> OTHER INFORMATION: Primer sequence

<400> SEQUENCE: 10 acccttttcca aatcctcagc                                               20
```

```
<210> SEQ ID NO 11
<211> LENGTH: 20
<212> TYPE: DNA
<213> ORGANISM: Artificial Sequence
<220> FEATURE:
<223> OTHER INFORMATION: Primer sequence

<400> SEQUENCE: 11
agtcagttcc ttgtggagcc                                                 20

<210> SEQ ID NO 12
<211> LENGTH: 19
<212> TYPE: DNA
<213> ORGANISM: Artificial Sequence
<220> FEATURE:
<223> OTHER INFORMATION: Primer sequence

<400> SEQUENCE: 12
catgggttct gacggacat                                                  19

<210> SEQ ID NO 13
<211> LENGTH: 13
<212> TYPE: DNA
<213> ORGANISM: Artificial Sequence
<220> FEATURE:
<223> OTHER INFORMATION: RevRE consensus

<400> SEQUENCE: 13
agaatgtagg tca                                                        13

<210> SEQ ID NO 14
<211> LENGTH: 14
<212> TYPE: DNA
<213> ORGANISM: Artificial Sequence
<220> FEATURE:
<223> OTHER INFORMATION: mutated version of the RevRE sequence

<400> SEQUENCE: 14
gagcccgtag gtca                                                       14
```

DIARYLALKYLAMINE REV-ERB ANTAGONISTS AND THEIR USE AS MEDICAMENTS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 350050_402USPC_SEQUENCE_LISTING.txt. The text file is 3 KB, was created on Apr. 6, 2016, and is being submitted electronically via EFS-Web.

TECHNICAL FIELD

The present invention relates to novel diarylalkylamine compounds and their use as anti-proliferative and pro-apoptotic agents for cancer therapy.

BACKGROUND ART

Progress in the circadian rhythm field suggests that many key physiological mechanisms are remarkably dependent on the biological clock. It has also become clear that a number of diseases with important unmet medical need display marked circadian variation in their symptoms and severity. Indeed, abnormal functioning of the clock results in severe dysfunctions and pathologies, including cancer. As an example, the circadian organization tends to be lost and possibly replaced with an ultradian periodicity in rapidly growing or advanced stage tumors (Mormont et al., Int. J. Cancer, 1997; 70: 241-247).

Recent developments in our understanding of circadian biology also indicate that time and duration of dosing may have profound consequences for the efficacy and safety of new and existing therapeutic agents. Indeed, an increasing number of drugs show a circadian-dependency of their pharmacodynamics (Paschos et al., Annu. Rev. Pharmacol. Toxicol., 2010; 50: 187-214).

Circadian dosing time appears to influence the extent of toxicity of numerous anticancer drugs, including cytostatics and cytokines, in mice or rats (Paschos et al., Annu. Rev. Pharmacol. Toxicol., 2010; 50: 187-214). For all these drugs, the survival rates are reported to vary by 50% according to a circadian dosing time of a potentially lethal dose. Such a large difference is observed irrespective of injection route—(intravenous or intraperitoneal) or the number of injections (single or repeated)—(Mormont et al., Cancer, 2003; 97: 155-169).

A remarkable observation reveals that risk for breast cancer is significantly higher in industrialized societies, and the risk increases as developing countries become more westernized (Sahar et al., Cell Cycle, 2007; 6: 1329-1331). Incidence of breast cancer increases significantly in women working nightshifts, being higher among individuals who spent more years and hours per week working at night. From a clinical point of view, prognosis of cancer is poorer in patients with altered circadian rhythm compared to patients with normal rhythm (Sahar et al., Cell Cycle, 2007; 6: 1329-1331).

In 2007, the International Agency for Research on Cancer (IARC) classified shift work with circadian disruption or chronodisruption as a probable human carcinogen (Erren et al., Dtsch. Arztebl. Int., 2010; 107: 657-662). Interestingly, disruption of circadian endocrine rhythms, either by pinealectomy or through constant light exposure, increases the formation of spontaneous mammary tumors in rodents (Sahar et al., Cell Cycle, 2007; 6: 1329-1331).

Breast cancer is the second most common type of cancer after lung cancer worldwide and the fifth most common cause of cancer death. It is found more in women as compared to men. Worldwide more than one million new cases of breast cancer are diagnosed every year. New breast cancer cases are mostly found in North America. Breast cancer is usually found in women over the age of 40 years. Breast cancer cases have risen about 30% in the past 25 years in western countries like the US and Europe.

Although a continuous perturbation of the circadian rhythm has been proposed as a probable human carcinogen, a surprising observation showed that some alteration of the circadian clock may include beneficial effects. As an example, in mice bearing a deletion of the tumor suppressor p53 the genetic ablation of the two circadian regulators CRY1 and CRY2 decreased the development of tumors and increased the survival of the animals (Ozturk et al., Proc. Natl. Acad. Sci. U.S.A, 2009; 106: 2841-2846).

Taken collectively, these observations open up the possibility to identify novel pharmacological targets for cancer treatment among the molecular factors involved in the circadian regulation.

A decade ago, the REV-ERB/NR1D subgroup receptors, REV-ERBα (NR1D1) and REV-ERBβ (NR1D2), was identified as an integral component of the circadian clock machinery (Teboul et al., J. Appl. Physiol., 2009; 107: 1965-1971; Ripperger et al., Cell Res., 2012; 22:1319-1321). Both REV-ERBs receptors lack the classical nuclear receptor AF-2 trans-activating domain and represses gene activity by associating with a co-repressor complex (Ripperger et al., Cell Res., 2012; 22:1319-1321; Phelan et al., Nat. Struct. Mol. Biol., 2010; 17: 808-814).

In the presence of the natural ligand (heme), REV-ERB/co-repressor complex interaction is enhanced and the transcriptional repression of target genes is achieved (Ripperger et al., Cell Res., 2012; 22:1319-1321). The selection of the targets is obtained by the binding of the DNA binding domain of REV-ERBs with specific cis-elements within the promoter of the genes.

Being historically first discovered, the biological function of REV-ERBα has been the most characterized. Indeed, REV-ERBα has been implicated in the regulation of several processes, including circadian rhythm, adipogenesis, inflammation (Phelan et al., Nat. Struct. Mol. Biol., 2010; 17: 808-814).

At the molecular level, several genes, which activity is regulated by REV-ERBα, have been reported (Phelan et al., Nat. Struct. Mol. Biol., 2010; 17: 808-814). Notably, in addition to genes involved in the above mentioned processes, REV-ERBα regulated targets also include important cell cycle regulatory genes, such as the Cyclin-dependent kinase inhibitor p21 (Cink1a/p21) (Burke et al., Nucleic Acids Research, 1996; 24: 3481-3489; Borgs et al., Cell Cycle, 2009; 8: 832-837).

REV-ERBα has been also reported to repress the transcription of genes such as Elovl3 (a very long-chain fatty acid elongase) (Anzulovich et al., J. Lipid Res., 2006; 47: 2690-2700) and PAI-1 (Plasminogen Activator Inhibitor 1, a regulator of the fibrinolytic system and modulator of inflammation, atherothrombosis and atherosclerosis) (Wang et al., J. Biol. Chem., 2006; 281: 33842-33848). Because several responses mediated by REV-ERBα feel the influence of the circadian rhythm, it has been postulated that REV-ERBα activity may have the potential to contribute to—or even to control—the crosstalk between circadian and many other physiological processes.

However, due to the modest clock phenotypes of REV-ERBα-deficient mice, REV-ERBα has been proposed to confer robustness to the oscillatory clock rather than being a pacemaker component essential for rhythm generation, such as other circadian regulators (i.e., Bmal1) (Teboul et al., J. Appl. Physiol., 2009; 107: 1965-1971). This view has been recently challenged by a recent publication that strongly supports a much more prominent role of REV-ERBs receptors in the core clock mechanism than anticipated (Cho et al., Nature, 2012; 485: 123-127). In fact, the comparative analysis of genome sequences on which REV-ERBα and REV-ERBβ are recruited revealed an extensive overlap between the cistromes of the two receptors (Cho et al., Nature, 2012; 485: 123-127). This result suggests that REV-ERBα and REV-ERBβ isoforms can compensate each other for the repression of several target genes, including several members of the circadian regulators.

In line with this observation, the generation of liver-specific REV-ERBα/REV-ERBβ double-knockout mice (L-DKO) demonstrated that 90% of the approximately 900 genes rhythmically expressed in the liver of wild-type animals became arrhythmic in the liver of the L-DKO mice (Cho et al., Nature, 2012; 485: 123-127).

Nevertheless, some biological responses may depend on the activity of a specific REV-ERBs isoform. Indeed, genetic ablation of REV-ERBα or genetic knockdown of REV-ERBα expression have been reported to modulate the production and release of the proinflammatory cytokine IL-6 (Gibbs et al., Proc. Natl. Acad. Sci. U.S.A, 2012; 109: 582-587).

A role of REV-ERBα as a survival factor for breast cancer cells with the ErbB2 signature has been also reported (Kourtidis et al., Cancer Research, 2010; 70: 1783-1792). The proto-oncogene ErbB2 (Her2) is overexpressed in about the 30% of breast carcinoma (ErbB2 positive breast tumors). REV-ERBα has been reported to be co-overexpressed with ErbB2, suggesting that this gene may represent novel factor influencing ErbB2-positive tumors. More importantly, the genetic inhibition of REV-ERBα was able to block the proliferation of ErbB2 positive breast cancer cells (Kourtidis et al., Cancer Research, 2010; 70: 1783-1792).

Notably, it has been recently reported that the protein DBC1 (Deleted in Breast Cancer 1) modulates the stability and function of REV-ERBα (Chini et al., The Biochemical Journal, 2013; 451: 453-461). DBC1 was originally identified during a genetic search for candidate breast tumor suppressor genes on a human chromosome 8p21 region frequently deleted in breast cancers (Trauernicht et al., Cell Cycle, 2010; 9: 1218-1219). However, further analyses revealed that DBC1 expression is not substantially lost in cancers from any source. In fact, DBC1 has been found to be upregulated in breast carcinoma versus normal breast tissue and in breast ductal carcinoma versus other cancers (Trauernicht et al., Cell Cycle, 2010; 9: 1218-1219). The fact that DBC1 enhances REV-ERBα protein stability (Chini et al., The Biochemical Journal, 2013; 451: 453-461) reveals an interesting molecular connection between DBC1 and REV-ERBα overexpressing breast tumors.

Although the molecular mechanism of REV-ERBα mediated growth inhibition of ErbB2-positive breast cancer cells has not deeply been investigated yet, biological data (Kourtidis et al., Cancer Research, 2010; 70: 1783-1792) support the idea that a pharmacological repression of REV-ERBα activity may be used for breast cancer therapy.

In addition, considering that REV-ERBα and REV-ERBβ showed a co-recruitment on the promoters of several genes involved in cell cycle regulation, including p21 (Borgs et al., Cell Cycle, 2009; 8: 832-837; Cho et al., Nature, 2012; 485: 123-127), the co-repression of both REV-ERBs isoforms may even have more pronounced effects on the proliferation and viability of cancer cells.

The first REV-ERBα ligand, the agonist tertiary amine GSK4112, has been recently identified (Grant et al., ACS Chemical Biology, 2010; 5: 925-932). GSK4112 was identified in a FRET assay as capable to dose-dependently increase the interaction of a peptide derived from NCoR (Nuclear receptor Co-Repressor) with REV-ERBα (Grant et al., ACS Chemical Biology, 2010; 5: 925-932). The treatment with GSK4112 decreases BrnaH expression in cell culture in a dose-dependent manner and induces adipogenesis in 3T3-L1 cells as demonstrated by lipid accumulation and increased expression of key adipogenic genes (Kojetin et al., Current Pharm. Design, 2011; 17: 320-324). GSK4112 behaves therefore as a REV-ERBα agonist, regulating the expression of REV-ERBα responsive target genes in a manner similar to the physiological ligand, heme (Ripperger et al., Cell Res., 2012; 22:1319-1321).

The ligand binding domain (LBD) of REV-ERB shares a high homology degree with the REV-ERBβ LBD. Indeed, GSK4112 has been reported to act on both isoforms (Solt et al., Nature, 2012; 485: 62-68). GSK4112 displays poor pharmacokinetic properties because of high clearance and rapid metabolism that decrease its bioavailability. (Solt et al., Nature, 2012; 485: 62-68).

REV-ERB ligands, such as the REV-ERB agonists SR9009, SR9011 and analogs, are known from WO 2013/033310. They are closely related to GSK4112 by sharing a common tertiary amine scaffold and two out of the three substituents at the amine nitrogen, and they are disclosed as useful treatments of malconditions such as diabetes, obesity, atherosclerosis, dyslipidemia and coronary artery disease.

Compounds SR9009 and SR9011 have been tested in mice for their possibility to induce metabolic responses (Solt et al., Nature, 2012; 485: 62-68). These compounds, in addition to influence the circadian clock, were also able to improve the metabolic parameters of diet-induced obese mice. The changes measured on biochemical parameters were also associated to a modified gene expression profile in metabolic tissues such as liver, skeletal muscle and adipose tissue. However, the use of SR9009 and SR9011 to interrogate REV-ERBα biology is complicated by high metabolic clearance rates that necessitate high dosing to achieve meaningful levels of exposure in vivo (Solt et al., Nature, 2012; 485: 62-68). Furthermore, the unfavorable DMPK (Drug Metabolism and Pharmacokinetic) profile of GSK4112, SR9009 and SR9011 renders these compounds unsuitable as truly effective remedies for the clinical treatment of diseases and pathologies associated to the unbalance of the circadian clock.

In addition, the tertiary amines mentioned above have known activity on the nuclear receptor LXRα, a potential liability for interpretation of results from cell-based and animal pharmacology (Trump et al., J. Med. Chem., 2013; 56: 4729-4737). Indeed, further studies demonstrated that GSK4112 also agonizes LXRα. Notably, SR9009 and SR9011 resulted 100 times more active toward LXRα than REV-ERBs (Trump et al., J. Med. Chem., 2013; 56: 4729-4737). Novel triarylmethylamines related to GSK4112, SR9009 and SR9011 and showing high REV-ERBα agonist potency, selectivity, and bioavailability have been reported (Trump et al., J. Med. Chem., 2013; 56: 4729-4737). Notably, these GSK4112 analogues displayed a much lower effect than GSK4112 on the reduction of LPS-mediated IL-6 transcriptional activation.

WO 2013/045519 claims certain substituted triazolopyridazines as REV-ERB agonists useful for treating any disease wherein the activation of REV-ERB has therapeutic effects, for instance in inflammatory and circadian rhythm-related disorders or cardiometabolic diseases.

Finally, certain dibenzylamine derivatives are claimed in WO 2007/065261 as inhibitors of PAI-1 and, as such, claimed to be therapeutically useful, mainly, in several cardiovascular diseases and noninsulin dependent diabetes mellitus.

The only reported REV-ERBα antagonist described in the literature is the 1,2,3,4 tetrahydroisoquinoline derivative SR8278 which, differently from GSK4112, features an amidic nitrogen as the core element, thus shifting away from basic compounds (Kojetin et al., ACS Chem. Biol., 2011; 6: 131-134). SR8278 is described as a REV-ERBα antagonist based on its ability to inhibit REV-ERBα LBD/NcoR interaction in a FRET-based assay and to induce the expression of two REV-ERBα target genes in cultured cells (Kojetin et al., ACS Chem. Biol., 2011; 6: 131-134). These results suggest that SR8278 acts with a molecular mechanism similar to GSK4112, i.e. REV-ERB/NcoR association, but with an opposite outcome. Also SR8278, as mentioned by its disclosers, displayed poor pharmacokinetic properties limiting its pharmacological uses (Kojetin et al., ACS Chem. Biol., 2011; 6: 131-134).

There is thus the need in the art to find new REV-ERB antagonists.

DISCLOSURE OF INVENTION

The aim of the present invention is to provide novel compounds having anti-proliferative and pro-apoptotic activity for their use in cancer therapy, particularly in a breast cancer with the ErbB2-signature and in liver and colon cancers, independently from the expression of the tumor suppressor p53 (i.e. tumors expressing a wild-type or mutated p53 protein, and tumors in which p53 expression is ablated).

The aforementioned objective has been met according to the appended independent claims. Preferred embodiments are set out within the appended dependent claims.

The following paragraphs provide definitions of the various chemical moieties of the compounds according to the invention and are intended to apply uniformly through-out the specification and claims unless an otherwise expressly set out definition provides a broader definition.

The term "alkyl", as used herein, refers to saturated or unsaturated aliphatic hydrocarbon groups. Such term includes straight (unbranched) chains or branched chains. It includes alkenyl groups or alkynyl groups.

Non-limiting examples of alkyl groups according to the invention are, for example, methyl, ethyl, propyl, isopropyl, n-butyl, iso-butyl, tert-butyl, n-pentyl, iso-pentyl, n-hexyl, ethenyl, 1-propenyl, 2-propenyl, 1- or 2-butenyl, ethynyl, 1-propynyl, 2-propynyl, 1- or 2-butynyl, and the like.

Alkyl groups according to the present invention may be unsubstituted or substituted by one or more substituents.

The term "cycloalkyl", as used herein, refers to a saturated or partially unsaturated carbocyclic group having a single ring. It includes cycloalkenyl groups.

Non-limiting examples of cycloalkyl groups according to the invention are, for example, cyclopropane, cyclobutane, cyclopentane, cyclohexane, cycloheptane, cyclopentene, cyclohexene, cyclohexadiene and the like.

Cycloalkyl groups according to the present invention may be unsubstituted or substituted by one or more substituents.

The term "heteroalkyl", as used herein, refers to an alkyl group, as defined above, that is linked to the remainder of the compound via an heteroatom. Heteroalkyl groups can be unsubstituted or substituted by one or more substituents.

As used herein, the term "heteroatom" refers to an atom other than carbon or hydrogen. Heteroatom typically is meant to include oxygen (O), nitrogen (N), and sulphur (S).

The term "alkoxy", as used herein, refers to an alkyl group that is linked to the remainder of the compound by an oxygen atom.

The term "heterocycloalkyl" group, ("non-aromatic heterocycle" group), refers to a cycloalkyl group (non aromatic group) that wherein at least one of the carbon atoms has been replaced by a heteroatom selected from nitrogen, oxygen and sulfur. Heterocycloalkyl groups can be unsubstituted or substituted.

Examples of heterocycloalkyls include, but are not limited to, lactams, lactones, cyclic imides, cyclic thioimides, cyclic carbamates, 1-(1,2,5,6-tetrahydropyridyl), tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl)trioxane, hexahydro-1,3,5-triazine, tetrahydrothiophene, tetrahydrofuran (tetrahydrofuran-2-yl, tetrahydrofuran-3-yl), pyrroline, pyrrolidine, pyrrolidone, pyrrolidione, pyrazoline, pyrazolidine, imidazoline, imidazolidine, 1,3 dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "halogen", as used herein, refers to fluorine, chlorine, bromine and iodine.

The term "aryl", as used herein, refers to a hydrocarbon consisting of a unsubstituted or substituted mono-, bi- or tricarbocyclic ring system, wherein the rings are fused together and at least one of the carbocyclic ring is aromatic. The term "aryl" means for example a cyclic aromatic such as a 6-membered hydrocarbon ring, a two six-membered fused hydrocarbon rings. Non-limiting examples of aryl groups are, for example, phenyl, alpha- or beta-naphthyl, 9,10-dihydroanthracenyl, indanyl, fluorenyl and the like. Aryl groups according to the present invention may be unsubstituted or substituted by one or more substituents.

The term "heteroaryl", as used herein, refers to an aryl as defined above wherein one to four carbon atoms are independently replaced by heteroatoms chosen from the group consisting of nitrogen, oxygen and sulphur. Non-limiting examples of heteroaryl groups are, for example, pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl. Heteroaryl groups according to the present invention may be unsubstituted or substituted by one or more substituents.

The term "aromatic ring", as used herein, refers to a moiety wherein the constituent carbon atoms make up an unsaturated ring system, all atoms in the ring system are $sp^2$ hybridized and the total number of n-electrons is equal to $4n+2$, wherein n is an integer.

The term "heteroaromatic ring", as used herein, refers to an "aromatic ring" as defined above wherein one or more carbon atoms are independently replaced by heteroatoms chosen from the group consisting of nitrogen, oxygen and sulfur.

Unless otherwise indicated, the term "substituted", as used herein, means that one or more hydrogen atoms of the above mentioned groups are replaced with another non-hydrogen atom or functional group, provided that normal valencies are maintained and that the substitution results in a stable compound. Non-limiting example of substitution are, for example, alkyl, substituted alkyl, aryl, substituted aryl, arylalkyl, alkoxy, cycloalkyloxy, aryloxy, arylalkyloxy, hydroxy, heteroaryl, heteroaryloxy, heterocyclyloxy, trifluoromethyl, trifluoromethoxy, carboxy, acyl, aroyl, heteroaroyl, halogen, nitro, cyano, alkoxycarbonyl, aryloxycarbonyl, aralkyloxycarbonyl, cycloalkyloxycarbonyl, heteroaryloxycarbonyl, acyloxy, alkylthio, arylthio, alkylsulfinyl, arylsulfinyl, alkylsulfonyl, arylsulfonyl, —O-aroyl, —O-heteroaroyl, oxo (=O), —C(=O)—$NR^hR^k$, and —$NR^pR^q$, wherein each of $R^h$, $R^k$, $R^p$, and $R^q$ independently represents hydrogen, unsubstituted or substituted alkyl, unsubstituted or substituted cycloalkyl, unsubstituted or substituted aryl, unsubstituted or substituted arylalkyl, unsubstituted or substituted heteroaryl, unsubstituted or substituted heterocyclyl, acyl, aroyl, heteroaroyl, and when $R^h$ and $R^k$, or $R^p$ and $R^q$ are taken together with the nitrogen atom to which they are bound, the group —$NR^hR^k$ or the group $NR^pR^q$ represent a heterocyclyl residue and wherein the terms alkyl, cycloalkyl, aryl, heteroaryl, heterocyclyl are as above defined.

The term "pharmaceutically acceptable salts" refers to salts of the below identified compounds of Formula (I) that retain the desired biological activity and are accepted by regulatory authorities.

As used herein, the term "salt" refers to any salt of a compound according to the present invention prepared from an inorganic or organic acid or base and internally formed salts. Typically, such salts have a physiologically acceptable anion or cation.

Furthermore, the compounds of Formula (I) may form an acid addition salt or a salt with a base, depending on the kind of the substituents, and these salts are included in the present invention, as long as they are pharmaceutically acceptable salts.

Examples of such salts include, but are not restricted to acid addition salts formed with inorganic acids (e. g. hydrochloric acid, hydrobromic acid, sulfuric acid, phosphoric acid, nitric acid, and the like), and salts formed with organic acids such as acetic acid, trifluoroacetic acid, oxalic acid, tartaric acid, succinic acid, malic acid, fumaric acid, maleic acid, ascorbic acid, benzoic acid, alginic acid, polyglutamic acid and naphthalene sulfonic acid. The hydrochloric salt is preferred.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (I) using conventional methods.

The terms "derivative" and "derivatives" refer to each of the compounds of Formula (I) and are meant to include their pharmaceutically acceptable hydrates, solvates, crystalline forms, isotopically-labelled derivatives, tautomers, geometrical or optical isomers, stereoisomers, pharmaceutically active derivatives and also any suitable forms as illustrated hereinafter.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (I) may readily be isolated in association with solvent molecules by crystallization or evaporation of an appropriate solvent to give the corresponding solvates.

The compounds of Formula (I) may be in crystalline form. In certain embodiments, the crystalline forms of the compounds of Formula (I) are polymorphs.

The subject invention also includes isotopically-labelled compounds, which are identical to those recited in Formula (I) and following, but differ for the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, phosphorous, sulfur, fluorine, iodine, and chlorine, such as $^2H$, $^3H$, $^{11}C$, $^{13}C$, $^{14}C$ $^{15}N$, $^{17}O$, $^{18}O$, $^{31}P$, $^{32}P$, $^{35}S$, $^{18}F$, $^{36}Cl$, $^{123}I$, $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e. $^3H$, and carbon-14, i.e. $^{14}C$, isotopes are particularly preferred for their ease of preparation and detectability. $^{11}C$ and $^{18}F$ isotopes are particularly useful in PET (Positron Emission Tomography), and $^{125}I$ isotopes are particularly useful in SPECT (Single Photon Emission Computerized Tomography), all useful in brain imaging. Furthermore, substitution with heavier isotopes such as deuterium, i.e. $^2H$, can afford certain therapeutic advantages resulting from greater metabolic stability, for example increased in vivo half-life or reduced dosage requirements and, hence, may be preferred in some circumstances. Isotopically-labelled compounds of Formula (I) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (I) may exist in the form of other tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (I) may have asymmetric carbon atoms or axial asymmetries in some cases and, correspondingly, it may exist in the form of optical isomers such as an (R)-form, an (S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formula (I) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist.

The term "pharmaceutically active derivative" refers to any compound derived from the compounds of Formula (I) that upon administration to the recipient, is capable of providing directly or indirectly, the activity disclosed herein.

The present invention also encompasses active metabolites of compounds of Formula (I).

According to a first aspect of the invention, compounds of Formula (I)

[Structure of Formula (I)]

or pharmaceutically acceptable salts or solvates thereof are provided.

In the compounds of Formula (I):

Ar and Ar' are independently selected from the group consisting of a 5- to 10-membered aromatic or heteroaromatic single or fused rings comprising up to 3 heteroatoms selected from N, O, S;

R is selected from the group consisting of hydrogen, a linear or branched unsubstituted or substituted $C_{1-6}$ alkyl and an unsubstituted or substituted aryl $C_{1-6}$ alkyl;

$R_1$, $R_2$, $R_3$ and $R_4$ are independently selected from the group consisting of H, halogen, linear or branched, unsubstituted or substituted $C_{1-6}$ alkyl, $C_{1-6}$ alkoxy, hydroxy $C_{1-6}$ alkyl, OH, CN, fluoro $C_{1-6}$ alkyl, fluoro $C_{1-6}$ alkoxy; $R_1$, $R_2$, $R_3$ and $R_4$ can be attached to any position of Ar and Ar' group, respectively;

Y is selected from the group consisting of N or CH;

X is selected from the group consisting of CH or N;

$R_5$ and $R_6$ are independently selected from the group consisting of H, halogen, unsubstituted or substituted linear or branched $C_{1-6}$ alkyl, =O, unsubstituted or substituted aryl, unsubstituted or substituted aryl $C_{1-6}$ alkyl, hydroxy $C_{1-6}$ alkyl, $C_{1-6}$ alkylCO, unsubstituted or substituted arylCO, unsubstituted or substituted aryl $C_{1-6}$ alkylCO, $COOR_7$, $CONR_8R_9$, $SO_2R_{10}$ wherein $R_7$, $R_8$, $R_9$ and $R_{10}$ are independently selected from the group consisting of hydrogen, linear or branched $C_{1-6}$ alkyl; $R_5$ and $R_6$ can be attached to any carbon atom of the ring to which they are connected and they may be connected to the same carbon atom or to different carbon atoms of the ring; and $R_{11}$ is selected from the group consisting of H, linear or branched $C_{1-6}$ alkyl, $C_{1-6}$ alkylCO, aryl, aryl $C_{1-6}$ alkyl;

or $R_5$ and $R_6$, or $R_5$ and $R_{11}$ or $R_6$ and $R_{11}$ are linked together to form an unsubstituted or substituted 4- to 10-membered ring, saturated or unsaturated, and containing up to two nitrogen atoms;

q and p are, independently, 0 or an integer from 1 to 2 with the proviso that when both Y and X are N, neither q and p are 0;

$R_{12}$ and $R_{13}$ are independently selected from the group consisting of H, F, $C_{1-6}$ alkyl, $C_{1-6}$ alkyl-OH, =O, OH, COOH, $CO_2Me$, $CONH_2$, CONHMe, $CONMe_2$ and can be attached to any position of the ring to which they are connected and they may be connected to the same carbon atom or to different carbon atoms of the ring;

W is selected from the group consisting of a bond and a heteroatom selected from the group consisting of O, S and $NR_{14}$, wherein $R_{14}$ is selected from the group consisting of H, linear or branched $C_{1-6}$ alkyl, $C_{1-6}$ alkylCO, unsubstituted or substituted aryl, unsubstituted or substituted aryl $C_{1-6}$ alkyl, unsubstituted or substituted arylCO, $SO_2R_{15}$, $CONR_{16}R_{17}$, $COOR_{18}$, wherein $R_{15}$, $R_{16}$, $R_{17}$ and $R_{18}$ are independently selected from the group consisting of H, linear or branched $C_{1-6}$ alkyl;

m is an integer from 1 to 3, n is 0 or an integer from 1 to 3 with the proviso that when W is bond, n is not 0;

provided that the compound of Formula (I) is not

4-[[[1-(4-methoxyphenyl)cyclopentyl]amino]methyl]-2-[(4-methyl-1-piperazinyl)methyl]-phenol;

4-[[[1-(2-fluorophenyl)cyclopentyl]amino]methyl]-2-[(4-methyl-1-piperazinyl)methyl]-phenol and 4-[[[1-(2-methoxyphenyl)cyclopentyl]amino]methyl]-2-[(4-methyl-1-piperazinyl)methyl]-phenol.

Preferably, Ar and Ar' are, independently, selected from benzene, pyridine, naphthalene, thiophene rings;

R is selected from the group consisting of H, $CH_3$, unsubstituted or substituted phenyl$CH_2$;

$R_1$, $R_2$, $R_3$ and $R_4$ are independently selected from the group consisting of H, F, Cl, $CH_3$, OH, $OCH_3$, $CH_2OH$, $CF_3$, $CHF_2$, $CH_2F$, $CF_2CF_3$, $OCF_3$, $OCF_2CF_3$, CN;

$R_5$ and $R_6$ are independently selected from the group consisting of H, F, $CH_3$, =O, unsubstituted or substituted phenyl, unsubstituted or substituted pyridyl, unsubstituted or substituted phenyl$CH_2$, $CH_2OH$, $CH_3CO$, unsubstituted or substituted phenylCO, unsubstituted or substituted phenyl$CH_2CO$, $COOR_7$, $CONR_8R_9$, $SO_2R_{10}$ wherein $R_7$, $R_8$, $R_9$ and $R_{10}$ are independently selected from the group consisting of H and $CH_3$;

$R_{11}$ is selected from the group consisting of H, $CH_3$, Et, i-Pr, phenyl$C_{1-6}$ alkyl, $CH_3CO$, phenyl;

or $R_5$ and $R_6$, or $R_5$ and $R_{11}$ or $R_6$ and $R_{11}$ are linked together to form a ring and thus the moiety

[Structure]

has a meaning selected from the group consisting of:

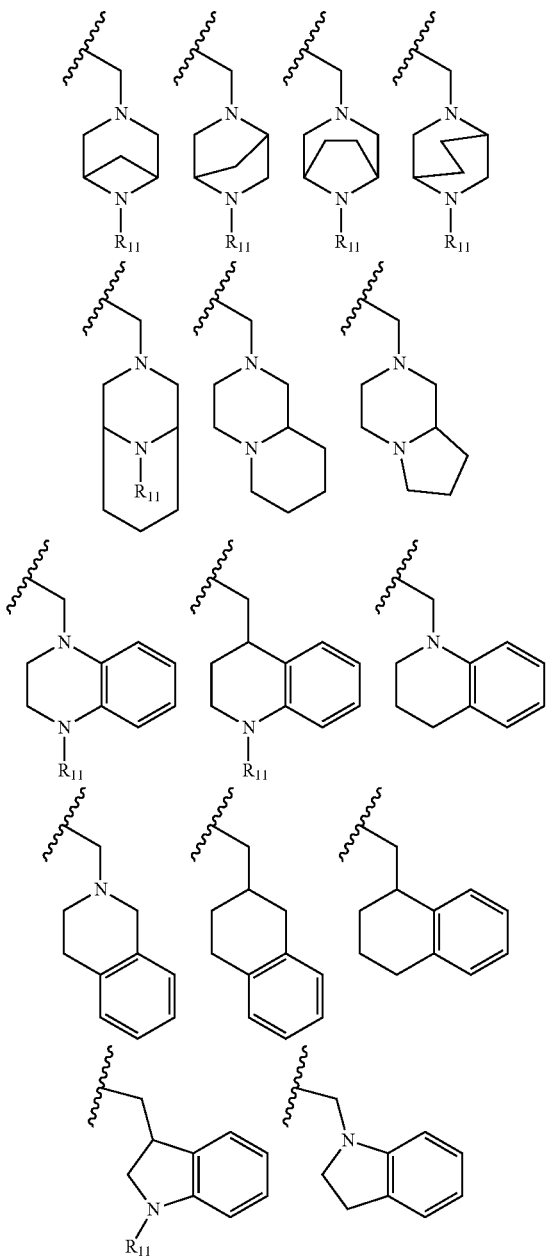

p and q are, independently, 0 or 1;
$R_{12}$ and $R_{13}$ are independently selected from the group consisting of H, F, $CH_3$, $CH_2OH$, OH, =O, and they are connected to the same carbon atom or to different carbon atoms of the ring;
W is selected from the group consisting of a bond and a heteroatom selected from the group consisting of O and $NR_{14}$, wherein $R_{14}$ is H, $CH_3$, $COCH_3$, unsubstituted or substituted phenyl, unsubstituted or substituted phenyl $CH_2$, unsubstituted or substituted phenylCO, $SO_2R_{15}$, $CONR_{16}R_{17}$, $COOR_{18}$, wherein $R_{15}$, $R_{16}$, $R_{17}$ and $R_{18}$ are independently selected from the group consisting of H and $CH_3$; more preferably W is selected from the group consisting of a bond, O, NH, $NCH_3$, $NCOCH_3$; $NCH_2$phenyl;
m is an integer from 1 to 3, and n is an integer from 1 to 2.

According to a first embodiment of the above aspect, the compounds of the invention can have the following Formula (I'):

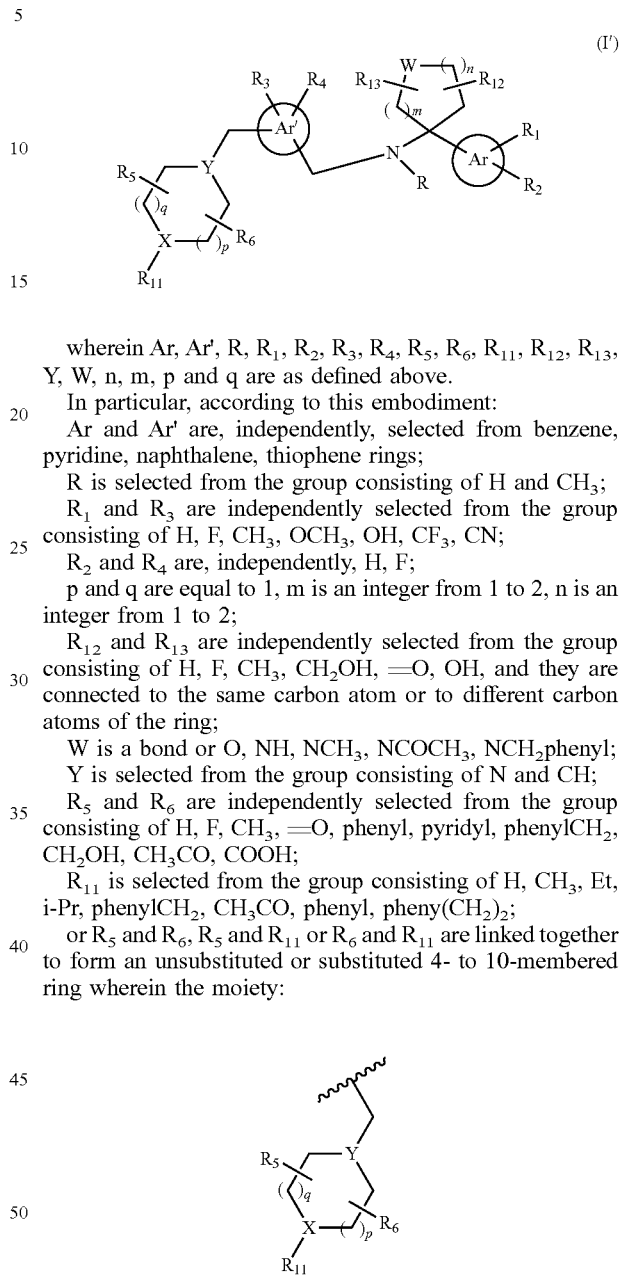

wherein Ar, Ar', R, $R_1$, $R_2$, $R_3$, $R_4$, $R_5$, $R_6$, $R_{11}$, $R_{12}$, $R_{13}$, Y, W, n, m, p and q are as defined above.
In particular, according to this embodiment:
Ar and Ar' are, independently, selected from benzene, pyridine, naphthalene, thiophene rings;
R is selected from the group consisting of H and $CH_3$;
$R_1$ and $R_3$ are independently selected from the group consisting of H, F, $CH_3$, $OCH_3$, OH, $CF_3$, CN;
$R_2$ and $R_4$ are, independently, H, F;
p and q are equal to 1, m is an integer from 1 to 2, n is an integer from 1 to 2;
$R_{12}$ and $R_{13}$ are independently selected from the group consisting of H, F, $CH_3$, $CH_2OH$, =O, OH, and they are connected to the same carbon atom or to different carbon atoms of the ring;
W is a bond or O, NH, $NCH_3$, $NCOCH_3$, $NCH_2$phenyl;
Y is selected from the group consisting of N and CH;
$R_5$ and $R_6$ are independently selected from the group consisting of H, F, $CH_3$, =O, phenyl, pyridyl, phenyl$CH_2$, $CH_2OH$, $CH_3CO$, COOH;
$R_{11}$ is selected from the group consisting of H, $CH_3$, Et, i-Pr, phenyl$CH_2$, $CH_3CO$, phenyl, pheny$(CH_2)_2$;
or $R_5$ and $R_6$, $R_5$ and $R_{11}$ or $R_6$ and $R_{11}$ are linked together to form an unsubstituted or substituted 4- to 10-membered ring wherein the moiety:

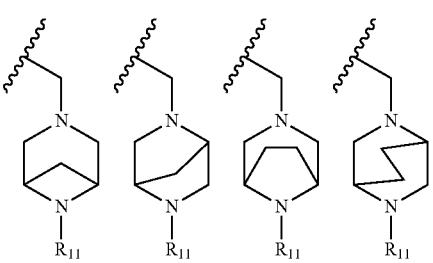

has a meaning selected from the group consisting of:

-continued

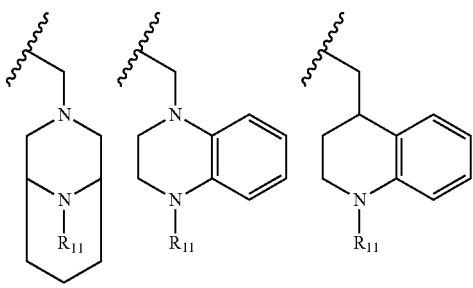

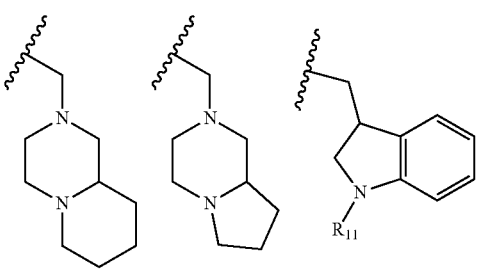

In particular, the moiety:

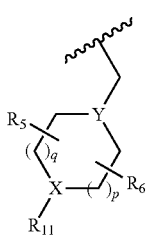

has a meaning selected from the group consisting of:

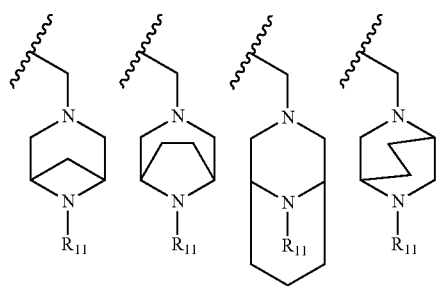

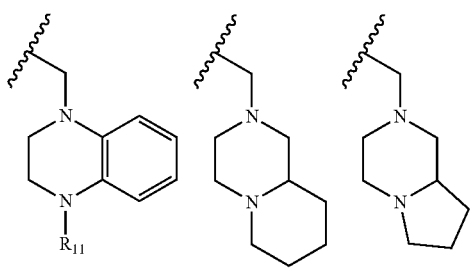

-continued

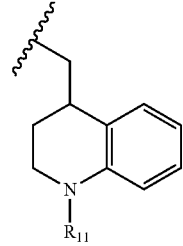

According to a second embodiment of the above aspect, the compounds of the invention can have the following Formula (I"):

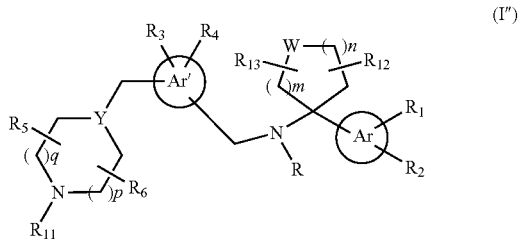

(I")

wherein Ar, Ar', R, $R_1$, $R_2$, $R_3$, $R_4$, $R_5$, $R_6$, $R_{11}$, $R_{12}$, $R_{13}$, Y, W, n, m, p and q are as defined above.

In particular, according to this embodiment:

Ar and Ar' are, independently, selected from benzene, pyridine, naphthalene, thiophene rings, in particular Ar and Ar' are benzene;

R is H and $CH_3$;

$R_1$ and $R_3$ are independently selected from the group consisting of H, F, $CH_3$, $OCH_3$, OH, $CF_3$;

$R_2$ and $R_4$ are both H;

p and q are equal to 1, m is an integer from 1 to 2, n is an integer from 1 to 2;

$R_{12}$ and $R_{13}$ are independently selected from the group consisting of H, F, $CH_3$, $CH_2OH$, =O, OH, or $R_{12}$ and $R_{13}$ are connected to the same carbon atom and have both the same meaning selected from F and $CH_3$;

W is a bond or O, NH, $NCH_3$, $NCOCH_3$; $NCH_2$phenyl;

Y is N or CH;

$R_5$ and $R_6$ are independently selected from the group consisting of H, F, $CH_3$, =O, phenyl, pyridyl, phenyl$CH_2$, $CH_2OH$, $CH_3CO$, COOH;

$R_{11}$ is selected from the group consisting of H, $CH_3$, Et, i-Pr, phenyl$CH_2$, $CH_3CO$, phenyl;

or $R_5$ and $R_6$, $R_5$ and $R_{11}$ or $R_6$ and $R_{11}$ are linked together to form an unsubstituted or substituted 4- to 10-membered ring wherein the moiety:

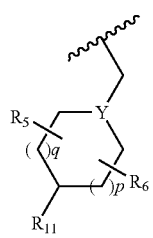

has a meaning selected from the group consisting of:

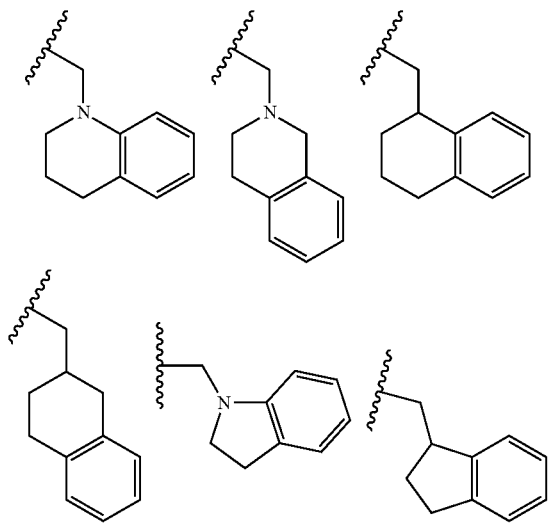

In particular, the moiety:

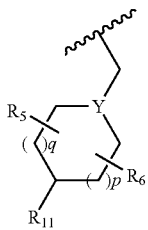

has a meaning selected from the group consisting of:

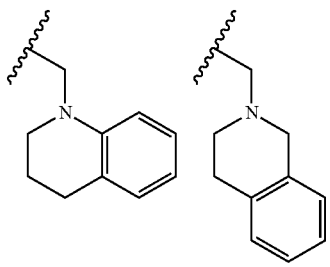

According to a further embodiment of the above aspect, the compounds of Formula (I) can be selected from the group consisting of:

4-[[[1-(2-fluorophenyl)cyclopentyl]amino]methyl]-2-(1-piperidylmethyl)phenol dihydrochloride;

4-[[[1-(2-fluorophenyl)cyclohexyl]amino]methyl]-2-[(4-methylpiperazin-1-yl)methyl]phenol trihydrochloride;

1-(2-fluorophenyl)-N-[[3-[(4-methylpiperazin-1-yl)methyl]phenyl]methyl]cyclopentanamine trihydrochloride;

1-(2-fluorophenyl)-N-[[4-methoxy-3-[(4-methylpiperazin-1-yl)methyl]phenyl]methyl]cyclopentanamine trihydrochloride;

4-[[[1-(2-fluorophenyl)cyclopentyl]-methyl-amino]methyl]-2-[(4-methylpiperazin-1-yl)methyl]phenol trihydrochloride;

2-[(4-methylpiperazin-1-yl)methyl]-4-[[(1-phenylcyclopentyl)amino]methyl]phenol trihydrochloride;

1-[4-[[5-[[[1-(2-fluorophenyl)cyclopentyl]amino]methyl]-2-hydroxyphenyl]methyl]piperazin-1-yl]ethanone dihydrochloride;

4-[[[1-(2-fluorophenyl)cyclopentyl]amino]methyl]-2-[(4-phenylpiperazin-1-yl)methyl]phenol trihydrochloride;

2-[(4-ethylpiperazin-1-yl)methyl]-4-[[[1-(2-fluorophenyl)cyclopentyl]amino]methyl]phenol trihydrochloride;

4-[[[1-(2-fluorophenyl)cyclopentyl]amino]methyl]-2-(piperazin-1-ylmethyl) phenol;

2-[(4-benzylpiperazin-1-yl)methyl]-4-[[[1-(2-fluorophenyl)cyclopentyl]amino]methyl]phenol trihydrochloride;

4-[[[1-(2-fluorophenyl)cyclopentyl]amino]methyl]-2-[(4-isopropylpiperazin-1-yl)methyl]phenol trihydrochloride;

4-[[[1-(2-fluorophenyl)tetrahydropyran-4-yl]amino]methyl]-2-[(4-methylpiperazin-1-yl)methyl]phenol trihydrochloride;

4-(2-fluorophenyl)-4-[[4-hydroxy-3-[(4-methylpiperazin-1-yl)methyl]phenyl]methylamino]cyclohexanone trihydrochloride;

4-[[[4,4-difluoro-1-(2-fluorophenyl)cyclohexyl]amino]methyl]-2-[(4-methyl-piperazin-1-yl)methyl]phenol trihydrochloride;

1-(2-fluorophenyl)-N-[[3-[(1-methyl-4-piperidyl)methyl]phenyl]methyl]cyclopentanamine dihydrochloride;

1-(2-fluorophenyl)-N-methyl-N-[[3-[(1-methyl-4-piperidyl)methyl]phenyl]methyl]cyclopentanamine dihydrochloride;

4-[[[1-benzyl-4-(2-fluorophenyl)-4-piperidyl]amino]methyl]-2-[(4-methylpiperazin-1-yl)methyl]phenol tetrahydrochloride;

4-[[[1-(2,4-difluorophenyl)cyclopentyl]amino]methyl]-2-[(4-methylpiperazin-1-yl)methyl]phenol trihydrochloride;

4-[[[1-(3-fluorophenyl)cyclopentyl]amino]methyl]-2-[(4-methylpiperazin-1-yl)methyl]phenol trihydrochloride;

4-[[[1-(4-fluorophenyl)cyclopentyl]amino]methyl]-2-[(4-methylpiperazin-1-yl)methyl]phenol trihydrochloride;

2-[(4-methylpiperazin-1-yl)methyl]-4-[[[1-(3-thienyl)cyclopentyl]amino]methyl]phenol trihydrochloride.

The following compounds may be also synthesized with the same method used for the compounds above:

2-[[[1-(2-fluorophenyl)cyclohexyl]amino]methyl]-6-[(4-methylpiperazin-1-yl)methyl]phenol;

1-(2-fluorophenyl)-N-[[2-[(4-methylpiperazin-1-yl)methyl]-4-pyridyl]methyl]cyclohexanamine;

4-[[[1-(2-fluorophenyl)cyclohexyl]amino]methyl]-2-[(5-methyl-2,5-diazabicyclo[2.2.2]octan-2-yl)methyl]phenol;

4-[[[1-(2-fluorophenyl)cyclohexyl]amino]methyl]-2-[(4-methyl-2,3-dihydroquinoxalin-1-yl)methyl]phenol;

2-(1,3,4,6,7,8,9,9a-octahydropyrido[1,2-a]pyrazin-2-ylmethyl)-4-[[[1-(2-fluorophenyl)cyclohexyl]amino]methyl]phenol;

4-[[[1-(2-fluorophenyl)cyclohexyl]amino]methyl]-2-[(9-methyl-3,9-diazabicyclo[3.3.1]nonan-3-yl)methyl]phenol;

4-[[[1-(2-fluorophenyl)cyclohexyl]amino]methyl]-2-[(8-methyl-3,8-diazabicyclo[3.2.1]octan-3-yl)methyl]phenol;

4-[[[1-(3,5-difluorophenyl)cyclopentyl]amino]methyl]-2-[(4-methylpiperazin-1-yl)methyl]phenol;

4-[[[1-(3-fluoro-2-naphthyl)cyclohexyl]amino]methyl]-2-[(4-methylpiperazin-1-yl)methyl]phenol;

4-[[[1-(2-fluorophenyl)cyclohexyl]amino]methyl]-3-[(4-methylpiperazin-1-yl)methyl]phenol;

2-[[[1-(2-fluorophenyl)cyclohexyl]amino]methyl]-4-[(4-methylpiperazin-1-yl)methyl]phenol;

4-[[[1-(2-hydroxyphenyl)cyclohexyl]amino]methyl]-2-[(4-methylpiperazin-1-yl)methyl]phenol;

4-[[[1-(2-fluorophenyl)-4-methyl-cyclohexyl]amino]methyl]-2-[(4-methylpiperazin-1-yl)methyl]phenol;

4-[[[1-(2-fluorophenyl)-4-(hydroxymethyl)cyclohexyl]amino]methyl]-2-[(4-methylpiperazin-1-yl)methyl]phenol;

4-[[[1-(2-fluorophenyl)-4-hydroxy-cyclohexyl]amino]methyl]-2-[(4-methylpiperazin-1-yl)methyl]phenol;

1-(2-fluorophenyl)-N-[[3-[(1-phenethyl-4-piperidyl)methyl]phenyl]methyl]cyclohexanamine;

4-[[[1-(2-fluorophenyl)-4-hydroxy-4-methyl-cyclohexyl]amino]methyl]-2-[(4-methylpiperazin-1-yl)methyl]phenol;

4-[[[1-(2-fluorophenyl)-4,4-dimethyl-cyclohexyl]amino]methyl]-2-[(4-methylpiperazin-1-yl)methyl]phenol;

4-[[5-[[[1-(2-fluorophenyl)cyclohexyl]amino]methyl]-2-hydroxy-phenyl]methyl]-1-methyl-piperidine-2-carboxylic acid;

1-(2-fluorophenyl)-N-[[3-[(1-methyl-4-piperidyl)methyl]phenyl]methyl]cyclohexanamine;

1-(3-fluorophenyl)-N-[[3-[(1-methyl-4-piperidyl)methyl]phenyl]methyl]cyclopentanamine;

N-[[3-[(l-benzyl-4-piperidyl)methyl]phenyl]methyl]-1-(2-fluorophenyl)cyclohexanamine;

1-(2-fluorophenyl)-N-[[3-[(1-methyl-3,4-dihydro-2H-quinolin-4-yl)methyl]phenyl]methyl]cyclohexanamine;

N-[[3-(cyclohexylmethyl)phenyl]methyl]-1-(2-fluorophenyl)cyclohexanamine;

1-(2-fluorophenyl)-N-[[3-[(4-methylcyclohexyl)methyl]phenyl]methyl]cyclohexanamine.

The compounds exemplified in this invention may be prepared from readily available starting materials using the following general methods and procedures for example exemplified in *Michael Smith, Jerry March—March's Advanced Organic Chemistry: reactions mechanisms and structure —6th Edition*, John Wiley & Sons Inc., 2007.

It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W. Green and Peter G. M. Wuts—*Protective Groups in Organic Synthesis, Fourth Edition*, John Wiley & Sons Inc., 2006.

It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The synthesis of a compound of Formula (I), according to the synthetic processes described below, can be conducted in a stepwise manner, whereby each intermediate is isolated and purified by standard purification techniques such as, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The compounds of Formula (I), prepared with the methods described herein below, may be treated or purified by conventional techniques or means for example by filtration, distillation, chromatography, recrystallization and combination thereof.

The salts of compounds of Formula (I) may be prepared by reacting a basic compound with the desired acid in solution.

General Procedures

In one embodiment, a compound of Formula (I) can be obtained by application of the chemical transformations reported in the schemes herein described.

According to Scheme 1, compounds of Formula (I), wherein R is H and $R_1$, $R_2$, $R_3$, $R_4$, $R_{12}$, $R_{13}$, $R_5$, $R_6$, $R_{11}$, Ar, Ar', X, Y, W, n, m, p and q are as defined in Formula (I) above, named compounds of Formula Ia, can be prepared by reductive amination reaction of aldehydes of Formula II wherein $R_3$, $R_4$, $R_5$, $R_6$, $R_{11}$, Ar', X, Y, p and q are as defined in Formula (I) above with amines of Formula III wherein $R_1$, $R_2$, $R_{12}$, $R_{13}$, Ar, W, n and m are as defined in Formula (I) in the presence of reducing agent, such as sodium triacetoxyborohydride ($NaBH(OAc)_3$) and using a moderately polar aprotic solvent, such as dichloromethane (DCM).

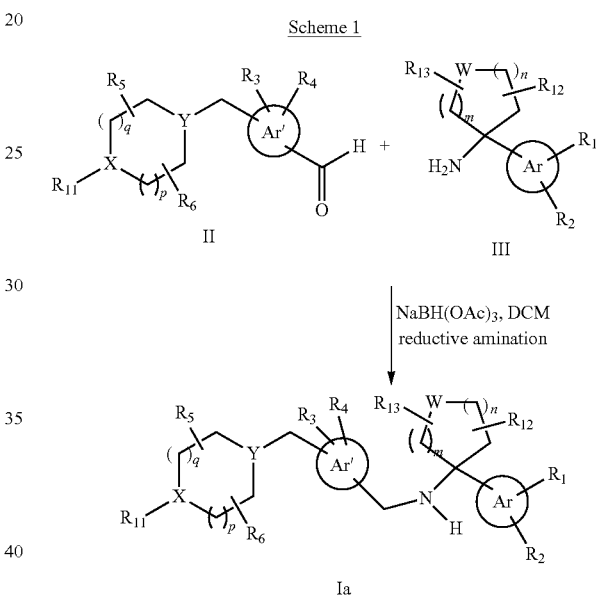

Scheme 1

According to Scheme 2, compounds of Formula (I), wherein R is different from H, and $R_1$, $R_2$, $R_3$, $R_4$, $R_{12}$, $R_{13}$, $R_5$, $R_6$, $R_{11}$, Ar, Ar', X, Y, W, n, m, p and q are as defined in Formula (I) above, named compounds of Formula Ib, can be prepared by reductive amination reaction of compounds of Formula Ia with aldehydes of Formula IV where R' is H, $C_{1-5}$ alkyl or aryl $C_{1-5}$ alkyl.

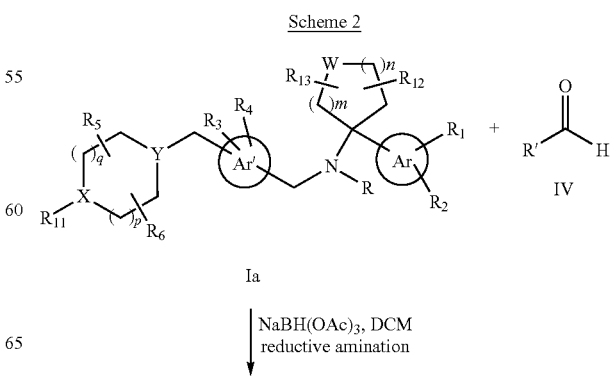

Scheme 2

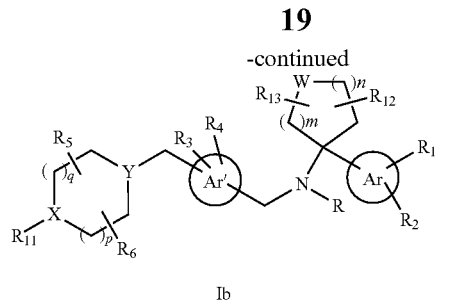

Ib

Alternatively, according to Scheme 3, compounds of Formula Ib can be prepared by "one-pot" procedure, consisting of reductive amination reaction of aldehydes of Formula II (or IV, where R' is H, $C_{1-5}$ alkyl or aryl $C_{1-5}$ alkyl) with amines of Formula III in the presence of a reducing agent, such as NaBH(OAc)$_3$ and using moderately polar aprotic solvent, such as DCM until to complete transformation of the starting materials, followed by the addition of the appropriate aldehydes of Formula IV (or II), where R' is H, $C_{1-5}$ alkyl or aryl $C_{1-5}$ alkyl.

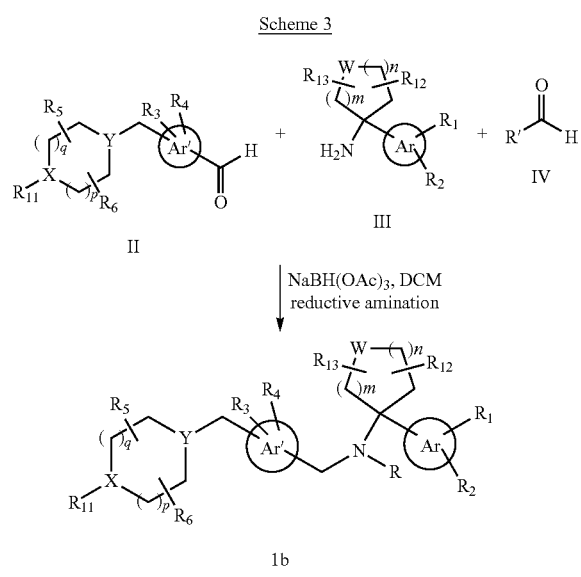

Scheme 3

Synthesis of Compounds of Formula (II)

According to Scheme 4, compounds of Formula II, wherein Y is N and at least one of $R_3$ and $R_4$, is OH or OMe and $R_5$, $R_6$, $R_{11}$, Ar', X, p and q are as defined in Formula (I) above, named compounds of Formula IIa, can be prepared by Mannich reaction of aldehydes of Formula Va with amines of Formula VI in presence of formaldehyde (HCHO). The reaction is preferably conducted in polar solvent, such as ethanol (EtOH) or moderately polar aprotic solvent as DCM, at temperatures ranging from 45° C. to 80° C. for 12 h.

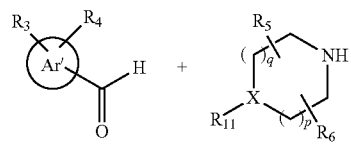

Scheme 4

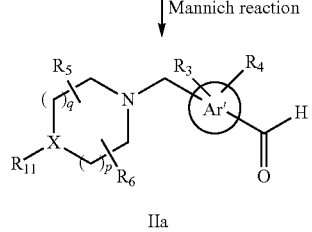

IIa

According to Scheme 5, compounds of Formula II, wherein Y is N and both $R_3$ and $R_4$ are different from OH or OMe and $R_5$, $R_6$, $R_{11}$, Ar', X, p and q, are as defined in Formula (I) above, named compounds of Formula IIb, can be prepared in a three steps procedure which consists of: 1) reductive amination reaction of alkylcarboxylate-arylaldehydes (preferably methylcarboxylate-arylaldehydes or ethylcarboxylate-arylaldehydes) of Formula Vb with amines of Formula VI in the presence of a reducing agent, such as, NaBH(OAc)$_3$ in moderately polar aprotic solvent, such as DCM; 2) reduction reaction of alkylcarboxylates (preferably methylcarboxylates or ethylcarboxylates) of Formula IIb' in the presence of a reducing agent, such as lithium aluminum hydride (LiAlH$_4$); and 3) oxidation of the primary alcohols of Formula IIb'' to aldehydes of Formula IIb using oxidizing agents, such as manganese dioxide (MnO$_2$) in apolar aprotic solvent, such as diethyl ether (Et$_2$O).

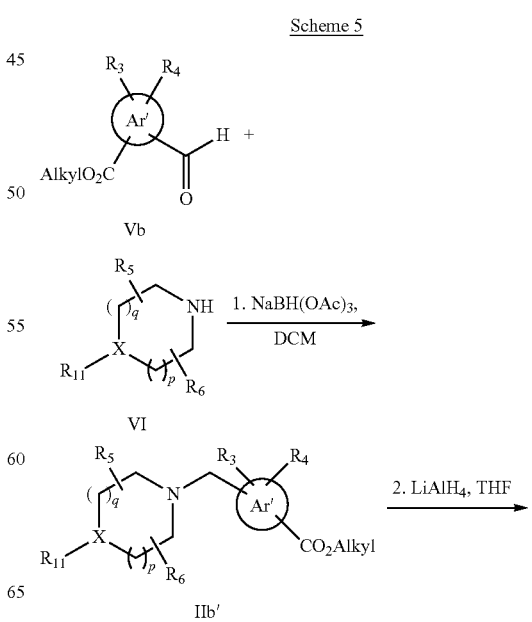

Scheme 5

-continued

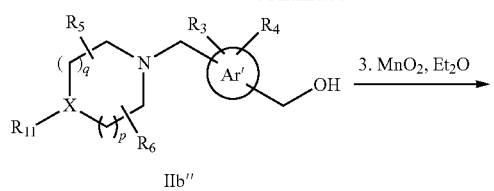

IIb''

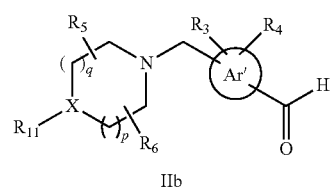

IIb

-continued

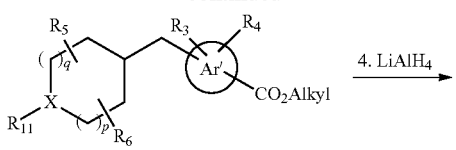

IIc'''

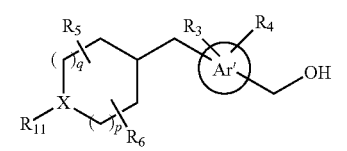

IIc''''

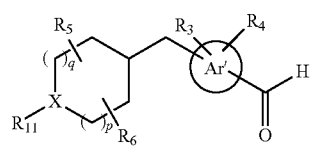

IIc

According to Scheme 6, compounds of Formula II, wherein Y is CH and $R_3$, $R_4$, $R_5$, $R_6$, $R_{11}$, Ar', X, q and p are as defined in Formula (I) above, named compounds of Formula IIc, can be prepared in a five steps procedure which consists of: 1) preparation of triphenylphosphonium salts of Formula IIc' by treatment of compound of Formula VII where Z is Br, or I, with triphenylphosphine in aprotic solvent as toluene; 2) olefination reaction of compounds of Formula IIc' with ketones of Formula VIII in the presence of bases such as LHMDS at room temperature in apolar aprotic solvent such as tetrahydrofurane (THF); 3) hydrogenation reaction of compounds of Formula IIc'' in the presence of palladium/carbon (Pd/C) and triethylsilane ($Et_3SiH$) in polar solvent such as methanol (MeOH); 4) reduction reaction of alkylcarboxylates (preferably methylcarboxylates or ethylcarboxylates) of Formula IIc''' in the presence of a reducing agent, such as $LiAlH_4$; and 5) oxidation of primary alcohols of Formula IIc'''' in aldehydes of Formula IIc using oxidizing agents, such as manganese dioxide ($MnO_2$) in apolar aprotic solvent, such as $Et_2O$.

Synthesis of Compounds of Formula (III)

According to Scheme 7 (Method A), compounds of Formula III, wherein W is a bond, $R_{12}$ and $R_{13}$ is H and $R_1$, $R_2$, Ar, n and m, are as defined in Formula (I) above, named compounds of Formula IIIa, can be prepared following a standard synthetic procedure reported in Balderman et al., Synthesis, 1978; 24-26, which consists of: 1) nucleophilic addition of the corresponding organolithium or Grignard derivatives of arylhalides of Formula IX, where Z is Br or I, to ketones of Formula Xa; 2) treatment of arylcycloalkanols of Formula IIIa' with sodium azide ($NaN_3$) in the presence of trifluoroacetic acid (TFA) in DCM at low temperature from −20° C. to 5° C., preferably at 0° C.; and 3) reduction of azides of Formula IIIa'' by using $LiAlH_4$ in aprotic polar solvent such as THF.

Scheme 6

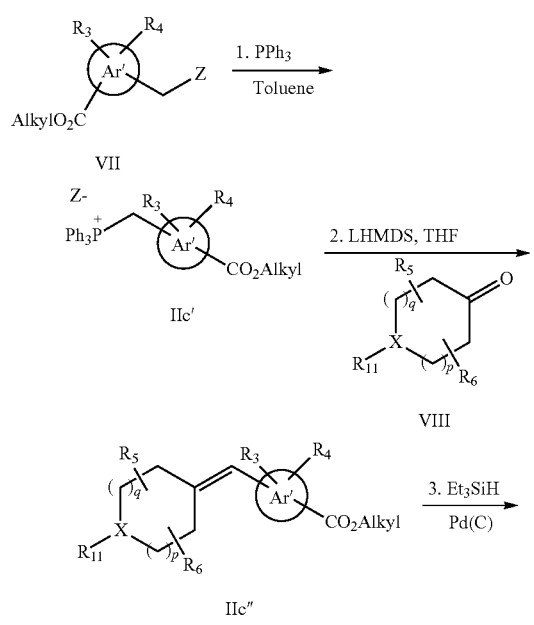

Scheme 7

Method A

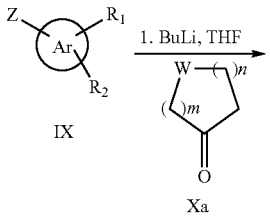

IX

Xa

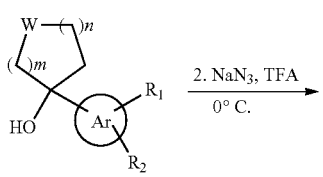

IIIa'

-continued

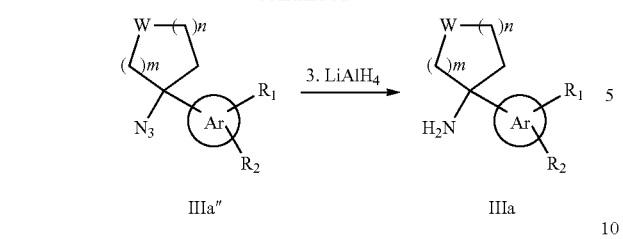

IIIa″    IIIa

Method B

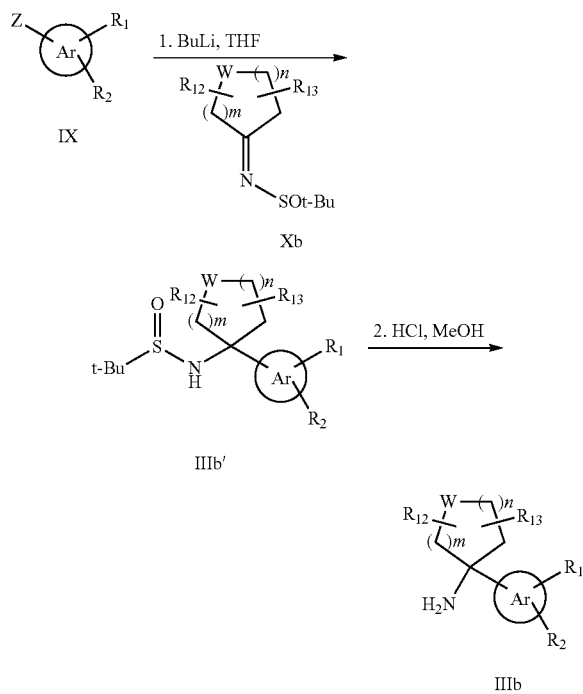

IX

Xb

IIIb′

IIIb

Method C

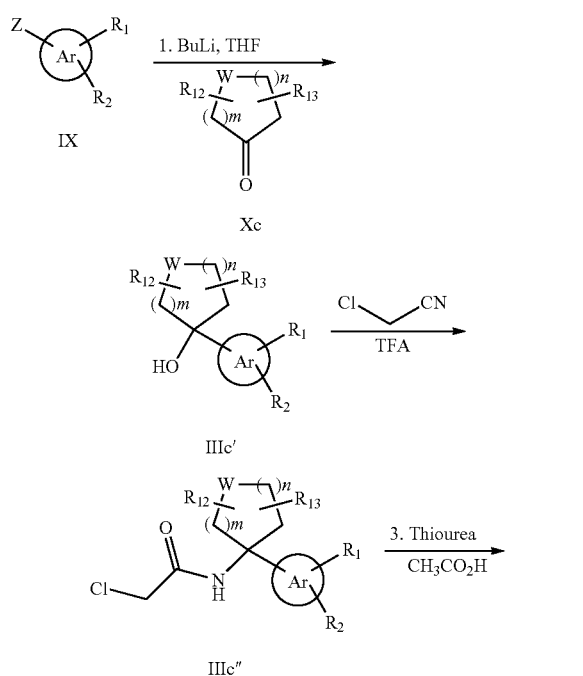

IX

Xc

IIIc′

IIIc″

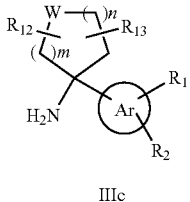

IIIc

According to Scheme 7 (Method B), compounds of Formula III, wherein W is a bond or O and $R_{12}$ and $R_{13}$ is different from H and $R_1$, $R_2$, Ar, n and m are as defined in Formula (I) above, named compounds of Formula IIIb, can be prepared following standard synthetic procedure reported in McMahon et al., Org. Lett., 2004; 6: 1645-1647; Ellmann et al., Acc. Chem. Res., 2002; 35: 984-995, which consists in: 1) nucleophilic addition of the corresponding organolithium or Grignard derivatives of arylhalides of Formula IX, where Z is I, or Br, to tert-butylsulfinyl ketimines of Formula Xb and 2) treatment of sulfinamide of Formula IIIb′ under acidic conditions, such as HCl solution in MeOH.

According to Scheme 7 (Method C), compounds of Formula III, wherein W is a bond or N and $R_{12}$, $R_{13}$, $R_1$, $R_2$, Ar, n and m are as defined in Formula (I) above, named compounds of Formula IIIc, can be prepared following a standard synthetic procedure reported in de Koning et al., Org. Process. Dev., 2011; 15: 1256-1265; Content at al., Org. Process. Dev., 2013; 17: 193-201, which consists of: 1) nucleophilic addition of the corresponding organolithium or Grignard derivates of arylhalides of Formula IX, where Z is I, or Br, to ketones of Formula Xc; 2) treatment of cycloalkanols of Formula IIIc′ with chloroacetonitrile in the presence of strong acid such as sulfuric acid ($H_2SO_4$) or TFA and 3) chloroacetamide cleavage of compounds of Formula IIIc″ by using thiourea under acidic conditions, as for example acetic acid ($CH_3CO_2H$) in a polar solvent such as MeOH.

According to Scheme 8, compounds of Formula Xb wherein W, $R_{12}$, $R_{13}$, n and m are as defined in Formula (I) above, can be prepared by condensation of tert-butanesulfinamide with cyclic ketones of Formula Xa, employing titanium (IV) isopropoxide [Ti(OiPr)$_4$] in THF at room temperature (McMahon et al., Org. Lett., 2004; 6: 1645-1647; Ellmann et al., Acc. Chem. Res., 2002; 35: 984-995).

Scheme 8

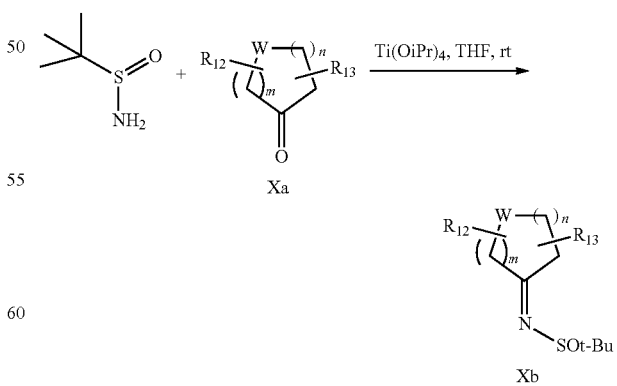

Xa

Xb

Compounds of Formula IV, Va, Vb, VI, VII, VIII, IX, Xa and Xc are known compounds or can be easily prepared from known compounds by known methods.

A second aspect of the present invention is related to a pharmaceutical composition comprising a compound of Formula (I) as disclosed above, included 4-[[[1-(4-methoxyphenyl)cyclopentyl]amino]methyl]-2-[(4-methyl-1-piperazinyl)methyl]-phenol, 4-[[[1-(2-fluorophenyl)cyclopentyl amino]methyl]-2-[(4-methyl-1-piperazinyl)methyl]-phenol and 4-[[[1-(2-methoxyphenyl)cyclopentyl]amino]methyl]-2-[(4-methyl-1-piperazinyl)methyl]-phenol and a pharmaceutically acceptable carrier, stabilizer, diluent or excipient thereof.

A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous and intravenous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular, intranasal and pulmonary routes. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions.

Liquid forms suitable for oral administration may include a suitable aqueous or non-aqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable carriers known in the art.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring agent such as cherry or orange flavor. To prevent breakdown during transit through the upper portion of the gastrointestinal tract, the composition be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound of Formula (I) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I) per dosage unit for daily administration.

In some embodiments, the amounts effective for topical formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

With respect to formulations with respect to any variety of routes of administration, methods and formulations for the administration of drugs are disclosed in *Remington's Phar-* maceutical Sciences, 17th Edition, Gennaro et al. Eds., Mack Publishing Co., 1985, and Remington's Pharmaceutical Sciences, Gennaro A R ed. 20th Edition, 2000, Williams & Wilkins PA, USA, and Remington: The Science and Practice of Pharmacy, 21st Edition, Lippincott Williams & Wilkins Eds., 2005; and in Ansel's Pharmaceutical Dosage Forms and Drug Delivery Systems, 8th Edition, Lippincott Williams & Wilkins Eds., 2005.

The above described components for orally administered or injectable compositions are merely representative.

The compounds of this invention can also be administered in sustained release forms or from sustained release drug delivery systems.

Moreover, the pharmaceutical compositions according to the invention may comprise a second therapeutic agent, for example known anticancer agents for which cancer cells develop resistance to the treatment.

A third aspect of the present invention is related to the use of compounds of Formula (I) as disclosed above, included 4-[[[1-(4-methoxyphenyl)cyclopentyl]amino]methyl]-2-[(4-methyl-1-piperazinyl)methyl]-phenol, 4-[[[1-(2-fluorophenyl)cyclopentyl]amino]methyl]-2-[(4-methyl-1-piperazinyl)methyl]-phenol and 4-[[[1-(2-methoxyphenyl)cyclopentyl]amino]methyl]-2-[(4-methyl-1-piperazinyl)methyl]-phenol or the pharmaceutical composition thereof, or their pharmaceutically acceptable salts or solvates as a medicament.

In particular the medicament is suitable for modulating REV-ERBs activity in a subject. According to this aspect, compounds of Formula (I) are suitable for the use in the treatment of pathologies associated with dysfunction of circadian rhythm and with benefit from an inhibition of REV-ERBs activity in tissues/cells with a chronodisruption.

Moreover, the compounds of Formula (I) and their pharmaceutical compositions are suitable for use in the treatment of cancers in which a modified circadian pattern of gene/protein expression occurs, in particular of Erb-B2 positive cancers, more particularly selected from the group consisting of breast cancer, ovary cancer, colon cancer, liver cancer, central nervous system cancer, kidney cancer pancreas cancer and prostate cancer. Preferred Erb-B2 cancer is Erb-B2 positive breast cancer.

Moreover, the compounds of Formula (I) and their pharmaceutical compositions are suitable for use in the treatment of cancers with deletion or mutation of the tumor suppressor p53 gene.

In the following, the present invention shall be illustrated by means of some examples, which are not construed to be viewed as limiting the scope of the invention.

The following abbreviations are hereinafter used in the accompanying examples:
Acetic acid (AcOH), acetonitrile (MeCN), ammonia ($NH_3$), ammonium chloride ($NH_4Cl$), n-butyl lithium (n-BuLi), chloroform ($CHCl_3$), cyclohexane (Cy), diatomaceous earth (Celite), deuterated chloroform ($CDCl_3$), deuterated dimethylsulfoxide (DMSO-$d_6$), deuterium oxide ($D_2O$), dichloromethane (DCM), diethyl ether ($Et_2O$), electrospray (ES), dimethylsulfoxide (DMSO), ethanol (EtOH), ethyl acetate (EtOAc), formaldehyde (HCHO), hydrochloric acid (HCl), lithium aluminium hydride ($LiAlH_4$), lithium hexamethyldisilazane (LHMDS), manganese dioxide ($MnO_2$), mass spectrometry (MS), methanol (MeOH), monopotassium phosphate ($KH_2PO_4$), nuclear magnetic resonance (NMR), palladium on carbon (Pd/C), potassium carbonate ($K_2CO_3$), retention time (Rt), room temperature (rt), tetrahydrofuran (THF), sodium bicarbonate ($NaHCO_3$), sodium hydroxide (NaOH), sodium sulphate ($Na_2SO_4$), sodium triacetoxyborohydride ($NaBH(OAc)_3$), sulfuric acid ($H_2SO_4$), titanium tetraisopropoxide ($Ti(iOPr)_4$), thin layer chromatography (TLC), triethylamine ($Et_3N$), trifluoroacetic acid (TFA).

Chemicals, Materials and Methods

Solvents and reagents were obtained from commercial suppliers and were used without further purification. Automated column chromatography purifications were run using a Teledyne ISCO apparatus (CombiFlash® Rf) with pre-packed silica gel columns of different sizes (from 4 g up to 24 g). Flash column chromatography was performed manually on pre-packed silica cartridges (from 2 g up to 10 g) from Biotage. In both cases, mixtures of increasing polarity of Cy and EtOAc or DCM and MeOH were used as eluents. Preparative TLCs were performed using Macherey-Nagel pre-coated 0.05 mm TLC plates (SIL G-50 UV254). NMR experiments were run on a Bruker Avance III 400 system (400.13 MHz for $^1H$, and 100.62 MHz for $^{13}C$), equipped with a BBI probe and Z-gradients. Spectra were acquired at 300 K, using deuterated dimethylsulfoxide (DMSO-$d_6$), deuterated chloroform ($CDCl_3$) as solvents. Chemical shifts (δ) for 1H and $^{13}C$ spectra are reported in parts per million (ppm) using the residual non-deuterated solvent resonance as the internal standard (for $CDCl_3$: 7.26 ppm, $^1H$ and 77.16 ppm, $^{13}C$; for $D_2O$: 4.79 ppm, $^1H$; for DMSO-$d_6$: 2.50 ppm, 1H; 39.52 ppm, $^{13}C$). Data are reported as follows: chemical shift (sorted in descending order), multiplicity (indicated as: s, singlet; bs, broad singlet; d, doublet; t, triplet; q, quartet; p, pentet; m, multiplet and combinations thereof), coupling constants (J) in Hertz (Hz) and integration. UPLC-MS analyses were run on a Waters ACQUITY UPLC-MS system consisting of a SQD (Single Quadropole Detector) Mass Spectrometer equipped with an Electrospray Ionization interface and a Photodiode Array Detector. PDA range was 210-400 nm. Electrospray ionization in positive and negative mode was applied. UPLC mobile phases were: (A) 10 mM $NH_4OAc$ in $H_2O$, pH 5; (B) 10 mM $NH_4OAc$ in MeCN/$H_2O$ (95:5) pH 5. Analyses were performed with method A below reported. Method A-UPLC (generic): Gradient: 5 to 95% B over 3 min. Flow rate 0.5 mL/min. Temperature 40° C. Pre column: Vanguard BEH C18 (1.7 µm 2.1×5 mm). Column: BEH C18 (1.7 µm 2.1×50 mm). Purifications by preparative HPLC/MS were run on a Waters Autopurification system consisting of a 3100 Single Quadropole Mass Spectrometer equipped with an Electrospray Ionization interface and a 2998 Photodiode Array Detector. HPLC system included a 2747 Sample Manager, 2545 Binary Gradient Module, System Fluidic Organizer and 515 HPLC Pump. PDA range was 210-400 nm. Purifications were performed on a XBridge™ Prep $C_{18}$ OBD column (100×19 mmID, particle size 5 µm) with a XBridge™ Prep C18 (10×19 mmID, particle size 5 µm) Guard Cartridge. Mobile phases were 10 mM $NH_4OAc$ in $H_2O$ at pH 5 adjusted with AcOH (A) and 10 mM $NH_4OAc$ in MeCN/$H_2O$ (95:5) at pH 5.0 (B). Electrospray ionization in positive and negative mode was used.

With the aim of better illustrating the present invention, the syntheses of example compounds reported in Tables 1 and 17 are provided.

The compounds reported in Tables 1 and 17 were synthesized as described below.

General Procedure for the Synthesis of the Amines of Formula IIIa (Scheme 7, Method A)

Step 1

To a solution of IX (1.0 equiv.) in anhydrous THF (0.2 M) at −78° C. under argon atmosphere, a solution of n-BuLi (1.0 equiv., 2.5 M in hexanes) was added dropwise. The reaction mixture was stirred for 1 h at the same temperature, and then 1.0 equiv. of Xa was added dropwise. Stirring was continued until the disappearance of the starting material was noted by TLC analysis. The reaction mixture was then quenched with saturated aqueous $NH_4Cl$ solution and extracted with DCM. The organic layer was washed with brine and dried over $Na_2SO_4$. After evaporation of the solvent, the residue of IIIa' was used in the next step without further purification.

Step 2

To a solution of IIIa' (1.0 equiv.) in anhydrous DCM (0.4 M) sodium azide (2.2 equiv.) at rt under nitrogen atmosphere was added. The suspension was cooled at −5° C. and then a 1:2 mixture of TFA: DCM (8.4 equiv. of TFA) was added dropwise under vigorous stirring over a period of 15 min. The resulting suspension was stirred at 0° C. for additional 1 h. To the cold solution distilled water was then added dropwise, followed by the addition of a mixture of distilled water and aqueous 28% $NH_4OH$ solution (1:1) dropwise (5.0 mL). After 30 min, the reaction mixture was extracted with DCM, and the organic layer was washed with water, 1.0 N $KH_2PO_4$ solution, brine and dried over $Na_2SO_4$. After evaporation of the solvent, the crude of IIIa" was purified by column chromatography eluting with Cy (100%).

Step 3

To a solution of IIIa" (1.0 equiv.) in anhydrous THF (0.3 M) $LiAlH_4$ (1.05 equiv., 2.0 M solution in THF) at 0° C. under nitrogen atmosphere was added. The reaction mixture was stirred at rt for 3 h, and then quenched with 1.0 N NaOH. The reaction mixture was then portioned between $Et_2O$ and 1.0 N HCl solution. The aqueous layer was collected and basified with 28% $NH_4OH$ solution up to pH 8.0, and then extracted with DCM. After evaporation of the solvent, the residue of IIIa was used in the next step without further purification.

General Procedure for the Synthesis of Amines of Formula IIIb (Scheme 7, Method B)

Step 1

To a solution of IX (1.1 equiv.) in anhydrous THF (0.2 M) at −78° C. under argon atmosphere, a solution of n-BuLi (1.0 equiv., 2.5 M in hexanes) was added dropwise. The reaction mixture was stirred for 1 h at the same temperature, and then a solution of Xb (1.0 equiv.) in anhydrous THF (1.0 M) was added. The reaction mixture was stirred at −78° C. for 1 h and then allowed to warm to room temperature. Stirring was continued until the disappearance of the starting material was noted by TLC analysis. The reaction mixture was then quenched with saturated aqueous $NH_4Cl$ solution and extracted with DCM. The organic layer was washed with brine and dried over $Na_2SO_4$. After evaporation of the solvent, the crude of IIIb' was purified by column chromatography eluting with gradient mixture of DCM/MeOH or EtOAc/MeOH.

Step 2

To a stirred solution of IIIb' (1.0 equiv.) in anhydrous MeOH (1.0 M) 4.0 M HCl in dioxane (4.0 equiv.) was added. The reaction mixture was stirred at rt for 45 min, and then diluted with EtOAc (5.0 mL). The organic layer was washed with 1.0 N NaOH (5.0 mL), brine and dried over $Na_2SO_4$. After evaporation of the solvent, the residue of IIIb was used in the next step without further purification.

General Procedure for the Synthesis of Amines of Formula IIIc (Scheme 7, Method C)

Step 1

To a solution of IX (1.1 equiv.) in anhydrous THF (0.2 M) at −78° C. under argon atmosphere, a solution of n-BuLi (1.0 equiv., 2.5 M in hexanes) was added dropwise. The reaction mixture was stirred for 1 h at the same temperature, and then 1.0 equiv. of Xc was added dropwise. The reaction mixture was stirred at −78° C. for 1 h and then allowed to warm to rt. Stirring was continued until the disappearance of the starting material was noted by TLC analysis. The reaction mixture was then quenched with saturated aqueous $NH_4Cl$ solution and extracted with DCM. The organic layer was washed with brine and dried over $Na_2SO_4$. After evaporation of the solvent, the residue of IIIc' was used in the next step without further purification.

Step 2

To a mixture of IIIc' (1.0 equiv.) and chloroacetonitrile (3.5 equiv.) AcOH (1.0 mL) was added, followed by the addition of $H_2SO_4$ (1.0 mL). The reaction mixture was stirred at rt overnight and then diluted with EtOAc (4.0 mL), washed with saturated aqueous $NH_4Cl$ solution and water and dried over $Na_2SO_4$. After evaporation of the solvent, the crude of IIIc" was purified by column chromatography eluting with gradient mixture of solvent DCM/MeOH.

Step 3

To a solution of IIIc" (1.0 equiv.) in EtOH (0.13 M) thiourea (1.1 equiv.) and AcOH (6.0 equiv.) were added. The reaction mixture was heated at 80° C. overnight and then cooled at rt, diluted with EtOAc (4.0 ml), washed with 1.0 M NaOH solution (2.0 mL) and dried over $Na_2SO_4$. After evaporation of the solvent, the residue of IIIc was used in the next step without further purification.

General Procedure for the Synthesis of Aldehydes of Formula IIa (Scheme 4)

A mixture of Va (1.0 equiv.), VI (1.0 equiv.) and HCHO (1.0 equiv., 36% solution in water) in EtOH (0.8 M) was heated at reflux for 2 h, then an additional amount of HCHO (1.0 equiv.) was added. The reaction mixture was stirred at reflux overnight. After evaporation of the solvent, the crude of IIa was purified by column chromatography eluting with gradient mixture of DCM/MeOH or EtOAc/MeOH.

General Procedure for the Synthesis of Aldehydes of Formula IIb (Scheme 5)

Step 1

To a solution of Vb (1.0 equiv.) and VI (1.0 equiv.) in anhydrous DCM (0.4 M), $NaBH(OAc)_3$ (2.0 equiv.) was added at rt and the resulting suspension was stirred at room temperature overnight. The reaction mixture was extracted with DCM (10.0 mL), washed with aqueous 10% $K_2CO_3$ solution and dried over $Na_2SO_4$. After evaporation of the solvent, the residue of IIb' was used in the next step without further purification.

Step 2

To a solution of IIb' (1.0 equiv.) in anhydrous THF (0.2 M) $LiAlH_4$ was carefully added (1.05 equiv., 2.0 M solution in THF) at rt under nitrogen atmosphere. Stirring was continued for 1.5 h at room temperature until the disappearance of the starting material was noted by TLC analysis. The reaction mixture was then quenched with water with formation of precipitate. The reaction mixture was carefully quenched by the addition of 2.0 M HCl (5.0 mL) and then extracted with DCM (3×10.0 mL). After evaporation of the solvent, the residue of IIb" was used in the next step without further purification.

Step 3

To a solution of IIb" (1.0 equiv.) in Et$_2$O (0.22 M), activated MnO$_2$ (6.4 equiv.) was added. The reaction mixture was stirred at rt overnight and then filtered through a pad of Celite and washed with DCM (3×15.0 mL). After evaporation of the solvent, the residue of IIb was used in the next step without further purification.

General Procedure for the Synthesis of Aldehydes of Formula IIc (Scheme 6)

Step 1

To a stirred solution of compound VII (1.0 equiv.) in dry toluene (0.2 M) triphenylphosphine (1.0 equiv.) was added. The resulting mixture reaction was stirred at 120° C. overnight, after which time a white precipitate had formed. The reaction was cooled at rt and then was collected the solid by filtration. The solid was washed with minimum amount of cold toluene to afford the compound IIc' as white solid, which was used in the next step without further purification, Step 2

To a solution of IIc' (1.0 equiv.) in anhydrous THF (0.16 M) at −78° C. under argon atmosphere, a solution of LHMDS (5.0 equiv., 1.0 M in THF) was added dropwise. The reaction mixture was stirred for 15 min at the same temperature, and then 1.0 equiv. of VIII was added dropwise. The mixture reaction was stirred at rt for 3 h. Then the solvent was evaporated under reduce pressure and the residue was dissolved in DCM (6.0 mL) and was washed twice with water. The resulted organic phase was dried over Na$_2$SO$_4$. After evaporation of the solvent, the crude of IIc" was purified by column chromatography eluting with gradient mixture of solvent Cy/EtOAc.

Step 3

To a stirred suspension of IIc" (1.0 equiv.) and 10% Pd—C (0.1 equiv.) in MeOH (0.05 M) neat triethylsilane (10.0 equiv.) was added dropwise by the use of a pressure-equalizing dropping funnel under nitrogen atmosphere. After 15 min, the reaction mixture was filtered through a pad of Celite and the solvent was removed under reduce pressure affording the intermediate IIc'" which was used in the next step without further purification.

Step 4

To a solution of 11'" (1.0 equiv.) in anhydrous THF (0.2 M) LiAlH$_4$ was carefully added (1.05 equiv., 2.0 M solution in THF) at rt under nitrogen atmosphere. Stirring was continued for 1.5 h at rt until the disappearance of the starting material was noted by TLC analysis. The reaction mixture was then quenched with water with the formation of precipitate. The reaction mixture was carefully quenched by the addition of 2.0 M HCl (5.0 mL) and then extracted with DCM (3×10.0 mL). After evaporation of the solvent, the residue of IIc"" was used in the next step without further purification.

Step 5

To a solution of IIc"" (1.0 equiv.) in Et$_2$O (0.22 M), activated MnO$_2$ (6.4 equiv.) was added. The reaction mixture was stirred at rt overnight and then filtered through a pad of Celite and washed with DCM (3×15.0 mL). After evaporation of the solvent, the residue of IIb was used in the next step without further purification.

General Procedure for the Synthesis of N-Tert-Butylsulfinyl Ketimines of Formula Xb (Scheme 8)

To a solution of Xa (1.2 equiv.) in THF (0.5 M) Ti(OiPr)$_4$ (2.0 equiv.) is added under nitrogen atmosphere followed by the addition of tert-butanesulfinamide (1.0 equiv.). The reaction mixture was stirred for 2 h, poured into a saturated aqueous NaHCO$_3$ solution (4.0 mL) under vigorous stirring and then immediately filtered through a pad of Celite and washed with EtOAc. The two phases are separated and the aqueous layer is extracted with EtOAc (3×8.0 mL). The combined organic layer is dried over Na$_2$SO$_4$. After evaporation of the solvent, the crude of Xb was purified by column chromatography eluting with gradient mixture of DCM/MeOH and stored into a container at −20° C. until further use.

General Procedure for the Synthesis of Amines of Formula Ia (Scheme 1)

A mixture of II (1.0 equiv.) and III (1.0 equiv.) in anhydrous DCM (0.06 M) was stirred for 10 min at rt and then NaBH(OAc)$_3$ (2.0 equiv.) was added. Stirring was continued at rt overnight. The reaction mixture was diluted with DCM (4.0 mL), washed with aqueous 10% K$_2$CO$_3$ solution and dried over Na$_2$SO$_4$. After evaporation of the solvent, the crude of Ia was purified by column chromatography eluting with gradient mixture of DCM/MeOH, DCM/MeOH/Et$_3$N, DCM/MeOH/NH$_3$ or Cy/EtOAc.

General Procedure for the Synthesis of Amines of Formula Ib (Scheme 3)

A mixture of II (1.0 equiv.) and III (1.0 equiv.) in anhydrous DCM (0.06 M) was stirred for 10 min at rt and then NaBH(OAc)$_3$ (2.0 equiv.) was added. Stirring was continued overnight at rt, then IV (1.1 equiv.) was added followed by an additional amount of NaBH(OAc)$_3$ (2.0 equiv.). Stirring was continued until the disappearance of the starting material was noted by TLC analysis. The reaction mixture was then quenched with aqueous 10% K$_2$CO$_3$ solution and the two phases were separated. The organic layer was dried over Na$_2$SO$_4$. After evaporation of the solvent, the crude of Ib was purified by column chromatography eluting with DCM/MeOH.

Tables of Intermediates of Formula IIIa (Scheme 7, Method A)

Alcohol intermediates of Formula IIIa' (Scheme 7, Method A, step 1) and their physico-chemical properties are described in Tables 2 and 18.

Azide intermediates of Formula IIIa" (Scheme 7, Method A, step 2) and their physico-chemical properties are described in Tables 3 and 19.

Amine intermediates of Formula IIIa (Scheme 7, Method A, step 3) and their physico-chemical properties are described in Tables 4 and 20 (INTERMEDIATE 1, 2, 3, 19, 20, 21, 22, 23, 24).

Tables of Intermediates of Formula IIIb (Scheme 7, Method B)

tert-Butylsulfinamide intermediates of Formula IIIb' (Scheme 7, Method B, step 1) and their physico-chemical properties are described in Table 5.

Amine intermediates of Formula IIIb (Scheme 7, Method B, step 2) and their physico-chemical properties are described in Table 6 (INTERMEDIATE 4, 5, 6).

Tables of Intermediates of Formula IIIb (Scheme 7, Method C)

Chloroacetamides intermediates of Formula IIIc' (Scheme 7, Method C, step 1) and their physico-chemical properties are described in Table 7.

Amine intermediates of formula IIIc (Scheme 6, Method C, step 2) and their physico-chemical properties are described in Table 8 (INTERMEDIATE 7).

Preparation of 4-Hydroxy-3-[(4-methylpiperazin-1-yl)methyl]benzaldehyde (Intermediate 8, scheme 4)

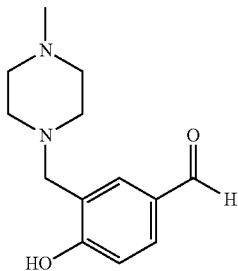 [SMILES: CN1CCN(Cc2cc(C=O)ccc2O)CC1]

Intermediate 8 was prepared according to the general procedure for the synthesis of aldehydes of Formula IIa using 4-hydroxybenzaldehyde (1.0 g, 8.19 mmol), N-methyl piperazine (664.0 µL, 8.19 mmol) and HCHO (1.8 mL, 16.34 mmol) in EtOH (10.0 mL). The crude was purified by column chromatography (DCM/20% MeOH in DCM, from 100:0 up to 50:50) to afford the title compound as a white solid (1.1 g, 57%). UPLC-MS (method generic) Rt 1.14 min; MS (ES) $C_{13}H_{18}N_2O_2$ requires m/z 234, found 235 [M+H]$^+$. $^1$H NMR (400 MHz, DMSO-d$_6$) δ 9.79 (s, 1H), 7.73-7.61 (m, 2H), 6.95-6.85 (m, 1H), 3.71 (s, 2H), 2.45-2.26 (bs, 8H), 2.18 (s, 3H).

Preparation of 4-Hydroxy-3-(1-piperidylmethyl)benzaldehyde (Intermediate 9, scheme 4)

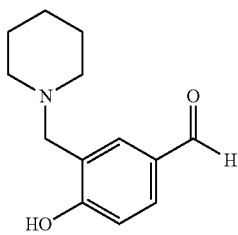 [SMILES: O=Cc1ccc(O)c(CN2CCCCC2)c1]

Intermediate 9 was prepared according to the general procedure for the synthesis of aldehydes of Formula IIa using 4-hydroxybenzaldehyde (500.0 mg, 4.09 mmol), piperidine (404.0 µL, 4.09 mmol) and HCHO (678.0 µL, 8.19 mmol) in EtOH (6.0 mL). The crude was purified by column chromatography (Cy/EtOAc, 95:15 to 30:70) to afford the title compound as colorless oil (600.0 mg, 67%). UPLC-MS (method generic) Rt 1.75 min, MS (ES) $C_{13}H_{17}NO_2$ requires m/z 219, found 220 [M+H]$^+$. $^1$H-NMR (400 MHz, CDCl$_3$) δ 9.82 (s, 1H), 7.70 (dd, J=8.4, 2.1 Hz, 1H), 7.56 (dt, J=1.9, 0.9 Hz, 1H), 6.91 (d, J=8.3 Hz, 1H), 3.77 (s, 2H), 2.57 (bs, 5H), 1.82-1.27 (m, 5H).

Preparation of 3-[(4-Acetylpiperazin-1-yl)methyl]-4-hydroxy-benzaldehyde (Intermediate 10, scheme 4)

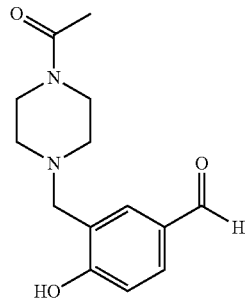 [SMILES: CC(=O)N1CCN(Cc2cc(C=O)ccc2O)CC1]

Intermediate 10 was prepared according to the general procedure for the synthesis of aldehydes of Formula IIa using 4-hydroxybenzaldehyde (250.0 mg, 2.05 mmol), N-acetyl piperazine (315.0 mg, 2.46 mmol) and HCHO (340.0 µL, 4.10 mmol) in 5.0 mL of EtOH. The crude mixture was purified by column chromatography (DCM/MeOH (20% in DCM), from 100:0 up to 50:50) to afford the title compound as a colorless oil (140.0 mg, 26%). UPLC-MS (method generic) Rt 1.27 min, MS (ES) $C_{14}H_{18}N_2O_3$ requires m/z 262, found 263 [M+H]$^+$. $^1$H NMR (400 MHz, DMSO-d$_6$) δ 9.80 (s, 1H), 7.75 (d, J=2.1 Hz, 1H), 7.70 (dd, J=8.3, 2.1 Hz, 1H), 6.96 (d, J=8.3 Hz, 1H), 3.67 (s, 2H), 3.63-2.90 (m, 8H), 1.99 (s, 3H).

Preparation of 4-Hydroxy-3-[(4-phenylpiperazin-1-yl)methyl]benzaldehyde (Intermediate 11, scheme 4)

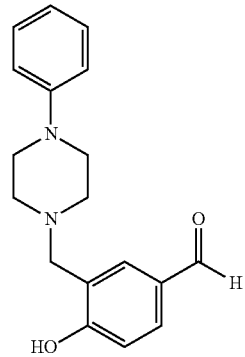 [SMILES: O=Cc1ccc(O)c(CN2CCN(c3ccccc3)CC2)c1]

Intermediate 11 was prepared according to the general procedure for the synthesis of aldehydes of Formula IIa using 4-hydroxybenzaldehyde (2.05 mmol, 250.0 mg), N-phenyl piperazine (2.46 mmol, 375.0 µL) and HCHO (4.10 mmol, 340.0 µL) in 5.0 mL of DCM. The crude mixture was purified by column chromatography (EtOAc/MeOH gradient 100:0 up to 95:5) to afford the title compound as colorless oil (500.0 mg, 82%). UPLC-MS (method generic) Rt 2.42 min, MS (ES) $C_{18}H_{20}N_2O_2$ requires m/z 296, found 297 [M+H]+. 1H NMR (400 MHz, DMSO-$d_6$) δ 9.81 (s, 1H), 7.76 (d, J=2.1 Hz, 1H), 7.71 (dd, J=8.3, 2.1 Hz, 1H), 7.22 (t, J=7.8 Hz, 2H), 6.95 (dd, J=8.3, 5.5 Hz, 3H), 6.79 (t, J=7.2 Hz, 1H), 3.75 (s, 2H), 3.18 (t, J=4.9 Hz, 4H), 2.64 (t, J=4.9 Hz, 4H).

Preparation of 3-[(4-Ethylpiperazin-1-yl)methyl]-4-hydroxy-benzaldehyde (Intermediate 12, scheme 4)

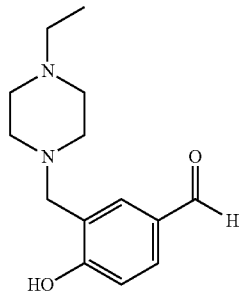 [SMILES: CCN1CCN(Cc2cc(C=O)ccc2O)CC1]

Intermediate 12 was prepared according to the general procedure for the synthesis of aldehydes of Formula IIa using 4-hydroxybenzaldehyde (2.05 mmol, 250.0 mg), N-ethyl piperazine (2.46 mmol, 316.0 µL) and HCHO (4.10 mmol, 340.0 µL) in 5.0 mL of EtOH. The crude mixture was purified by column chromatography (EtOAc/MeOH gradient 100:0 up to 85:15) to afford the title compound as a white solid (265.0 mg, 52%). UPLC-MS (method generic) Rt 1.14 min, MS (ES) $C_{14}H_{20}N_2O_2$ requires m/z 248, found 297 [M+H]+. 1H NMR (400 MHz, DMSO-$d_6$) δ 9.78 (s, 1H), 7.70 (d, J=2.2 Hz, 1H), 7.68 (m, 2H), 6.95-6.82 (m, 1H), 3.71 (s, 2H), 3.65-3.02 (bs, 8H), 2.45-2.15 (q, J=7.2 Hz, 2H), 0.99 (t, J =7.2 Hz, 3H).

Preparation of tert-Butyl 4-[(5-formyl-2-hydroxy-phenyl)methyl]piperazine-1-carboxylate (Intermediate 13, scheme 4)

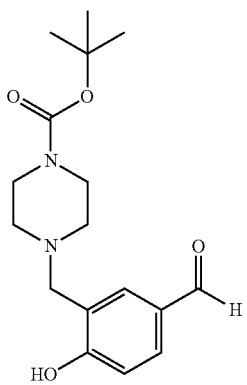 [SMILES: CC(C)(C)OC(=O)N1CCN(Cc2cc(C=O)ccc2O)CC1]

Intermediate 13 was prepared according to the general procedure for the synthesis of aldehydes of Formula IIa using 4-hydroxybenzaldehyde (2.05 mmol, 250.0 mg), N-Boc piperazine (2.46 mmol, 457.0 mg) and HCHO (4.10 mmol, 340.0 µL) in 5.0 mL of EtOH. The crude mixture was purified by column chromatography (Cy/EtOAc gradient 95:5 up to 50:50) to afford the title compound as a white solid (453.0 mg, 70%). UPLC-MS (method generic) Rt 2.37 min, MS (ES) $C_{17}H_{24}N_2O_4$ requires m/z 320, found m/z 320 [M]+. 1H NMR (400 MHz, DMSO-$d_6$) δ 9.80 (s, 1H), 7.79-7.75 (m, 1H), 7.75-7.66 (m, 1H), 7.02-6.80 (m, 2H), 3.65 (s, 2H), 3.50-3.15 (bm, 4H), 3.35 (t, J=5.1 Hz, 2H), 2.41 (t, J=5.1 Hz, 2H), 1.40 (d, J=1.8 Hz, 9H).

Preparation of 3-[(4-Benzylpiperazin-1-yl)methyl]-4-hydroxy-benzaldehyde (Intermediate 14, scheme 4)

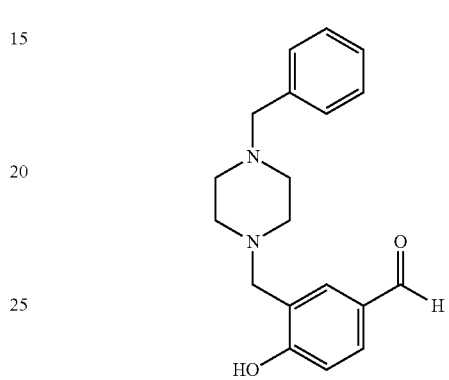

Intermediate 14 was prepared according to the general procedure for the synthesis of aldehydes of Formula IIa using 4-hydroxybenzaldehyde (1.18 mmol, 144.0 mg), N-benzyl piperazine (1.41 mmol, 250.0 mg) and HCHO (2.36 mmol, 196.0 µL) in 5.0 mL of EtOH. The crude mixture was purified by column chromatography (Cy/EtOAc gradient 95:5 up to 0:100) to afford the title compound as a white solid (240.0 mg, 66%). UPLC-MS (method generic) Rt 1.97 min, MS (ES) $C_{19}H_{22}N_2O_2$ requires m/z 310, found m/z 311 [M+H]+. 1H NMR (400 MHz, DMSO-$d_6$) δ 9.78 (s, 1H), 7.73-7.62 (m, 2H), 7.36-7.28 (m, 4H), 7.28-7.22 (m, 1H), 6.94-6.83 (m, 1H), 3.88-3.40 (m, 8H), 3.71 (s, 2H), 3.49 (s, 2H).

Preparation of 4-Hydroxy-3-[(4-isopropylpiperazin-1-yl)methyl]benzaldehyde (Intermediate 15, scheme 4)

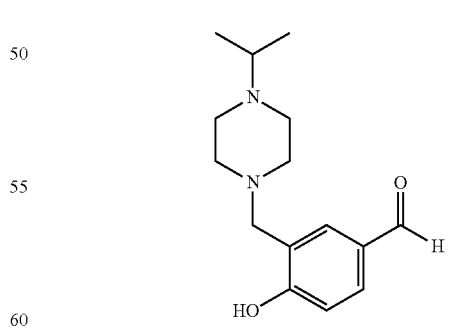

Intermediate 15 was prepared according to the general procedure for the synthesis of aldehydes of Formula IIa using 4-hydroxybenzaldehyde (2.05 mmol, 250.0 mg), N-isopropyl piperazine (2.46 mmol, 351.0 µL) and HCHO (4.10 mmol, 340.0 µL) in 5.0 mL of EtOH. The crude mixture was purified by column chromatography (EtOAc/

MeOH gradient 100:0 up to 85:15) to afford the title compound as yellow oil (310.0 mg, 58%). UPLC-MS (method generic) Rt 1.19 min, MS (ES) $C_{15}H_{22}N_2O_2$ requires m/z 262, found m/z 263 [M–H]$^+$. 1H NMR (400 MHz, DMSO-d$_6$) δ 9.78 (s, 1H), 7.69 (d, J=8.2 Hz, 2H), 6.90 (d, J=8.1 Hz, 1H), 3.71 (s, 2H), 2.64 (dt, J=13.1, 6.5 Hz, 1H), 2.54-2.42 (bm, 8H), 0.97 (d, J=6.5 Hz, 6H).

Tables of Intermediates of Formula IIb (Scheme 5)

Methyl carboxylate arylamine intermediate of Formula IIb' (Scheme 5, step 1) and their physico-chemical properties are described in Tables 9 and 21.

Alcohol intermediate of Formula IIb" (Scheme 5, step 2) and their physico-chemical properties are described in Tables 10 and 22.

Aldehyde intermediates of Formula IIb (Scheme 5, step 3) and their physico-chemical properties are described in Tables 11 and 23 (INTERMEDIATE 16, 17, 25, 26, 27).

Triphenylphosphonium salt of Formula IIc' (Scheme 6, step 1) and its physico-chemical properties are described in Table 12.

Compounds of Formula IIc" (Scheme 6, step 2) and their physico-chemical properties are described in Tables 13 and 24.

Compounds of Formula IIc'" (Scheme 6, step 3) and their physico-chemical properties are described in Tables 14 and 25.

Alcohol intermediates of Formula IIc"" (Scheme 6, step 4) and their physico-chemical properties are described in Tables 15 and 26.

Aldehyde intermediates of Formula IIc (Scheme 6, step 5) and their physico-chemical properties are described in Tables 16 and 27 (INTERMEDIATES 18, 28, 29).

BEST MODE FOR CARRYING OUT THE INVENTION

Preparation of 4-[[[1-(2-Fluorophenyl)cyclopentyl]amino]methyl]-2-[(4-methylpiperazin-1-yl)methyl] phenol trihydrochloride Example 1 CAS number: 1287451-26-6

The title compound was prepared according to the general procedure for the synthesis of compounds of Formula Ia, starting from INTERMEDIATE 1 (100.0 mg, 0.42 mmol), INTERMEDIATE 8 (75.0 mg, 0.42 mmol) and NaBH(OAc)$_3$ (178.0 mg, 0.84 mmol) in DCM (4.5 mL). The crude was purified by column chromatography [DCM and MeOH/NH$_3$ (19% MeOH and 1% NH$_3$ in DCM), from 95:5 to 100:0] to afford the free base of the title compound as a colorless oil (137.0 mg, 82%). UPLC-MS (method generic): Rt 1.58 min, MS (ES) $C_{24}H_{32}FN_3O$ requires m/z 397, found m/z 398 [M–H]$^+$. The free base (60.0 mg, 0.15 mmol) was then dissolved in DCM (1.5 mL) and 2.0 M HCl solution in Et$_2$O (1.5 mL, 3.0 mmol, 20.0 equiv.) was added observing the formation of precipitate. The excess of solvent was removed under reduce pressure and the resulting solid was triturated with Et$_2$O. The resulting solid was dissolved in a solution of CH$_3$CN/H$_2$O (1:1) and lyophilized, affording the title compound as a white powder. $^1$H NMR (400 MHz, DMSO-d$_6$) δ 12.07 (bs, 1H), 10.71 (bs, 1H), 9.53 (s, 2H), 7.65 (t, J=8.0 Hz, 1H), 7.56-7.47 (m, 1H), 7.41 (s, 1H), 7.37-7.28 (m, 2H), 7.23 (d, J=7.7 Hz, 1H), 6.96 (d, J=8.3 Hz, 1H), 3.73 (t, J=5.6 Hz, 2H), 3.71-3.22 (m, 10H), 2.79 (s, 3H), 2.51 (m, 2H), 2.37 (dt, J=12.4, 5.7 Hz, 2H), 2.02-1.83 (m, 2H), 1.67-1.48 (m, 2H).

Preparation of 4-[[[1-(2-Fluorophenyl)cyclopentyl]amino]methyl]-2-(1-piperidylmethyl)phenol dihydrochloride (Example 2)

The title compound was prepared according to the general procedure for the synthesis of compounds of Formula Ia, starting from INTERMEDIATE 1 (68.0 mg, 0.36 mmol), INTERMEDIATE 9 (80.0 mg, 0.36 mmol) and NaBH(OAc)$_3$ (152.0 mg, 0.72 mmol) in DCM (3.0 mL). The crude was purified by column chromatography [Cy/EtOAc, from 90:10 to 0:100] to afford the free base of the title compound as a colorless oil (45.0 mg, 33%). UPLC-MS (method generic): Rt 1.85 min, MS (ES) $C_{24}H_{31}FN_2O$ requires m/z 382, found m/z 383 [M–H]$^+$. The free base (40.0 mg, 0.10 mmol) was then dissolved in 1.0 mL of DCM and 2.0 M HCl solution in Et$_2$O (1.0 mL, 2.0 mmol, 20.0 equiv.) was added. Evaporation of solvents afforded the title compound as a white powder. $^1$H NMR (400 MHz, DMSO-d$_6$) δ 10.61 (s, 1H), 10.16 (s, 1H), 9.54 (s, 2H), 7.72-7.61 (m, 1H), 7.58-7.45 (m, 2H), 7.38-7.25 (m, 2H), 7.21 (dd, J=8.4, 2.2 Hz, 1H), 6.96 (d, J=8.4 Hz, 1H), 4.13 (d, J=4.4 Hz, 2H), 3.84-3.63 (m, 2H), 3.47-3.18 (m, 4H), 3.03-2.75 (m, 2H), 2.51 (dt, J=3.7, 1.9 Hz, 2H), 2.37 (dd, J=13.2, 6.4 Hz, 2H), 1.92 (d, J=8.2 Hz, 2H), 1.79 (d, J=12.9 Hz, 3H), 1.70-1.49 (m, 3H).

Preparation of 4-[[[1-(2-Fluorophenyl)cyclohexyl]amino]methyl]-2-[(4-methylpiperazin-1-yl)methyl] phenol trihydrochloride (Example 3)

The title compound was prepared according to the general procedure for the synthesis of compounds of Formula Ia, starting from INTERMEDIATE 3 (58.0 mg, 0.42 mmol), INTERMEDIATE 8 (70.0 mg, 0.42 mmol) and NaBH(OAc)$_3$ (177.0 mg, 0.84 mmol) in DCM (3.0 mL). The crude was purified by column chromatography [DCM and MeOH/NH$_3$ (19% MeOH and 1% NH$_3$ in DCM), from 95:5 to 100:0] to afford the free base of the title compound as a colorless oil, (110.0 mg, 63%). UPLC-MS (method generic): Rt 1.67 min, MS (ES) $C_{25}H_{34}FN_3O$ requires m/z 382, found m/z 412 [M–H]$^+$. The free base (76.0 mg, 0.18 mmol) was then dissolved in 1.5 ml and 2.0 M HCl solution in Et$_2$O (1.5 mL, 3.6 mmol, 20.0 equiv.) was added. Evaporation of solvents afforded the title compound as a white powder. $^1$H NMR (400 MHz, DMSO-d$_6$) δ 12.06 (bs, 1H), 10.71 (bs, 1H), 9.51 (s, 2H), 7.78 (t, J=8.1 Hz, 1H), 7.56 (td, J=7.4, 4.1 Hz, 1H), 7.36 (ddd, J=22.0, 14.6, 8.1 Hz, 3H), 7.25 (dd, J=8.6, 2.3 Hz, 1H), 6.97 (d, J=8.3 Hz, 1H), 4.52-3.90 (bm, 4H), 3.80-3.50 (m, 6H), 3.49-3.30 (bm, 2H), 2.84 (dd, J=36.7, 8.2 Hz, 2H), 2.80 (bs, 3H) 2.12 (t, J=12.2 Hz, 2H), 1.77 (d, J=13.1 Hz, 2H), 1.67-1.48 (m, 1H), 1.34-1.05 (m, 3H).

Preparation of 1-(2-Fluorophenyl)-N-[[3-[(4-methylpiperazin-1-yl)methyl]phenyl]methyl]-cyclopentanamine trihydrochloride (Example 4)

The title compound was prepared according to the general procedure for the synthesis of compounds of Formula Ia, starting from INTERMEDIATE 1 (72.0 mq, 0.40 mmnol), INTERMEDIATE 16 (89.0 mg, 0.40 mmol) and NaBH(OAc)$_3$ (144.0 mg, 0.68 mmol) in DCM (3.0 mL). The crude was purified by column chromatography [DCM/MeOH (20% in DCM), from 95:5 to 50:50] to afford the free base of the title compound as a colorless oil, (76.0 mg, 50%). UPLC-MS (method generic): Rt 1.77 min, MS (ES) $C_{24}H_{32}FN_3$ requires m/z 381, found m/z 382 [M–H]$^+$. The free base (50.0 mg, 0.13 mmol) was then dissolved in 0.5 mL of DCM and 2.0 M HCl solution in Et$_2$O (1.2 mL, 2.6 mmol, 20.0 equiv.) was added. Evaporation of solvents afforded the title compound as a white powder. $^1$H NMR (400 MHz, DMSO-d$_6$) δ 12.18 (bs, 2H), 9.74 (bs, 2H), 7.65 (m, 2H), 7.51 (t, J=6.6 Hz, 2H), 7.42 (d, J=8.0 Hz, 2H), 7.36-7.20 (m, 2H), 3.97-3.72 (m, 2H), 3.70-3.11 (m, 10H), 2.80 (s, 3H), 2.58 (dd, J=14.1, 6.9 Hz, 2H), 2.38 (dt, J=12.1, 5.3 Hz, 2H), 1.93 (q, J=7.4, 6.8 Hz, 2H), 1.60 (dt, J=11.1, 5.4 Hz, 2H).

Preparation of 1-(2-Fluorophenyl)-N-[[4-methoxy-3-[(4-methylpiperazin-1-yl)methyl]-phenyl]methyl]cyclopentanamine trihydrochloride (Example 5)

The title compound was prepared according to the general procedure for the synthesis of compounds of Formula Ia, starting from INTERMEDIATE 1 (28.0 mg, 0.15 mmol), INTERMEDIATE 17 (38.0 mg, 0.15 mmol) and NaBH(OAc)$_3$ (64.0 mg, 0.30 mmol) in DCM (3.0 mL). The crude was purified by column chromatography [DCM and MeOH/Et$_3$N (19% MeOH and 1% Et$_3$N in DCM), from 95:5 to 40:60] to afford the title compound as a colorless oil (40 mg, 65%). UPLC-MS (method generic): Rt 1.70 min, MS (ES) C$_{25}$H$_{34}$FN$_3$O requires m/z 411, found m/z 412 [M+H]$^+$. The free base (50.0 mg, 0.12 mmol) was then dissolved in 1.0 mL of DCM and 2.0 M HCl solution in Et$_2$O (1.2 mL, 2.4 mmol, 20.0 equiv.) was added. Evaporation of solvents afforded the title compound as a white powder. $^1$H NMR (400 MHz, DMSO-d$_6$) δ 12.07 (bs, 2H), 9.65 (bs, 2H), 7.66 (t, J=7.8 Hz, 1H), 7.50 (dq, J=10.8, 6.8, 6.3 Hz, 2H), 7.46-7.38 (m, 1H), 7.37-7.26 (m, 2H), 7.07 (d, J=8.4 Hz, 1H), 4.21 (bm, 2H), 3.84 (s, 3H), 3.77 (m, 2H), 3.72 (m, 8H), 2.79 (bs, 3H), 2.60-2.45 (m, 2H), 2.37 (m, 2H), 2.09-1.77 (m, 2H), 1.69-1.41 (m, 2H).

Preparation of 4-[[[1-(2-Fluorophenyl)cyclopentyl]-methyl-amino]methyl]-2-[(4-methylpiperazin-1-yl)methyl]phenol trihydrochloride (Example 6)

The title compound was prepared according to the general procedure for the synthesis of compounds of Formula Ib, starting from INTERMEDIATE 1 (32.0 mg, 0.18 mmol), INTERMEDIATE 8 (42.0 mg, 0.18 mmol), HCHO (240.0 μL, 0.36 mmol) and NaBH(OAc)$_3$ (76.0 mg, 0.36 mmol) in DCM (3.0 mL). The crude was purified by column chromatography [DCM and MeOH/Et$_3$N (19% MeOH and 1% Et$_3$N in DCM), from 95:5 to 40:60] to afford the free base of the title compound as a colorless oil (65.0 mg, 62%). UPLC-MS (method generic): Rt 2.18 min, MS (ES) C$_{25}$H$_{34}$FN$_3$O requires m/z 411, found m/z 412 [M+H]$^+$. The free base (30.0 mg, 0.08 mmol) was then dissolved in 0.5 mL of DCM and 2.0 M HCl solution in Et$_2$O (1.3 mL, 1.6 mmol, 20.0 equiv.) was added. Evaporation of solvents afforded the title compound as a white powder. $^1$H NMR (400 MHz, DMSO-d$_6$) δ 12.36-11.48 (m, 2H), 10.78 (bs, 2H), 7.87 (t, J=7.5 Hz, 1H), 7.70-7.53 (m, 2H), 7.52-7.29 (m, 3H), 7.01 (d, J=8.0 Hz, 1H), 4.63 (d, J=12.3 Hz, 1H), 4.38-4.00 (m, 2H), 3.84-3.23 (m, 8H), 3.18-2.98 (m, 1H), 2.97-2.71 (m, 3H), 2.71-2.57 (m, 3H), 2.52-2.42 (m, 3H), 1.87 (m, 2H), 1.36 (m, 2H).

Preparation of 2-[(4-Methylpiperazin-1-yl)methyl]-4-[[(1-phenylcyclopentyl)amino]methyl]-phenol trihydrochloride (Example 7)

The title compound was prepared according to the general procedure for the synthesis of compounds of Formula Ia, starting from INTERMEDIATE 2 (40.0 mg, 0.24 mmol), INTERMEDIATE 8 (58.0 mg, 0.24 mmol) and NaBH(OAc)$_3$ (102.0 mg, 0.48 mmol) in DCM (3.0 mL). The crude was purified by column chromatography [DCM/MeOH (20% MeOH in DCM), from 95:5 to 40:60] to afford the free base of the title compound as a colorless oil (57.0 mg, 63%). UPLC-MS (method generic): Rt 1.51 min, MS (ES) C$_{24}$H$_{33}$FN$_3$O requires m/z 379, found m/z 380 [M+H]$^+$. The free base (57.0 mg, 0.15 mmol) was then dissolved in 0.5 mL of DCM and 2.0 M HCl solution in Et$_2$O (1.5 mL, 3.0 mmol, 20.0 equiv.) was added. Evaporation of solvents afforded the title compound as a white powder. $^1$H NMR (400 MHz, DMSO-d$_6$) δ 12.32-11.61 (bs, 1H), 10.72 (bs, 1H), 9.81 (bs, 2H), 7.77 (m, 3H), 7.51 (t, J=7.2 Hz, 2H), 7.47-7.33 (m, 2H), 7.24 (d, J=8.1 Hz, 1H), 6.97 (d, J=8.0 Hz, 1H), 3.80-3.13 (m, 12H), 2.79 (s, 3H), 2.45-2.30 (m, 4H), 1.85 (m, 2H), 1.65-1.37 (m, 2H).

Preparation of 1-[4-[[5-[[[1-(2-Fluorophenyl) cyclopentyl]amino]methyl]-2-hydroxyphenyl]-methyl]piperazin-1-yl]ethanone dihydrochloride (Example 8)

The title compound was prepared according to the general procedure for the synthesis of compounds of Formula Ia, starting from INTERMEDIATE 1 (41.0 mg, 0.23 mmol), INTERMEDIATE 10 (60.0 mg, 0.23 mmol) and NaBH(OAc)$_3$ (81.0 mg, 0.36 mmol) in DCM (3.0 mL). The crude was purified by column chromatography (EtOAc/Cy/Et$_3$N, 4:1:0.1) to afford the free base of the title compound as a colorless oil (50.0 mg, 50%). UPLC-MS (method generic): Rt 1.88 min, MS (ES) C$_{24}$H$_{33}$FN$_3$O requires m/z 425, found m/z 426 [M+H]$^+$. The free base (36.0 mg, 0.08 mmol) was then dissolved in 0.5 mL of DCM and 2.0 M HCl solution in Et$_2$O (1.0 mL, 1.6 mmol, 20.0 equiv.) was added. Evaporation of solvents afforded the title compound as a white powder. $^1$H NMR (400 MHz, DMSO-d$_6$) δ 10.83 (d, J=11.3 Hz, 1H), 10.63 (s, 1H), 9.73-9.22 (m, 2H), 7.64 (t, J=7.9 Hz, 1H), 7.59-7.40 (m, 2H), 7.41-7.25 (m, 2H), 7.21 (d, J=8.1 Hz, 1H), 6.94 (d, J=8.2 Hz, 1H), 4.40 (d, J=13.7 Hz, 1H), 4.21 (bs, 2H), 3.97 (d, J=13.1 Hz, 1H), 3.73 (t, J=5.3 Hz, 2H), 3.55 (m, 1H), 3.45-3.20 (m, 2H), 3.21-2.97 (m, 2H), 2.88 (m, 1H), 2.54-2.46 (m, 2H), 2.42-2.30 (m, 2H), 2.03 (s, 3H), 1.96-1.85 (m, 2H), 1.63-1.50 (m, 2H).

Preparation of 4-[[[1-(2-Fluorophenyl)cyclopentyl]amino]methyl]-2-[(4-phenylpiperazin-1-yl)methyl]phenol trihydrochloride (Example 9)

The title compound was prepared according to the general procedure for the synthesis of compounds of Formula Ia, starting from INTERMEDIATE 1 (45.0 mg, 0.25 mmol), INTERMEDIATE 11 (74.1 mg, 0.25 mmol) and NaBH(OAc)$_3$ (106.0 mg, 0.50 mmol) in DCM (3.0 mL). The crude was purified by column chromatography (Cy/EtOAc, from 100:0 to 60:40) to afford the free base of the title compound as a colorless oil (65.0 mg, 57%). UPLC-MS (method generic): Rt 3.24 min, MS (ES) C$_{29}$H$_{34}$FN$_3$O requires m/z 459, found m/z 460 [M+H]$^+$. The free base (60.0 mg, 0.13 mmol) was then dissolved in 0.5 mL of DCM and 2.0 M HCl solution in Et$_2$O (1.3 mL, 2.6 mmol, 20.0 equiv.) was added. Evaporation of solvents afforded the title compound as a white powder. $^1$H NMR (400 MHz, DMSO-d$_6$) δ 10.71 (m, 2H), 9.53 (bs, 2H), 7.65 (t, J=7.9 Hz, 1H), 7.52 (m, 2H), 7.38-7.19 (m, 5H), 6.98 (m, 3H), 6.86 (t, J=7.2 Hz, 1H), 4.27

(bs, 2H), 3.89-3.65 (m, 4H), 3.44 (d, J=9.4 Hz, 2H), 3.17 (m, 4H), 2.55-2.50 (m, 2H), 2.41-2.34 (m, 2H), 2.00-1.85 (m, 2H), 1.67-1.53 (m, 2H).

Preparation of 2-[(4-Ethylpiperazin-1-yl)methyl]-4-[[[1-(2-fluorophenyl)cyclopentyl]amino]-methyl]phenol trihydrochloride (Example 10)

The title compound was prepared according to the general procedure for the synthesis of compounds of Formula Ia, starting from INTERMEDIATE 1 (45.0 mg, 0.25 mmol) and INTERMEDIATE 12 (62.0 mg, 0.25 mmol) and NaBH(OAc)$_3$ (106.0 mg, 0.50 mmol) in DCM (3.0 mL). The crude was purified by column chromatography [DCM and MeOH/Et$_3$N (19% MeOH and 1% Et$_3$N in DCM), from 95:5 to 40:60] to afford the free base of the title compound as a colorless oil (57.0 mg, 56%). UPLC-MS (method generic): Rt 1.63 min, MS (ES) C25H$_{34}$FN$_3$O requires m/z 411, found m/z 412 [M+Hz]$^+$. The free base (57.0 mg, 0.14 mmol) was then dissolved in 0.5 mL of DCM and 2.0 M HCl solution in Et$_2$O (1.4 mL, 2.8 mmol, 20.0 equiv.) was added. Evaporation of solvents afforded the title compound as a white powder. $^1$H NMR (400 MHz, DMSO-d$_6$) δ 11.99 (bs, 1H), 10.74 (bs, 1H), 9.50 (bs, 2H), 7.65 (t, J=8.0 Hz, 1H), 7.51 (m, 1H), 7.44 (m, 1H), 7.38-7.27 (m, 2H), 7.24 (d, J=8.2 Hz, 1H), 6.96 (d, J=8.3 Hz, 1H), 4.38-4.10 (m, 2H), 3.73 (bs, 2H), 3.65 (s, 8H), 3.28-2.96 (m, 2H), 2.55-2.50 (m, 2H), 2.43-2.31 (m, 2H), 1.96-1.85 (m, 2H), 1.66-1.50 (m, 2H), 1.26 (t, J=7.0 Hz, 3H).

Preparation of 4-[[[1-(2-Fluorophenyl)cyclopentyl]amino]methyl]-2-(piperazin-1-ylmethyl)-phenol (Example 11)

The title compound was prepared according to the general procedure for the synthesis of compounds of Formula Ia, starting from INTERMEDIATE 1 (66.0 mg, 0.36 mmol), INTERMEDIATE 13 (118.0 mg, 0.36 mmol) and NaBH(OAc)$_3$ (152.0 mg, 0.72 mmol) in DCM (4.0 mL). The residue was dissolved in dioxane (1.0 mL) and HCl 4.0 M solution in dioxane (0.5 mL) was added and the reaction mixture stirred at rt for 1 h. After evaporation of the solvents, the crude was purified by preparative HPLC/MS run on a Water autopurification system on a XBridge™ Prep C$_{18}$ OBD column (100×19 mmID, particle size 5 μm) with a XBridge™ Prep C18 (10×19 mmID, particle size 5 μm) Guard Cartridge using a isocratic method with NH$_4$OAc 10 mM in CH$_3$CN/water 95:5 at pH 5 as mobile phase to afford the title compound as white solid. UPLC-MS (method generic): Rt 1.52 min, MS (ES) C$_{23}$H$_{30}$FN$_3$O requires m/z 383, found m/z 384 [M+H]$^+$. $^1$H NMR (400 MHz, DMSO-d$_6$) δ 7.41 (td, J=8.2, 1.9 Hz, 1H), 7.30 (tdd, J=7.5, 5.2, 1.8 Hz, 1H), 7.21-7.08 (m, 2H), 6.92-6.78 (m, 2H), 6.59 (d, J=8.1 Hz, 2H), 3.53 (s, 2H), 3.17 (bs, 2H), 2.69 (m, 4H), 2.35 (m, 4H), 2.20-2.07 (m, 2H), 1.88-1.74 (m, 2H), 1.70-1.55 (m, 4H), 1.36-1.16 (m, 2H).

Preparation of 2-[(4-Benzylpiperazin-1-yl)methyl]-4-[[[1-(2-fluorophenyl)cyclopentyl]amino]-methyl]phenol trihydrochloride (Example 12)

The title compound was prepared according to the general procedure for the synthesis of compounds of Formula Ia, starting from INTERMEDIATE 1 (78.0 mg, 0.44 mmol), INTERMEDIATE 14 (136.0 mg, 0.44 mmol) and NaBH(OAc)$_3$ (186.0 mg, 0.88 mmol) in DCM (6.0 mL). The crude was purified by column chromatography [DCM/MeOH (20% MeOH in DCM), from 95:5 to 60:40] to afford the free base of the title compound as a white solid (64.0 mg, 31%). UPLC-MS (method generic): Rt 2.84 min, MS (ES) C$_{30}$H$_{36}$FN$_3$O requires m/z 473, found m/z 474 [M+H]$^+$. The free base (60.0 mg, 0.12 mmol) was then dissolved in 0.5 mL of dioxane and 4.0 M HCl solution in dioxane (0.6 mL, 2.4 mmol, 20.0 equiv.) was added. Evaporation of solvents afforded the title compound as a white powder. $^1$H NMR (400 MHz, DMSO-d$_6$) δ 12.22 (bs, 1H), 10.68 (bs, 1H), 9.47 (bs, 2H), 7.73-7.57 (m, 3H), 7.57-7.48 (m, 1H), 7.48-7.36 (m, 4H), 7.37-7.27 (m, 2H), 7.23 (dd, J=8.5, 2.2 Hz, 1H), 6.94 (d, J=8.4 Hz, 1H), 4.52-4.03 (m, 2H), 3.78-3.67 (m, 2H), 3.67-3.13 (m, 10H), 2.55-2.50 (m, 2H), 2.42-2.31 (m, 2H), 2.02-1.80 (m, 2H), 1.65-1.50 (m, 2H).

Preparation of 4-[[[1-(2-Fluorophenyl)cyclopentyl]amino]methyl]-2-[(4-isopropylpiperazin-1-yl)methyl]phenol trihydrochloride (Example 13)

The title compound was prepared according to the general procedure for the synthesis of compounds of Formula Ia, starting from INTERMEDIATE 1 (42.0 mg, 0.26 mmol), INTERMEDIATE 15 (70.0 mg, 0.26 mmol) and NaBH(OAc)$_3$ (110.0 mg, 0.52 mmol) in DCM (3.0 mL). The crude was purified by column chromatography [DCM/MeOH (20% MeOH in DCM), from 95:5 to 60:40] to afford the free base of the title compound as a colorless oil (81.0 mg, 74%). UPLC-MS (method generic): Rt 1.80 min, MS (ES) C$_{26}$H$_{36}$FN$_3$O requires m/z 425, found m/z 426 [M+H]$^+$. The free base (81.0 mg, 0.20 mmol) was then dissolved in 0.5 mL of DCM and 2.0 M HCl solution in Et$_2$O (2.0 mL, 4.0 mmol, 20.0 equiv.) was added. Evaporation of solvents afforded the title compound as a white powder. $^1$H NMR (400 MHz, D$_2$O) δ 7.46-7.34 (bs, 2H), 7.21 (t, J=7.6 Hz, 1H), 7.17-7.05 (m, 2H), 7.03 (d, J=2.2 Hz, 1H), 6.83 (d, J=8.4 Hz, 1H), 4.26 (s, 2H), 3.89 (s, 2H), 3.73-3.25 (m, 10H), 2.43 (dt, J=12.0, 5.6 Hz, 2H), 2.17 (dt, J=14.4, 7.3 Hz, 2H), 1.89-1.72 (m, 2H), 1.63 (dt, J=13.8, 5.2 Hz, 2H), 1.27 (d, J=6.6 Hz, 6H).

Preparation of 4-[[[1-(2-Fluorophenyl)tetrahydropyran-4-yl]amino]methyl]-2-[(4-methyl-piperazin-1-yl)methyl]phenol trihydrochloride (Example 15)

The title compound was prepared according to the general procedure for the synthesis of compounds of Formula Ia, starting from INTERMEDIATE 4 (45.0 mg, 0.23 mmol), INTERMEDIATE 8 (54.0 mg, 0.23 mmol) and NaBH(OAc)$_3$ (97.0 mg, 0.46 mmol) in DCM (3.0 mL). The crude was purified by column chromatography (DCM/MeOH 95:5) to afford the free base of title compound as a colorless oil (38.0 mg, 50%). UPLC-MS (method generic): Rt 1.56 min, MS (ES) C$_{24}$H$_{32}$FN$_3$O$_2$ requires m/z 413, found m/z 414 [M+H]+. The free base (35.0 mg, 0.08 mmol) was then dissolved in 0.5 mL of DCM and 2.0 M HCl solution in Et$_2$O (0.8 mL, 1.6 mmol, 20.0 equiv.) was added. Evaporation of solvents afforded the title compound as a white powder. $^1$H NMR (400 MHz, D$_2$O) δ 7.50 (dt, J=19.0, 7.6 Hz, 2H), 7.29 (t, J=7.6 Hz, 1H), 7.23-7.07 (m, 2H), 7.04 (d, J=2.2 Hz, 1H), 6.83 (d, J=8.4 Hz, 1H), 4.27 (s, 2H), 4.04-3.90 (m, 2H), 3.85 (s, 2H), 3.67-3.25 (m, 10H), 2.90 (s, 3H), 2.78 (d, J=13.6 Hz, 2H), 2.12 (td, J=12.9, 4.4 Hz, 2H).

Preparation of 4-(2-fluorophenyl)-4-[[4-hydroxy-3-[(4-methylpiperazin-1-yl)methyl]phenyl]-methylamino]cyclohexanone trihydrochloride (Example 16)

The title compound was prepared according to the general procedure for the synthesis of compounds of Formula Ia, starting from INTERMEDIATE 5 (45.0 mg, 0.22 mmol), INTERMEDIATE 8 (51.0 mg, 0.22 mmol) and NaBH(OAc)$_3$ (97.0 mg, 0.46 mmol) in DCM (3.0 mL). The crude was purified by column chromatography [DCM/MeOH (20% MeOH in DCM), from 95:5 to 60:40] to afford the free base of title compound a colorless oil, (44.0 mg, 46%). UPLC-MS (method generic): Rt 1.84 min, MS (ES) C$_{25}$H$_{32}$FN$_3$O$_2$ requires m/z 425, found m/z 426 [M+H]$^+$. The free base (35.0 mg, 0.08 mmol) was then dissolved in 0.5 mL of DCM and 2.0 M HCl solution in Et$_2$O (0.8 mL, 1.6 mmol, 20.0 equiv.) was added. Evaporation of solvents afforded the title compound as a white powder. $^1$H NMR (400 MHz, D$_2$O) δ 7.64 (td, J=8.4, 1.6 Hz, 1H), 7.60-7.47 (m, 1H), 7.34 (ddd, J=9.2, 6.3, 1.4 Hz, 1H), 7.25-7.05 (m, 3H), 6.89 (d, J=8.4 Hz, 1H), 4.33 (s, 2H), 4.00 (bs, 2H), 3.77-3.37 (m, 8H), 3.12 (bs, 1H), 2.97 (s, 3H), 2.82 (d, J=13.5 Hz, 1H), 2.60-2.35 (m, 4H), 2.25-2.06 (m, 1H), 1.92 (d, J=14.2 Hz, 1H), 1.63 (t, J=13.4 Hz, 1H).

Preparation of 4-[[[4,4-difluoro-1-(2-fluorophenyl)cyclohexyl]amino]methyl]-2-[(4-methyl-piperazin-1-yl)methyl]phenol trihydrochloride (Example 17)

The title compound was prepared according to the general procedure for the synthesis of compounds of Formula Ia, starting from INTERMEDIATE 7 (53.0 mg, 0.23 mmol), INTERMEDIATE 8 (54.0 mg, 0.23 mmol) and NaBH(OAc)$_3$ (97.0 mg, 0.46 mmol) in DCM (3.0 mL). The crude was purified by column chromatography [DCM/MeOH (20% MeOH in DCM), from 100:0 to 60:40] to afford the free base of title compound a colorless oil, (53.0 mg, 50%). UPLC-MS (method generic): Rt 2.49 min, MS (ES) C$_{25}$H$_{32}$F$_3$N$_3$O requires m/z 447, found m/z 448 [M+H]$^+$. The free base (50.0 mg, 0.11 mmol) was then dissolved in 0.5 mL of dioxane and 4.0 M HCl solution in Et$_2$O (1.0 mL, 2.2 mmol, 20.0 equiv.) was added. Evaporation of solvents afforded the title compound as a white powder. $^1$H NMR (400 MHz, DMSO-d$_6$) δ 11.98 (bs, 1H), 10.81 (bs, 1H), 9.86 (s, 2H), 7.85 (t, J=8.1 Hz, 1H), 7.62 (ddt, J=8.3, 5.4, 3.2 Hz, 1H), 7.49-7.33 (m, 3H), 7.27 (dd, J=8.5, 2.3 Hz, 1H), 6.97 (d, J=8.4 Hz, 1H), 4.30-4.05 (m, 2H), 3.72 (bs, 2H), 3.70-3.24 (m, 8H), 2.98 (d, J=12.5 Hz, 2H), 2.68 (bs, 3H), 2.45 (d, J=12.1 Hz, 2H), 2.35-2.13 (m, 2H), 1.80-1.51 (m, 2H).

Preparation of 1-(2-fluorophenyl)-N-[[3-[1-methyl-4-piperidyl)methyl]phenyl]methyl]cyclopentanamine dihydrochloride (Example 18)

The title compound was prepared according to the general procedure for the synthesis of compounds of Formula Ia, starting from INTERMEDIATE 1 (50.0 mg, 0.23 mmol), INTERMEDIATE 18 (60.0 mg, 0.23 mmol) and NaBH(OAc)$_3$ (97.0 mg, 0.46 mmol) in DCM (3.0 mL). The crude was purified by column chromatography [DCM/MeOH (20% MeOH in DCM), from 90:10 to 0:100] to afford the free base of title compound a colorless oil, (60.0 mg, 57%). UPLC-MS (method generic): Rt 2.04 min, MS (ES) C$_{25}$H$_{33}$FN$_2$ requires m/z 380, found m/z 381 [M+H]+. The free base (30.0 mg, 0.08 mmol) was then dissolved in 0.5 mL of dioxane and 4.0 M HCl solution in Et$_2$O (0.4 mL, 1.6 mmol, 20.0 equiv.) was added. Evaporation of solvents afforded the title compound as a white powder. $^1$H NMR (400 MHz, DMSO-d$_6$) δ 10.49 (bs, 1H), 9.52 (bs, 2H), 7.62 (td, J=8.5, 8.1, 1.9 Hz, 1H), 7.56-7.48 (m, 1H), 7.42-7.23 (m, 3H), 7.21-7.14 (m, 2H), 7.11 (s, 1H), 3.83 (t, J=5.1 Hz, 2H), 3.42-3.42 (m, 2H), 2.94-2.73 (m, 2H), 2.68 (d, J=4.8 Hz, 2H), 2.56-2.45 (m, 5H), 2.37 (dt, J=12.4, 5.6 Hz, 2H), 1.92 (td, J=11.9, 9.5, 5.5 Hz, 2H), 1.80-1.64 (m, 3H), 1.64-1.41 (m, 4H).

Preparation of 1-(2-fluorophenyl)-N-methyl-N-[[3-[(1-methyl-4-piperidyl)methyl]phenyl]methyl]cyclopentanamine dihydrochloride (Example 19)

The title compound was prepared according to the general procedure for the synthesis of compounds of Formula Ib, starting from INTERMEDIATE 1 (15.0 mg, 0.08 mmol), INTERMEDIATE 18 (18.0 mg, 0.08 mmol), HCHO (20.0 μL, 0.8 mmol) and NaBH(OAc)$_3$ (33.0 mg, 0.16 mmol) in DCM (3.0 mL). The crude was purified by column chromatography using Biotage column SI 2 g using as eluent DCM/MeOH 90:10 to afford the free base of the title compound as a colorless oil (20.0 mg, 65%). UPLC-MS (method generic): Rt 2.90 min, MS (ES) C$_{26}$H$_{35}$FN$_2$ requires m/z 394, found m/z 395 [M+H]+. The free base (20.0 mg, 0.05 mmol) was then dissolved in 0.5 mL of dioxane and 4.0 M HCl solution in Et$_2$O (0.250 mL, 1.0 mmol, 20.0 equiv.) was added. Evaporation of solvents afforded the title compound as a white powder. $^1$H NMR (400 MHz, DMSO-d$_6$) δ 10.84 (bs, 1H), 10.54 (bs, 1H), 7.94-7.79 (m, 1H), 7.65 (q, J=7.2, 6.8 Hz, 1H), 7.46-7.37 (m, 4H), 7.32 (t, J=7.5 Hz, 1H), 7.24 (d, J=7.5 Hz, 1H), 4.76-4.60 (m, 1H), 3.60-3.45 (m, 2H), 3.37-3.25 (m, 2H), 3.17-3.04 (m, 2H), 2.88-2.68 (m, 3H), 2.75-2.61 (m, 5H), 2.51 (s, 3H), 2.03-1.61 (m, 5H), 1.60-1.14 (m, 4H).

Preparation of 4-[[[1-Benzyl-4-(2-fluorophenyl)-4-piperidyl]amino]methyl]-2-[(4-methylpiperazin-1-yl)methyl]phenol tetrahydrochloride (Example 20)

The title compound was prepared according to the general procedure for the synthesis of compounds of Formula Ia, starting from INTERMEDIATE 6 (25.0 mg, 0.09 mmol), INTERMEDIATE 8 (21.0 mg, 0.09 mmol) and NaBH(OAc)$_3$ (38.0 mg, 0.18 mmol) in DCM (3.0 mL). The crude was purified by column chromatography [DCM/MeOH (20% MeOH in DCM), from 90:10 to 0:100] to afford the free base of title compound as colorless oil, (28.0 mg, 64%). UPLC-MS (method generic): Rt 1.84 min, MS (ES) C$_{31}$H$_{39}$FN$_4$O requires m/z 502, found m/z 503 [M+H]+. The free base (28.0 mg, 0.05 mmol) was then dissolved in 0.5 mL of dioxane and 4.0 M HCl solution in Et$_2$O (0.370 mL, 1.5 mmol, 30.0 equiv.) was added. Evaporation of solvents afforded the title compound as a white powder. $^1$H NMR (400 MHz, DMSO-d$_6$) δ 11.96 (bs, 1H), 11.38 (bs, 1H), 10.74 (bs, 1H), 10.08 (bs, 2H), 7.87 (t, J=8.3 Hz, 1H), 7.81-7.70 (m, 1H), 7.70-7.53 (m, 3H), 7.52-7.32 (m, 6H), 7.31-7.13 (m, 2H), 6.97 (d, J=8.4 Hz, 1H), 4.60-4.50 (m, 1H), 4.32-3.97 (m, 3H), 3.85-3.35 (m, 13H), 3.24-3.04 (m, 2H), 2.99-2.56 (m, 6H).

Preparation of 1-(2-Fluorophenyl)-N-[[3-(1-piperidylmethyl)phenyl]methyl]cyclopentanamine dihydrochloride (Example 21)

The title compound was prepared according to the general procedure for the synthesis of compounds of Formula Ia, starting from INTERMEDIATE 1 (50.0 mg, 0.24 mmol), INTERMEDIATE 25 (44.0 mg, 0.24 mmol) and NaBH(OAc)$_3$ (102.0 mg, 0.48 mmol) in DCM (3.0 mL). The crude was purified by column chromatography [DCM/MeOH, from 100:0 to 0:100] to afford the free base of the title compound as a colorless oil (50.0 mg, 57%). UPLC-MS (method generic A): Rt 2.12 min, MS (ES) C$_{24}$H$_{31}$FN$_2$ requires m/z 366, found m/z 367 [M+H]$^+$. The free base (50.0 mg, 0.14 mmol) was then dissolved in 0.5 mL of dioxane and 4.0 M HCl solution in dioxane (0.7 mL, 2.8 mmol, 20.0 equiv.) was added. Evaporation of solvents afforded the title compound as a white powder. $^1$H NMR (400 MHz, DMSO-d$_6$) δ 10.72 (bs, 1H), 9.71 (d, J=8.7 Hz, 2H), 7.65 (s, 2H), 7.58 (s, 1H), 7.57-7.47 (m, 1H), 7.46-7.37 (m, 2H), 7.35-7.23 (m, 2H), 4.20 (d, J=5.1 Hz, 2H), 3.86 (t, J=5.5 Hz, 2H), 3.33-3.15 (m, 2H), 2.96-2.74 (m, 2H), 2.62-2.47 (m, 2H), 2.46-2.28 (m, 2H), 2.06-1.50 (m, 9H), 1.47-1.15 (m, 1H).

Preparation of 4-[[[1-(3-Fluorophenyl)cyclopentyl]amino]methyl]-2-[(4-methylpiperazin-1-yl)methyl]phenol trihydrochloride (Example 22)

The title compound was prepared according to the general procedure for the synthesis of compounds of Formula Ia, starting from INTERMEDIATE 19 (46.0 mg, 0.19 mmol), INTERMEDIATE 8 (35.0 mg, 0.19 mmol) and NaBH(OAc)$_3$ (80.0 mg, 0.38 mmol) in DCM (2.5 mL). The crude was purified by column chromatography [DCM/MeOH (20% in DCM), from 95:5 to 50:50] to afford the free base of the title compound as a colorless oil, (50.0 mg, 67%). UPLC-MS (method generic A): Rt 1.70 min, MS (ES) C$_{24}$H$_{32}$FN$_3$O requires m/z 397, found m/z 398 [M+H]$^+$. The free base (50.0 mg, 0.12 mmol) was then dissolved in 0.5 mL of dioxane and 4.0 M HCl solution in dioxane (0.6 mL, 2.4 mmol, 20.0 equiv.) was added. Evaporation of solvents afforded the title compound as a white powder $^1$H NMR (400 MHz, DMSO-d$_6$) δ 11.82 (bs, 1H), 10.72 (bs, 1H), 9.92 (bs, 2H), 7.74-7.50 (m, 4H), 7.43 (s, 1H), 7.34-7.20 (m, 1H), 6.97 (d, J=8.4 Hz, 1H), 4.38-3.98 (m, 2H), 3.78-3.50 (m, 8H), 3.51-3.22 (m, 2H), 2.81 (s, 3H), 2.47-2.30 (m, 4H), 2.01-1.78 (m, 2H), 1.64-1.40 (m, 2H).

Preparation of 4-[[[1-(4-Fluorophenyl)cyclopentyl]amino]methyl]-2-[(4-methylpiperazin-1-yl)methyl]phenol trihydrochloride (Example 23)

The title compound was prepared according to the general procedure for the synthesis of compounds of Formula Ia, starting from INTERMEDIATE 20 (46.0 mg, 0.19 mmol), INTERMEDIATE 8 (35.0 mg, 0.19 mmol) and NaBH(OAc)$_3$ (80.0 mg, 0.38 mmol) in DCM (2.5 mL). The crude was purified by column chromatography [DCM/MeOH (20% in DCM), from 95:5 to 50:50] to afford the free base of the title compound as a colorless oil, (53.0 mg, 69%). UPLC-MS (method generic A): Rt 1.66 min, MS (ES) C$_{24}$H$_{32}$FN$_3$O requires m/z 397, found m/z 398 [M+H]$^+$. The free base (53.0 mg, 0.13 mmol) was then dissolved in 0.5 mL of dioxane and 4.0 M HCl solution in dioxane (0.65 mL, 2.6 mmol, 20.0 equiv.) was added. Evaporation of solvents afforded the title compound as a white powder. $^1$H NMR (400 MHz, DMSO-d$_6$) δ 11.85 (bs, 1H), 10.71 (bs, 1H), 9.85 (s, 2H), 7.83 (dd, J=8.7, 5.2 Hz, 2H), 7.41 (s, 1H), 7.33 (t, J=8.7 Hz, 2H), 7.29-7.20 (m, 1H), 6.98 (d, J=8.4 Hz, 1H), 4.50-3.97 (m, 2H), 3.79-3.50 (m, 10H), 2.81 (s, 3H), 2.48-2.29 (m, 4H), 1.94-1.78 (m, 2H), 1.57-1.41 (m, 2H).

Preparation of 1-(2-Fluorophenyl)-N-[[3-[(4-ethylcyclohexyl)methyl]phenyl]methyl]cyclopentanamine hydrochloride (1:1 cis:trans ratio (Example 24)

The title compound was prepared according to the general procedure for the synthesis of compounds of Formula Ia, starting from INTERMEDIATE 1 (25.0 mg, 0.11 mmol), INTERMEDIATE 28 (20.0 mg, 0.11 mmol) and NaBH(OAc)$_3$ (50.0 mg, 0.22 mmol) in DCM (2.5 mL). The crude was purified by column chromatography (Cy/EtOAc from 100:0 to 30:70) to afford the free base as mixture of 1:1 cis:trans stereoisomers, as colorless oil (31.0 mg, 75%). UPLC-MS (method generic B): Rt 3.05 min, MS (ES) C$_{26}$H$_{34}$FN requires m/z 379, found m/z 380 [M+H]$^+$. The free base (31.0 mg, 0.08 mmol) was then dissolved in 0.5 mL of dioxane and 4.0 M HCl solution in dioxane (0.05 mL, 0.16 mmol, 20.0 equiv.) was added. Evaporation of solvents afforded the title compound as a white powder. $^1$H NMR (400 MHz, DMSO-d$_6$) δ 9.44 (bs, 4H), 7.64-7.56 (m, 2H), 7.56-7.47 (m, 2H), 7.35-7.28 (m, 4H), 7.28-7.20 (m, 2H), 7.16-7.10 (m, 4H), 7.07 (d, J=7.3 Hz, 2H), 3.82 (dd, J=7.2, 4.7 Hz, 4H), 2.52-2.29 (m, 12H), 2.01-1.82 (m, 4H), 1.73-1.51 (m, 10H), 1.49-1.20 (m, 10H), 1.04-0.64 (m, 10H).

Preparation of 2-[(4-Methylpiperazin-1-yl)methyl]-4-[[[1-(2-thienyl)cyclopentyl]amino]methyl]phenol trihydrochloride (Example 25)

The title compound was prepared according to the general procedure for the synthesis of compounds of Formula Ia, starting from INTERMEDIATE 21 (35.0 mg, 0.15 mmol), INTERMEDIATE 8 (25.0 mg, 0.15 mmol) and NaBH(OAc)$_3$ (64.0 mg, 0.30 mmol) in DCM (2.5 mL). The crude was purified by column chromatography [DCM/MeOH (20% in DCM), from 100:0 to 0:100] to afford the free base of the title compound as a colorless oil, (36.0 mg, 60%). UPLC-MS (method generic A): Rt 1.44 min, MS (ES) C$_{22}$H$_{31}$N$_3$OS requires m/z 385, found m/z 386 [M+H]$^+$. The free base (36.0 mg, 0.10 mmol) was then dissolved in 0.5 mL of dioxane and 4.0 M HCl solution in dioxane (0.50 mL, 2.0 mmol, 20.0 equiv.) was added. Evaporation of solvents afforded the title compound as a white powder. $^1$H NMR (400 MHz, DMSO-d$_6$) 10.68 (bs, 1H), 9.91 (bs, 2H), 7.71 (dd, J=5.1, 1.1 Hz, 1H), 7.55 (dd, J=3.7, 1.2 Hz, 1H), 7.52-7.38 (m, 1H), 7.38-7.26 (m, 1H), 7.19 (dd, J=5.1, 3.6 Hz, 1H), 7.08-6.85 (m, 1H), 4.46-3.97 (m, 2H), 3.86-3.67 (m, 2H), 3.67-3.53 (m, 2H), 3.52-3.12 (m, 6H), 2.81 (s, 3H), 2.49-2.26 (m, 4H), 2.02-1.74 (m, 2H), 1.70-1.41 (m, 2H).

Preparation of 4-[[[1-(2,4-Difluorophenyl)cyclopentyl]amino]methyl]-2-[(4-methylpiperazin-1-yl)methyl]phenol trihydrochloride (Example 26)

The title compound was prepared according to the general procedure for the synthesis of compounds of Formula Ia, starting from INTERMEDIATE 22 (46.0 mg, 0.19 mmol), INTERMEDIATE 8 (36.0 mg, 0.19 mmol) and NaBH(OAc)$_3$ (80.0 mg, 0.38 mmol) in DCM (2.5 mL). The crude was purified by column chromatography [DCM/MeOH (20% in DCM), from 100:0 to 0:100] to afford the free base of the title compound as a colorless oil, (50.0 mg, 67%). UPLC-MS (method generic A): Rt 2.30 min, MS (ES) C$_{24}$H$_{31}$F$_2$N$_3$O requires m/z 415, found m/z 416 [M+H]$^+$. The free base (50.0 mg, 0.12 mmol) was then dissolved in 0.5 mL of dioxane and 4.0 M HCl solution in dioxane (0.60 mL, 2.4 mmol, 20.0 equiv.) was added. Evaporation of solvents afforded the title compound as a white powder. $^1$H NMR (400 MHz, DMSO-d$_6$) δ 12.86-11.30 (m, 1H), 10.73 (bs, 1H), 9.32 (bs, 2H), 7.55 (ddd, J=14.6, 8.4, 6.1 Hz, 1H), 7.48 (s, 1H), 7.33-7.07 (m, 3H), 6.93 (d, J=8.4 Hz, 1H), 4.57-3.97 (m, 2H), 3.95-3.79 (m, 2H), 3.78-3.58 (m, 2H), 3.41 (s, 6H), 2.81 (s, 3H), 2.75-2.57 (m, 2H), 2.42-2.18 (m, 2H), 2.10-1.85 (m, 2H), 1.81-1.52 (m, 2H).

Preparation of 4-[[[1-(3-Methoxyphenyl)cyclopentyl]amino]methyl]-2-[(4-methylpiperazin-1-yl)methyl]phenol trihydrochloride (Example 27)

The title compound was prepared according to the general procedure for the synthesis of compounds of Formula Ia, starting from INTERMEDIATE 23 (42.0 mg, 0.18 mmol), INTERMEDIATE 8 (35.0 mg, 0.18 mmol) and NaBH(OAc)$_3$ (76.0 mg, 0.36 mmol) in DCM (3.0 mL). The crude was purified by column chromatography [DCM/MeOH (20% in DCM), from 100:0 to 0:100] to afford the free base of the title compound as a colorless oil, (50.0 mg, 68%). UPLC-MS (method generic A): Rt 1.63 min, MS (ES) $C_{25}H_{35}N_3O_2$ requires m/z 409, found m/z 410 [M+H]$^+$. The free base (50.0 mg, 0.12 mmol) was then dissolved in 0.5 mL of dioxane and 4.0 M HCl solution in dioxane (0.60 mL, 2.4 mmol, 20.0 equiv.) was added. Evaporation of solvents afforded the title compound as a white powder. $^1$H NMR (400 MHz, DMSO-d$_6$) δ 11.74 (s, 1H), 10.76 (s, 1H), 9.76 (m, 2H), 7.47-7.34 (m, 3H), 7.26 (m, 2H), 7.05-6.93 (m, 2H), 4.46-3.99 (m, 2H), 3.82 (s, 3H), 3.61 (m, 8H), 3.50-3.25 (m, 2H), 2.82 (s, 3H), 2.44-2.25 (m, 4H), 1.85 (m, 2H), 1.52 (m, 2H).

Preparation of 1-(2-Fluorophenyl)-N-[[4-[(4-methyl piperazin-1-yl)methyl]phenyl]methyl]cyclopentanamine trihydrochloride (Example 28)

The title compound was prepared according to the general procedure for the synthesis of compounds of Formula Ia, starting from INTERMEDIATE 1 (35.0 mg, 0.19 mmol), INTERMEDIATE 26 (43.0 mg, 0.19 mmol) and NaBH(OAc)$_3$ (80.0 mg, 0.38 mmol) in DCM (3.0 mL). The crude was purified by column chromatography [DCM/MeOH (20% in DCM), from 100:0 to 0:100] to afford the free base of the title compound as a colorless oil, (52.0 mg, 72%). UPLC-MS (method generic A): Rt 2.06 min, MS (ES) $C_{24}H_{32}FN_3$ requires m/z 381, found m/z 382 [M+H]$^+$. The free base (50.0 mg, 0.12 mmol) was then dissolved in 0.5 mL of dioxane and 4.0 M HCl solution in dioxane (0.60 mL, 2.4 mmol, 20.0 equiv.) was added. Evaporation of solvents afforded the title compound as a white powder. $^1$H NMR (400 MHz, DMSO-d$_6$) δ 12.07 (bs, 1H), 9.69 (bs, 2H), 7.67-7.53 (m, 3H), 7.48 (tdd, J=7.3, 5.0, 1.6 Hz, 1H), 7.40 (d, J=7.8 Hz, 2H), 7.34-7.19 (m, 2H), 4.28 (s, 2H), 3.88 (t, J=5.7 Hz, 2H), 3.65-3.55 (m, 2H), 3.54-3.20 (m, 6H), 2.77 (s, 3H), 2.60-2.55 (m, 2H), 2.40-2.32 (m, 2H), 2.04-1.79 (m, 2H), 1.71-1.47 (m, 2H).

Preparation of 1-(2-Fluorophenyl)-N-[[2-[(4-methyl piperazin-1-yl)methyl]phenyl]methyl]cyclopentanamine trihydrochloride (Example 29)

The title compound was prepared according to the general procedure for the synthesis of compounds of Formula Ia, starting from INTERMEDIATE 1 (46.0 mg, 0.26 mmol), INTERMEDIATE 27 (56.0 mg, 0.26 mmol) and NaBH(OAc)$_3$ (110.0 mg, 0.52 mmol) in DCM (3.0 mL). The crude was purified by column chromatography [DCM/MeOH (20% in DCM), from 100:0 to 0:100] to afford the free base of the title compound as a colorless oil, (52.0 mg, 55%). UPLC-MS (method generic A): Rt 2.05 min, MS (ES) $C_{24}H_{32}FN_3$ requires m/z 381, found m/z 382 [M+H]$^+$. The free base (52.0 mg, 0.13 mmol) was then dissolved in 0.5 mL of dioxane and 4.0 M HCl solution in dioxane (0.65 mL, 2.6 mmol, 20.0 equiv.) was added. Evaporation of solvents afforded the title compound as a white powder. $^1$H NMR (400 MHz, DMSO-d$_5$) δ 11.86-11.06 (bs, 1H), 10.17-9.24 (bs, 2H), 7.70 (t, J=8.1 Hz, 1H), 7.60-7.43 (m, 2H), 7.37 (q, J=7.0 Hz, 2H), 7.33-7.20 (m, 2H), 7.07 (d, J=7.6 Hz, 1H), 4.07 (s, 2H), 3.87-3.25 (m, 8H), 3.36-3.00 (m, 2H), 2.77 (s, 3H), 2.62-2.36 (m, 4H), 2.11-1.80 (m, 2H), 1.75-1.42 (m, 2H).

Preparation of 4-(2-Fluorophenyl)-N-[[3-[(1-methyl-4-piperidyl)methyl]phenyl]methyl]tetrahydropyran-4-amine dihydrochloride (Example 30)

The title compound was prepared according to the general procedure for the synthesis of compounds of Formula Ia, starting from INTERMEDIATE 4 (61.0 mg, 0.31 mmol), INTERMEDIATE 18 (68.0 mg, 0.31 mmol) and NaBH(OAc)$_3$ (131.0 mg, 0.52 mmol) in DCM (3.0 mL). The crude was purified by column chromatography [DCM/MeOH (20% in DCM), from 100:0 to 0:100] to afford the free base of the title compound as a colorless oil, (52.0 mg, 43%). UPLC-MS (method generic A): Rt 2.16 min, MS (ES) $C_{25}H_{33}FN_2O$ requires m/z 396, found m/z 397 [M+H]$^+$. The free base (52.0 mg, 0.13 mmol) was then dissolved in 0.5 mL of dioxane and 4.0 M HCl solution in dioxane (0.65 mL, 2.6 mmol, 20.0 equiv.) was added. Evaporation of solvents afforded the title compound as a white powder. $^1$H NMR (400 MHz, DMSO-d$_6$) δ 10.55 (bs, 1H), 9.83 (bs, 2H), 7.87-7.73 (m, 1H), 7.66-7.44 (m, 1H), 7.44-7.31 (m, 2H), 7.31-7.22 (m, 1H), 7.22-7.09 (m, 3H), 4.01-3.88 (m, 2H), 3.76 (t, J=6.1 Hz, 2H), 3.38-3.27 (m, 2H), 3.25-3.08 (m, 2H), 2.93-2.70 (m, 4H), 2.66 (d, J=4.7 Hz, 3H), 2.52-2.32 (m, 4H), 1.83-1.62 (m, 3H), 1.49 (d, J=2.0 Hz, 2H).

Preparation of 4-[[3-[[[1-(2-Fluorophenyl)cyclopentyl]amino]methyl]phenyl]methyl]cyclohexanol hydrochloride (Example 31)

The title compound was prepared according to the general procedure for the synthesis of compounds of Formula Ia, starting from INTERMEDIATE 1 (24.0 mg, 0.13 mmol), INTERMEDIATE 29 (30.0 mg, 0.13 mmol) and NaBH(OAc)$_3$ (55.0 mg, 0.26 mmol) in DCM (2.5 mL). The crude was purified by column chromatography [DCM/MeOH (20% in DCM), from 100:0 to 0:100] to afford the free base of the title compound as a colorless oil, (26.0 mg, 53%). UPLC-MS (method generic A): Rt 2.92 min, MS (ES) $C_{25}H_{32}FNO$ requires m/z 381, found m/z 382 [M+H]$^+$. The free base (26.0 mg, 0.07 mmol) was then dissolved in 0.5 mL of dioxane and 4.0 M HCl solution in dioxane (0.34 mL, 1.4 mmol, 20.0 equiv.) was added. Evaporation of solvents afforded the title compound as a white powder. $^1$H NMR (400 MHz, DMSO-d$_6$) δ 9.27 (bs, 2H), 7.64-7.47 (m, 2H), 7.35-7.10 (m, 3H), 7.15-7.10 (m, 3H), 3.81 (t, J=5.8 Hz, 2H), 2.46-2.32 (m, 7H), 1.95-1.85 (m, 2H), 1.82-1.73 (m, 2H), 1.65-1.52 (m, 4H), 1.46-1.28 (m, 2H), 1.15-0.79 (m, 4H).

Preparation of 1-(4-Fluorophenyl)-N-[[3-[(1-methyl-4-piperidyl)methyl]phenyl]methyl]cyclopentanamine dihydrochloride (Example 32)

The title compound was prepared according to the general procedure for the synthesis of compounds of Formula Ia, starting from INTERMEDIATE 20 (41.0 mg, 0.23 mmol), INTERMEDIATE 18 (50.0 mg, 0.23 mmol) and NaBH (OAc)₃ (97.0 mg, 0.46 mmol) in DCM (3.0 mL). The crude was purified by column chromatography [DCM/MeOH (20% in DCM), from 100:0 to 0:100] to afford the free base of the title compound as a colorless oil, (45.0 mg, 52%). UPLC-MS (method generic A): Rt 2.31 min, MS (ES) $C_{25}H_{33}FN_2$ requires m/z 380, found m/z 381 [M+H]⁺. The free base (40.0 mg, 0.11 mmol) was then dissolved in 0.5 mL of dioxane and 4.0 M HCl solution in dioxane (0.55 mL, 2.2 mmol, 20.0 equiv.) was added. Evaporation of solvents afforded the title compound as a white powder. ¹H NMR (400 MHz, DMSO-d₆) δ 10.35 (bs, 1H), 9.88 (bs, 2H), 7.81 (ddd, J=8.7, 5.2, 2.5 Hz, 2H), 7.41-7.26 (m, 3H), 7.24-7.13 (m, 3H), 3.73-3.62 (m, 2H), 3.42-3.25 (m, 2H), 2.93-2.72 (m, 2H), 2.68 (d, J=4.6 Hz, 3H), 2.50-2.46 (m, 1H), 2.44-2.28 (m, 4H), 1.96-1.79 (m, 2H), 1.83-1.63 (m, 3H), 1.65-1.35 (m, 4H), 1.32-1.17 (m, 1H).

Preparation of 4-[[[1-(2-Fluorophenyl)cyclobutyl]amino]methyl]-2-[(4-methylpiperazin-1-yl)methyl]phenol trihydrochloride (Example 33)

The title compound was prepared according to the general procedure for the synthesis of compounds of Formula Ia, starting from INTERMEDIATE 24 (45.0 mg, 0.26 mmol), INTERMEDIATE 8 (61.0 mg, 0.26 mmol) and NaBH(OAc)₃ (110.0 mg, 0.52 mmol) in DCM (3.0 mL). The crude was purified by column chromatography [DCM/MeOH (20% in DCM), from 100:0 to 0:100] to afford the free base of the title compound as a colorless oil, (60.0 mg, 60%). UPLC-MS (method generic A): Rt 1.70 min, MS (ES) $C_{23}H_{30}FN_3O$ requires m/z 383, found m/z 384 [M+H]⁺. The free base (50.0 mg, 0.13 mmol) was then dissolved in 0.5 mL of dioxane and 4.0 M HCl solution in dioxane (0.65 mL, 2.6 mmol, 20.0 equiv.) was added. Evaporation of solvents afforded the title compound as a white powder. ¹H NMR (400 MHz, DMSO-d₆) δ 11.95 (bs, 1H), 10.80 (bs, 1H), 9.95 (bs, 2H), 7.71-7.61 (m, 1H), 7.57-7.44 (m, 2H), 7.38-7.23 (m, 3H), 6.97 (d, J=8.4 Hz, 1H), 4.37-4.07 (m, 2H), 3.80-3.65 (m, 2H), 3.65-3.53 (m, 2H), 3.53-3.19 (m, 6H), 2.99-2.84 (m, 2H), 2.80 (s, 3H), 2.76-2.61 (m, 2H), 2.41-2.21 (m, 1H), 1.90-1.67 (m, 1H).

Biological Methods to assess the activity of the compounds according to the invention Luciferase-base assay to assess the activity of the oompounds on REV-ERB mediated transcriptional regulation In order to assess the effect of the compounds of the invention on REV-ERB activity the inventors exploited the ability of REV-ERB to repress gene transcription of a specific DNA cis-element. In fact, the DNA binding domain (DBD) of REV-ERB recognizes specific DNA sequences (called RevREs=Rev-erb Responsive Elements) which contains an AGGTCA motif linked in 5' to an A/T rich sequence harboring the following consensus: A/T A A/T N T (Harding et al., Mol Cell Biol., 1993; 13:3113).

Therefore, two repetitions of the RevRE consensus AGAATGTAGGTCA (SEQ ID NO: 13) upstream a SV40 promoter driving the expression of a reporter gene were cloned. As reported, the luciferase enzyme from the ostracod *Cypridina noctiluca* was adopted. This luciferase does not require ATP and catalyzes the oxidation of its luciferin substrate in a photochemical reaction that can be measured by a luminometer. *Cypridina* luciferase (CLuc) is secreted from cells by virtue of its natural signal peptide and its luminescence can be measured from the supernatant of transfected cells. Therefore, cell lysis is not necessary. Secreted CLuc is a very stable protein. Because of this property, the activity measured from the supernatant reflects the amount of protein accumulated up to the time of sampling. Multiple samples can therefore be obtained from the same transfected cells, allowing an easy set-up of time-course experiments. In addition, the direct use of the supernatant makes the system easily prone to automation for High Throughput Screening.

In order to normalize the experiment for the transfection efficiency, it was used a plasmid containing a SV40 promoter driving the expression of a secreted form of human alkaline phosphatase (SEAP), which enzymatic activity in the supernatant can be measured with chemiluminescence substrates.

To be able to rule out false-positive, for example due to the interference of the compounds to be tested with the fluorescence and/or chemiluminescence reactions, it was used as control a mutated version of the RevRE (GAGC-CCGTAGGTCA)-(SEQ ID NO: 14) that is no longer able to bind REV-ERB DBD (Harding et al., Mol Cell Biol., 1993; 13:3113).

Agonists or antagonists of REV-ERB modify the expression of the CLuc reporter driven by the wild-type RevRE/SV40 promoter, but produce negligible effects on the CLuc reporter driven by the mutated RevRE/SV40 promoter.

The person skilled in the art will appreciate that an agonist will improve the ability of REV-ERB to repress the transcription, reducing the luminescence signal, while an antagonist will produce the opposite effect.

For the assay, HEK-293 cells were transfected with the reporter vectors and a plasmid expressing the REV-ERBα and/or β protein. After 6 h from transfection, the medium was replaced with fresh medium containing different doses of the compounds or vehicle (DMSO). After 24 h post-transfection, the supernatant was analyzed for the secreted luciferase and AP activity according to the manufacture instruction. Data normalized as fold activation versus vehicle (DMSO) were fitted using a four-parameter dose-response curve to calculate the $EC_{50}$ of the different compounds.

Growth inhibition assay

Given that REV-ERB target genes include several metabolic regulators, such as Pgc-1α and Nampt, it was decided to test the cell proliferation with a method that is independent from the metabolic state of the cell.

The CyQUANT® Cell Proliferation Assay Kit (Invitrogen) was used, an assay that has a linear detection range extending from 50 or fewer to at least 250,000 cells. The CyQUANT® method is rapid, does not rely on cellular metabolic activity, and uses a proprietary green fluorescent dye, CyQUANT® GR dye, which exhibits strong fluorescence enhancement when bound to cellular nucleic acids.

Frozen cells are simply thawed and lysed by addition of a buffer containing the CyQUANT®.

For the assay, tumorigenic breast cancer cells BT-474 cells were seeded at 2500 cells per well in a 96-well plate and incubated over-night at 37° C. Then, fresh medium containing different concentration of the compounds or vehicle (DMSO) was added and cells were growth 48 h at 37° C. Finally, cells were frozen at 80° C. and then processed according to the manufacture instructions. A minimum of triplicate data for each dose was used for the analysis.

Data were collected and analyzed with Prism 5 software to calculate the growth inhibition curve.

In particular, values obtained from the DMSO treated cells was set at 100% of growth. Data from treatment of cells with serial dilutions of the compounds were normalized versus the DMSO group and fitted using a four-parameter dose-response curve.

$GI_{50}$ was calculated as the concentration of compound that gives a response half way between bottom and top plateaus of the fitted curve.

The bottom plateaus of the fitted curve was used to calculate the Growth Inhibition max ($GI_{max}$), defined as the percentage of the reduction of cells after 48 h upon a saturating dose of compound. The results obtained are reported in Table 28 below.

Biological activities of the compounds of the examples

The different compounds were tested for their ability to inhibit the growth of the tumorigenic breast cancer cells BT-474 and for their antagonistic activity toward REV-ERB transcriptional repression, as described in the biological method section. The results are illustrated in Table 28.

TABLE 28

| Example | Cell Growth Inibition | | REV-ERB antagonism |
|---|---|---|---|
| | $GI_{50}$ (µM) | $GI_{max}$ (%) | $EC_{50}$ (µM) |
| 1 | 18 | 72% | 25 |
| 2 | 30 | 55% | 45 |
| 3 | 14 | 95% | 20 |
| 4 | 30 | 73% | 47 |
| 5 | 26 | 75% | 43 |
| 7 | 18 | 70% | 24 |
| 9 | 30 | 50% | 50 |
| 10 | 15 | 70% | 25 |
| 11 | 24 | 70% | 40 |
| 12 | 23 | 77% | 40 |
| 14 | 19 | 82% | 23 |
| 17 | 18 | 90% | 21 |
| 18 | 2 | 95% | 8 |
| 19 | 5 | 90% | 11 |
| 20 | 11 | 92% | 12 |
| 21 | 50 | 76% | 35 |
| 22 | 14 | 80% | 15 |
| 23 | 10 | 90% | 10 |
| 25 | 18 | 70% | 29 |
| 27 | 12 | 70% | 16 |
| 30 | 3 | 95% | 6 |
| 32 | 1 | 97% | 2 |
| 33 | 30 | 70% | 38 |

For the cell growth inhibition (GI) the growth inhibition 50 ($GI_{50}$) and the growth inhibition max ($GI_{max}$) are reported. $GI_{50}$ corresponds to the concentration of compound that gives a response half between the Top (no inhibition=percentage of cells equal to DMSO group) and Bottom (percentage of cells after 48 h treatment) plateaus of the fitted curves. The bottom plateaus of the curve was used to calculate the Growth Inhibition max ($GI_{max}$), defined as the percentage of the reduction of cells after 48 h upon a saturating dose of the administered compound. Compounds with a $GI_{50}$<100 µM were also tested for their antagonistic activity toward REV-ERB. For these compounds, the $EC_{50}$ value is provided, calculated as the concentration of compound that gives a response half between the bottom (expression of the reporter in absence of compound) and the top (expression of the reporter at saturating doses of compound) plateaus of the fitted curves (see biological method section for a description of the reported assay). n.d.=not determined; n.t.=not tested.

Gene expression analysis of endogenous REV-ERB target genes after treatment with the compound of example 1

In order to test the effect of the compound of example 1 on the endogenous REV-ERB mediated transcription, BT-474 cells were treated 24 h with different doses of the compound of the example 1 and then processed for RNA extraction.

Total RNA was extracted with Trizol reagent (Invitrogen) according to the manufacture instruction. One microgram of RNA was retro-transcribed with VILO retrotranscription mix (Invitrogen) and subsequently analyzed by qPCR as described in Grimaldi et al., Cell Metab., 2010; 12:509-520.

The REV-ERB targets Per1, Bmal1, Nampt, and p21 were analyzed. Gapdh gene was used to normalize the data, while Hprt1 gene was used as independent REV-ERB gene (negative control).

Primers used for analysis are listed in Table 29.

TABLE 29

| Gene name | Alias | Left primer | Right primer |
|---|---|---|---|
| Per1 | Per1 | CAGTGCTCCTG-TTCCTGCATC (SEQ ID NO: 1) | CCCGCCAACTGC-AGAATCT (SEQ ID NO: 2) |
| Arnt1 | Bmal1 | CCAGAGGCCCC-TAACTCCTC (SEQ ID NO: 3) | TGGTCTGCCATT-GGATGATCT (SEQ ID NO: 4) |
| Nampt | Visfatin/Pebf | GAGTTCAACAT-CCTCCTGGC (SEQ ID NO: 5) | TCACGGCATTCA-AAGTAGGA (SEQ ID NO: 6) |
| Gapdh | Gapdh | AAGGTGAAGGT-CGGAGTCAA (SEQ ID NO: 7) | AATGAAGGGGTC-ATTGATGG (SEQ ID NO: 8) |

TABLE 29-continued

| Gene name | Alias | Left primer | Right primer |
|---|---|---|---|
| Hprt1 | Hprt1 | GTTATGGCGAC-CCGCAG (SEQ ID NO: 9) | ACCCTTTCCAAA-TCCTCAGC (SEQ ID NO: 10) |
| Cdkn1a | p21 | AGTCAGTTCCT-TGTGGAGCC (SEQ ID NO: 11) | CATGGGTTCTGA-CGGACAT (SEQ ID NO: 12) |

Indeed, example 1 induced in a dose-dependent manner the expression of REV-ERBs endogenous targets involved in circadian regulation (Per1 and Bmal1), metabolism (Nampt) and cell cycle (p21), while it showed negligible effects on the REV-ERB independent gene Hprt1. The results obtained are illustrated in FIG. 1 Values are presented as Relative expression, calculated versus the normalizing gene Gapdh, and shown as mean±SEM from at least 3 independent experiments. The expression of the REV-ERBs independent gene, Hprt1, was used as negative control.

Growth Inhibition of different tumor cell lines after treatment with the compound of example 1

To test if the growth inhibition activity of the compound of example 1 was limited to breast cancer BT-474 cells, or if it could be generalized in other tumor cells from different tissues, the GI50 of compound of example 1 was tested in several cell lines. In addition, because biological data suggested a p53-independent activity of the compound of example 1, cells with a different status of the tumor suppressor p53 protein were exploited.

The results are illustrated in Table 30.

TABLE 30

| Cell line | Origin | p53 status | GI50 (µM) |
|---|---|---|---|
| HCT116 | Colorectal carcinoma | Wild-Type | 19 |
| HCT116-E6 | Colorectal carcinoma | No protein expression | 20 |
| CaCO2 | Colorectal adenocarcinoma | No protein expression | 18 |
| WiDr | Colon adenocarcinoma | Mutant protein | 12 |
| Colo-205 | Colon metastatic site: ascites | Mutant protein | 30 |
| HepG2 | Liver hepatocellular carcinoma | Wild-Type | 10 |
| SK-Hep1 | Liver adenocarcinoma | Wild-Type | 50 |
| Hep3B | Liver hepatocellular carcinoma | No protein expression | 10 |
| HuH7 | Liver hepatocellular carcinoma | Mutant protein | 8 |

Indeed, the compound of example 1 displayed growth inhibition activity in different tumor cell lines, independently from the expression (status) of the tumor suppressor p53 (i.e. cells expressing a wild-type or mutated p53 protein, and cells in which p53 expression is ablated).

TABLE 1

| Example | Molecular Structure | Molecular Formula | MW | Name |
|---|---|---|---|---|
| 1 CAS number: 1287451-26-6 | 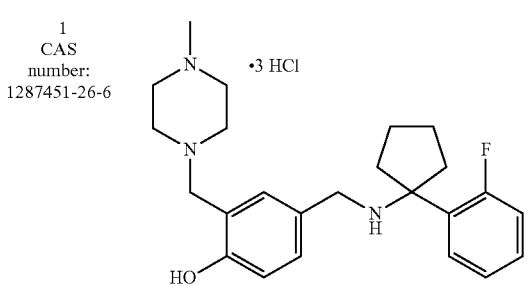 | $C_{24}H_{32}FN_3O \cdot 3HCl$ | 506.91 | 4-[[[1-(2-fluorophenyl) cyclopentyl]amino]methyl]-2-[(4-methylpiperazin-1-yl) methyl]phenol trihydrochloride |
| 2 | 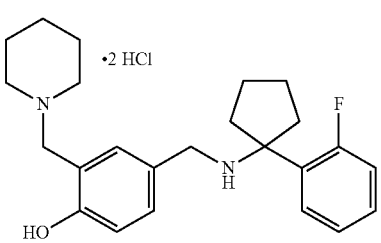 [SMILES: Oc1ccc(CNC2(c3ccccc3F)CCCC2)cc1CN1CCCCC1] | $C_{24}H_{31}FN_2O \cdot 2HCl$ | 455.44 | 4-[[[1-(2-fluorophenyl) cyclopentyl]amino]methyl]-2-(1-piperidylmethyl) phenol dihydrochloride |

TABLE 1-continued

| Example | Molecular Structure | Molecular Formula | MW | Name |
|---|---|---|---|---|
| 3 | 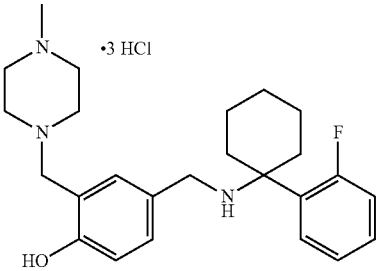 [SMILES: CN1CCN(Cc2cc(CNC3(c4ccccc4F)CCCCC3)ccc2O)CC1] | $C_{25}H_{34}FN_3O \cdot 3HCl$ | 520.94 | 4-[[[1-(2-fluorophenyl)cyclohexyl]amino]methyl]-2-[(4-methylpiperazin-1-yl)methyl]phenol trihydrochloride |
| 4 | 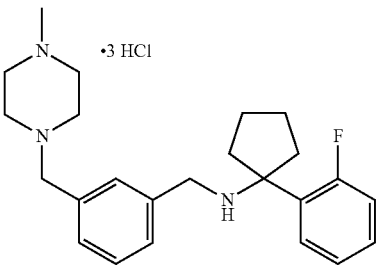 [SMILES: CN1CCN(Cc2cccc(CNC3(c4ccccc4F)CCCC3)c2)CC1] | $C_{24}H_{32}FN_3 \cdot 3HCl$ | 490.91 | 1-(2-fluorophenyl)-N-[[3-[(4-methylpiperazin-1-yl)methyl]phenyl]methyl]cyclopentanamine trihydrochloride |
| 5 | 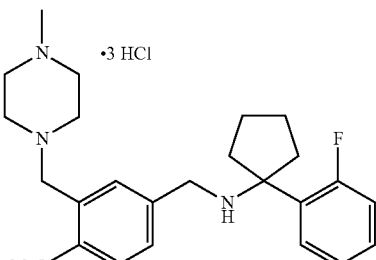 | $C_{25}H_{34}FN_3O \cdot 3HCl$ | 520.94 | 1-(2-fluorophenyl)-N-[[4-methoxy-3-[(4-methylpiperazin-1-yl)methyl]phenyl]methyl]cyclopentanamine trihydrochloride |
| 6 | 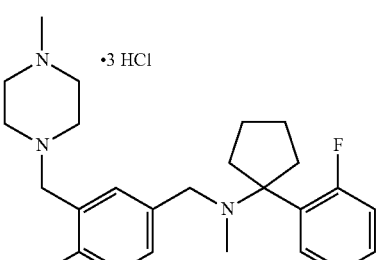 | $C_{25}H_{34}FN_3O \cdot 3HCl$ | 520.94 | 4-[[[1-(2-fluorophenyl)cyclopentyl]-methyl-amino]methyl]-2-[(4-methylpiperazin-1-yl) methyl]phenol trihydrochloride |
| 7 | 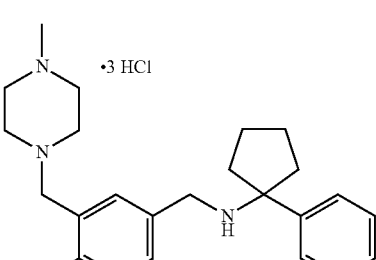 | $C_{24}H_{33}FN_3O \cdot 3HCl$ | 488.92 | 2-[(4-methylpiperazin-1-yl)methyl]-4-[[(1-phenylcyclopentyl)amino]methyl]phenol trihydrochloride |

TABLE 1-continued

| Example | Molecular Structure | Molecular Formula | MW | Name |
|---|---|---|---|---|
| 8 | 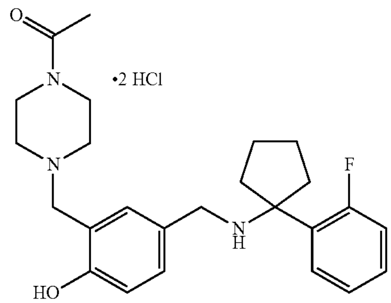 [SMILES: CC(=O)N1CCN(Cc2cc(CNC3(c4ccccc4F)CCCC3)ccc2O)CC1] | $C_{25}H_{32}FN_3O_2 \cdot 2HCl$ | 498.46 | 1-[4-[[5-[[[1-(2-fluorophenyl)cyclopentyl]amino]methyl]-2-hydroxyphenyl]methyl]piperazin-1-yl]ethanone dihydrochloride |
| 9 | 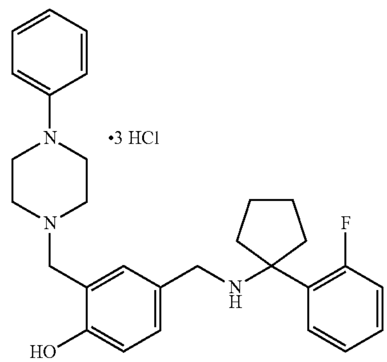 [SMILES: Oc1ccc(CNC2(c3ccccc3F)CCCC2)cc1CN1CCN(c2ccccc2)CC1] | $C_{29}H_{34}FN_3O \cdot 3HCl$ | 568.98 | 4-[[[1-(2-fluorophenyl)cyclopentyl]amino]methyl]-2-[(4-phenylpiperazin-1-yl)methyl]phenol trihydrochloride |
| 10 | 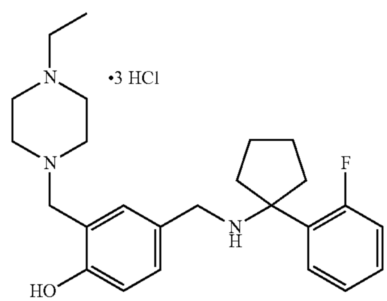 [SMILES: CCN1CCN(Cc2cc(CNC3(c4ccccc4F)CCCC3)ccc2O)CC1] | $C_{25}H_{34}FN_3O \cdot 3HCl$ | 520.94 | 2-[(4-ethylpiperazin-1-yl)methyl]-4-[[[1-(2-fluorophenyl)cyclopentyl]amino]methyl]phenol trihydrochloride |
| 11 | 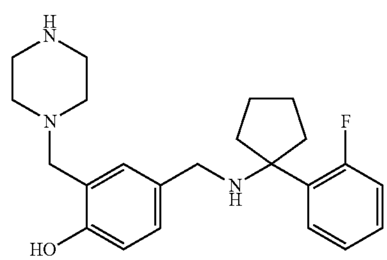 [SMILES: Oc1ccc(CNC2(c3ccccc3F)CCCC2)cc1CN1CCNCC1] | $C_{23}H_{30}FN_3O$ | 383.50 | 4-[[[1-(2-fluorophenyl)cyclopentyl]amino]methyl]-2-(piperazin-1-ylmethyl)phenol |
| 12 | 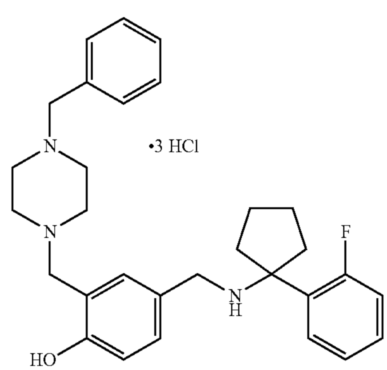 [SMILES: Oc1ccc(CNC2(c3ccccc3F)CCCC2)cc1CN1CCN(Cc2ccccc2)CC1] | $C_{30}H_{36}FN_3O \cdot 3HCl$ | 583.01 | 2-[(4-benzylpiperazin-1-yl)methyl]-4-[[[1-(2-fluorophenyl)cyclopentyl]amino]methyl]phenol trihydrochloride |

TABLE 1-continued

| Example | Molecular Structure | Molecular Formula | MW | Name |
|---|---|---|---|---|
| 13 | 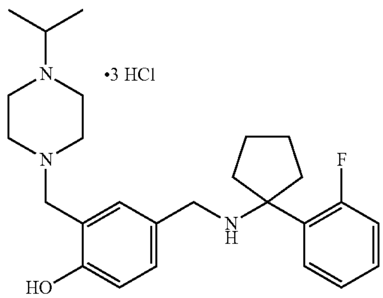 [SMILES: CC(C)N1CCN(Cc2cc(CNC3(c4ccccc4F)CCCC3)ccc2O)CC1] | $C_{26}H_{36}FN_3O \cdot 3HCl$ | 534.96 | 4-[[[1-(2-fluorophenyl)cyclopentyl]amino]methyl]-2-[(4-isopropylpiperazin-1-yl)methyl]phenol trihydrochloride |
| 14 CAS number: 1287488-37-2 | 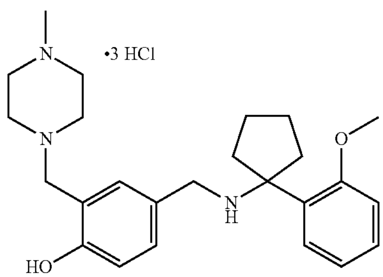 [SMILES: COc1ccccc1C1(NCc2ccc(O)c(CN3CCN(C)CC3)c2)CCCC1] | $C_{25}H_{35}N_3O_2 \cdot 3HCl$ | 517.20 | 4-{[1-(2-Methoxy-phenyl)-cyclopentyl-amino]-methyl}-2-(4-methylpiperazin-1-ylmethyl)-phenol trihydrochloride |
| 15 | 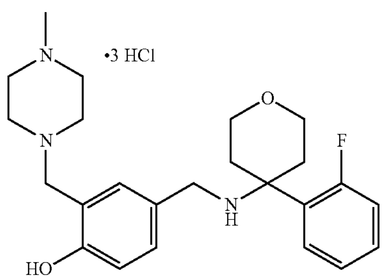 [SMILES: CN1CCN(Cc2cc(CNC3(c4ccccc4F)CCOCC3)ccc2O)CC1] | $C_{24}H_{32}FN_3O_2 \cdot 3HCl$ | 522.91 | 4-[[[1-(2-fluorophenyl)tetrahydropyran-4-yl]amino]methyl]-2-[(4-[methylpiperazin-1-yl)methyl]phenol trihydrochloride |
| 16 | 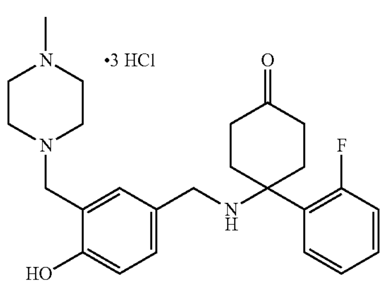 [SMILES: CN1CCN(Cc2cc(CNC3(c4ccccc4F)CCC(=O)CC3)ccc2O)CC1] | $C_{25}H_{32}FN_3O_2 \cdot 3HCl$ | 534.92 | 4-(2-fluorophenyl)-4-[[4-hydroxy-3-[(4-methylpiperazin-1-yl)methyl]phenyl]methylamino]cyclohexanone trihydrochloride |
| 17 | 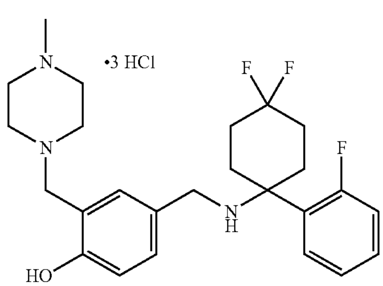 [SMILES: CN1CCN(Cc2cc(CNC3(c4ccccc4F)CCC(F)(F)CC3)ccc2O)CC1] | $C_{25}H_{32}F_3N_3O_2 \cdot 3HCl$ | 556.92 | 4-[[[4,4-difluoro-1-(2-fluorophenyl)cyclohexyl]amino]methyl]-2-[(4-methylpiperazin-1-yl)methyl]phenol trihydrochloride |

TABLE 1-continued

| Example | Molecular Structure | Molecular Formula | MW | Name |
|---|---|---|---|---|
| 18 | 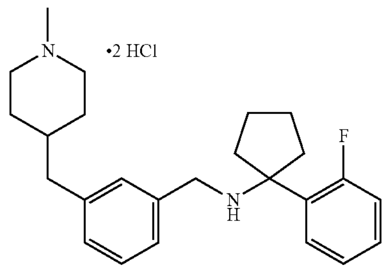 [SMILES: CN1CCC(Cc2cccc(CNC3(c4ccccc4F)CCCC3)c2)CC1] | $C_{25}H_{33}FN_2 \cdot 2HCl$ | 452.21 | 1-(2-fluorophenyl)-N-[[3-[(1-methyl-4-piperidyl)methyl]phenyl]methyl]cyclopentanamine dihydrochloride |
| 19 | 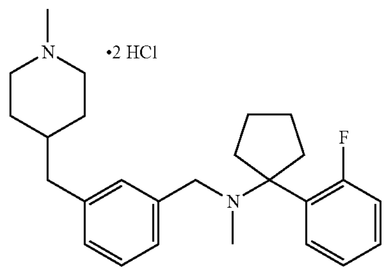 [SMILES: CN1CCC(Cc2cccc(CN(C)C3(c4ccccc4F)CCCC3)c2)CC1] | $C_{26}H_{35}FN_2 \cdot 2HCl$ | 467.49 | 1-(2-fluorophenyl)-N-methyl-N-[[3-[(1-methyl-4-piperidyl)methyl]phenyl]methyl]cyclopentanamine dihydrochloride |
| 20 | 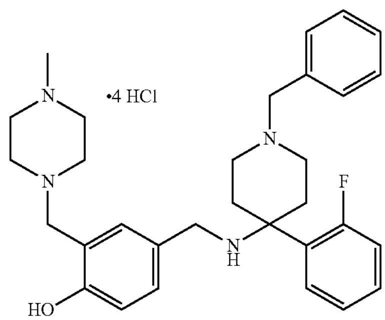 [SMILES: CN1CCN(Cc2cc(CNC3(c4ccccc4F)CCN(Cc4ccccc4)CC3)ccc2O)CC1] | $C_{31}H_{39}FN_4O \cdot 4HCl$ | 648.51 | 4-[[[1-benzyl-4-(2-fluorophenyl)-4-piperidyl]amino]methyl]-2-[(4-methylpiperazin-1-yl)methyl]phenol tetrahydrochloride |

TABLE 2

| Molecular Structure | Molecular Formula | MW | Name | $^1$H-NMR | UPLC/MS [m/z, rt (min)] |
|---|---|---|---|---|---|
| 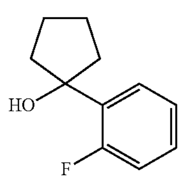 [SMILES: OC1(c2ccccc2F)CCCC1] | $C_{11}H_{13}FO$ | 180.09 | 1-(2-fluorophenyl)-cyclopentanol | $^1$H NMR (400 MHz, DMSO-d$_6$) δ 7.63 (td, J = 8.1, 1.9 Hz, 1H), 7.27 (tdd, J = 7.3, 5.0, 1.8 Hz, 1H), 7.19-7.05 (m, 2H), 4.92 (s, 1H), 2.04-1.92 (m, 2H), 1.93-1.80 (m, 4H), 1.80-1.66 (m, 2H) | — |
| 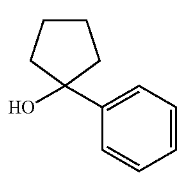 [SMILES: OC1(c2ccccc2)CCCC1] | $C_{11}H_{14}O$ | 162.10 | 1-phenylcyclopentanol | $^1$H NMR (400 MHz, DMSO-d$_6$) δ 7.52-7.42 (m, 2H), 7.34-7.26 (m, 2H), 7.22-7.14 (m, 1H), 4.73 (s, 1H), 1.92-1.79 (m, 6H), 1.74 (m, 2H) | — |

TABLE 2-continued

| Molecular Structure | Molecular Formula | MW | Name | ¹H-NMR | UPLC/MS [m/z, rt (min)] |
|---|---|---|---|---|---|
| 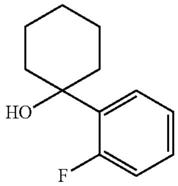 [SMILES: OC1(c2ccccc2F)CCCCC1] | $C_{12}H_{15}O$ | 194.11 | 1-(2-fluorophenyl)-cyclohexanol | ¹H NMR (400 MHz, DMSO-$d_6$) δ 7.65 (ddd, J = 8.5, 7.7, 1.9 Hz, 1H), 7.26 (dddd, J = 7.9, 6.9, 4.9, 1.9 Hz, 1H), 7.16 (td, J = 7.5, 1.3 Hz, 1H), 7.08 (ddd, J = 12.6, 8.0, 1.3 Hz,1H), 4.89 (t, J = 0.8 Hz, 1H), 2.03-1.88 (m, 2H), 1.83-1.63 (m, 3H), 1.62-1.43 (m, 4H), 1.32-1.15 (m, 1H) | 177 [M − OH]⁺, 2.55 |
| 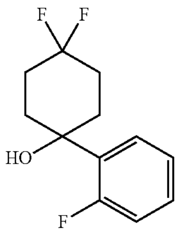 [SMILES: OC1(c2ccccc2F)CCC(F)(F)CC1] | $C_{12}H_{13}F_3O$ | 230.09 | 4,4-difluoro-1-(2-fluorophenyl)cyclohexanol | ¹H NMR (400 MHz, DMSO-$d_6$) δ 7.74-7.63 (m, 1H), 7.31 (dddd, J = 8.0, 7.0, 5.0, 1.9 Hz, 1H), 7.21 (td, J = 7.6, 1.3 Hz, 1H), 7.13 (ddd, J = 12.6, 8.1, 1.3 Hz, 1H), 5.43 (s, 1H), 2.32-2.10 (m, 4H), 1.94-1.87 (m, 2H), 1.80-1.66 (m, 2H). | |

TABLE 3

| Molecular Structure | Molecular Formula | MW | Name | ¹H-NMR |
|---|---|---|---|---|
| 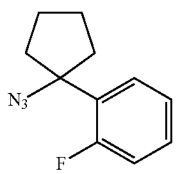 [SMILES: [N-]=[N+]=NC1(c2ccccc2F)CCCC1] | $C_{11}H_{12}FN_3$ | 205.10 | 1-(1-azidocyclopentyl)-2-fluoro-benzene | ¹H NMR (400 MHz, DMSO-$d_6$) δ 7.51-7.39 (m, 4H), 7.39-7.30 (m, 1H), 2.31-2.08 (m, 2H), 2.08-1.89 (m, 2H), 1.89-1.66 (m, 4H). |
| 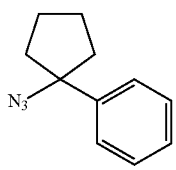 [SMILES: [N-]=[N+]=NC1(c2ccccc2)CCCC1] | $C_{11}H_{13}N_3$ | 187.11 | (1-azidocyclopentyl)benzene | ¹H NMR (400 MHz, DMSO-$d_6$) δ 7.51-7.39 (m, 4H), 7.39-7.30 (m, 1H), 2.31-2.08 (m, 2H), 2.08-1.89 (m, 2H), 1.89-1.66 (m, 4H). |
| 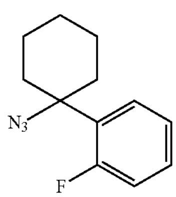 [SMILES: [N-]=[N+]=NC1(c2ccccc2F)CCCCC1] | $C_{11}H_{14}FN_3$ | 219.12 | 1-(1-azidocyclohexyl)-2-fluoro-benzene | ¹H NMR (400 MHz, DMSO-$d_6$) δ 7.51-7.39 (m, 4H), 7.39-7.30 (m, 1H), 2.31-2.08 (m, 2H), 208-1.89 (m, 2H), 1.89-1.66 (m, 4H). |

TABLE 4

| Amine Intermediate | Molecular Structure | Molecular Formula | MW | Name | ¹H-NMR | UPLC/MS [m/z, rt (min)] |
|---|---|---|---|---|---|---|
| 1 | 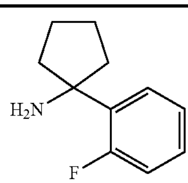 | $C_{11}H_{14}FN$ | 179.11 | 1-(2-fluorophenyl)-cyclopentanamine | ¹H NMR (400 MHz, DMSO-$d_6$) δ 7.57-7.47 (m, 1H), 7.25 (dddd, J = 7.9, 7.0, 5.3, 2.8 Hz, 1H), 7.18-7.04 (m, 2H), 1.98-1.84 (m, 4H), 1.84-1.72 (m, 4H), 1.72-1.62 (m, 2H). | 180 [M + H]⁺, 1.26 |

TABLE 4-continued

| Amine Intermediate | Molecular Structure | Molecular Formula | MW | Name | ¹H-NMR | UPLC/MS [m/z, rt (min)] |
|---|---|---|---|---|---|---|
| 2 | 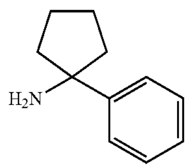 [SMILES: NC1(c2ccccc2)CCCC1] | $C_{11}H_{15}N$ | 161.12 | 1-phenyl-cyclopentanamine | ¹H NMR (400 MHz, DMSO-$d_6$) δ 7.54-7.43 (m, 2H), 7.32-7.24 (m, 2H), 7.22-7.10 (m, 1H), 1.95-1.79 (m, 4H), 1.79-1.61 (m, 6H). | 161 [M]⁺, 1.19 |
| 3 | 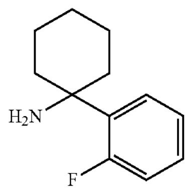 [SMILES: NC1(c2ccccc2F)CCCCC1] | $C_{11}H_{16}FN_2$ | 193.13 | 1-(2-fluorophenyl)-cyclohexanamine | ¹H NMR (400 MHz, DMSO-$d_6$) δ 7.60 (ddd, J = 9.1, 7.9, 1.8 Hz, 1H), 7.28-7.21 (m, 1H), 7.18-7.03 (m, 2H), 1.95 (td, J = 12.5, 3.8 Hz, 2H), 1.86-1.68 (m, 4H), 1.60 (ddt, J = 20.5, 13.0, 3.9 Hz, 3H), 1.45 (dp, J = 12.0, 3.8 Hz, 2H), 1.25 (qq, J = 12.0, 4.2, 3.7 Hz, 1H). | 194 [M + H]⁺, 1.33 |

TABLE 5

| Molecular Structure | Molecular Formula | MW | Name | ¹H-NMR | UPLC/MS [m/z, rt (min)] |
|---|---|---|---|---|---|
| 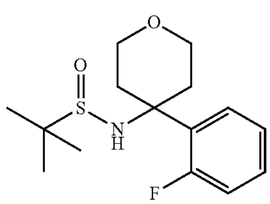 [SMILES: CC(C)(C)S(=O)NC1(c2ccccc2F)CCOCC1] | $C_{15}H_{22}FNO_2S$ | 299.13 | N-[4-(2-fluorophenyl)-tetrahydropyran-4-yl]-2-methyl-propane-2-sulfinamide | ¹H NMR (400 MHz, CDCl₃) δ 7.38 (td, J = 8.0, 1.7 Hz, 1H), 7.34 (m, 1H), 7.17 (td, J = 7.6, 1.3 Hz, 1H), 7.07 (ddd, J = 13.3, 8.1, 1.3 Hz, 1H), 4.06-3.99 (m, 1H), 3.94 (tdd, J = 11.8, 9.7, 3.0 Hz, 2H), 3.85 (dt, J = 11.8, 4.3 Hz, 1H), 3.77 (dt, J = 11.8, 4.1 Hz, 1H), 2.52-2.29 (m, 4H), 2.24 (ddd, J = 14.1, 9.9, 4.2 Hz, 1H), 1.22 (s, 9H). | 300 [M + H]⁺, 2.00 |
| 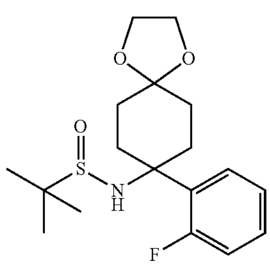 [SMILES: CC(C)(C)S(=O)NC1(c2ccccc2F)CCC2(CC1)OCCO2] | $C_{18}H_{26}FNO_3S$ | 355.16 | N-[8-(2-fluorophenyl)-1,4-dioxaspiro[4.5]decan-8-yl]-2-methyl-propane-2-sulfinamide | ¹H NMR (400 MHz, DMSO-$d_6$) δ 7.67-7.53 (m, 1H), 7.31 (tdd, J = 8.0, 4.9, 1.7 Hz, 1H), 7.19-7.03 (m, 2H), 5.18 (s, 1H), 3.87 (tq, J = 3.0, 1.5, 0.9 Hz, 4H), 2.39-2.10 (m, 4H), 1.95-1.74 (m, 2H), 1.50 (d, J = 13.3 Hz, 2H), 1.12 (s, 9H). | — |
| 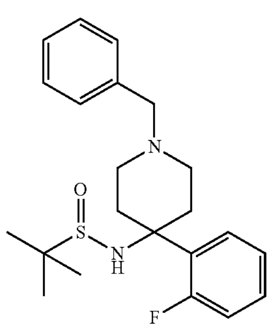 [SMILES: CC(C)(C)S(=O)NC1(c2ccccc2F)CCN(Cc2ccccc2)CC1] | $C_{22}H_{29}FN_2OS$ | 388.19 | N-[1-benzyl-4-(2-fluorophenyl)-4-piperidyl]-2-methyl-propane-2-sulfinamide | ¹H NMR (400 MHz, DMSO-$d_6$) δ 7.34 (d, J = 3.9 Hz, 4H), 7.40-7.19 (m, 5H), 5.76 (s, 1H), 3.57 (s, 2H), 2.97 (dt, J = 14.2, 5.8 Hz, 1H), 2.84-2.71 (m, 1H), 2.70-2.54 (m, 4H), 2.46 (td, J = 5.7, 4.7, 2.4 Hz, 2H), 1.13 (s, 9H). | 389 [M + H]⁺, 1.96 |

TABLE 6

| Amine Intermediate | Molecular Structure | Molecular Formula | MW | Name | ¹H-NMR | UPLC/MS [m/z, rt (min)] |
|---|---|---|---|---|---|---|
| 4 | (structure: 4-(2-fluorophenyl)-tetrahydropyran-4-amine) | $C_{11}H_{14}FNO$ | 195.11 | 4-(2-fluorophenyl)-tetrahydropyran-4-amine | ¹H NMR (400 MHz, CDCl₃) δ 7.37 (td, J = 8.2, 1.8 Hz, 1H), 7.29-7.22 (m, 2H), 7.19-7.11 (m, 1H), 7.11-7.03 (m, 1H), 4.04 (td, J = 11.2, 2.3 Hz, 2H), 2.26 (ddd, J = 13.8, 10.9, 4.5 Hz, 2H), 2.05-1.68 (m, 6H). | 196 [M + H]⁺, 1.11 |
| 5 | (structure: 4-amino-4-(2-fluorophenyl)-cyclohexanone) | $C_{12}H_{14}FNO$ | 207.10 | 4-amino-4-(2-fluorophenyl)-cyclohexanone | ¹H NMR (400 MHz, CDCl₃) δ 7.42 (ddd, J = 8.5, 7.7, 1.8 Hz, 1H), 7.28 (m, 1H), 7.16 (td, J = 7.6, 1.4 Hz, 1H), 7.10 (ddd, J = 13.1, 8.1, 1.3 Hz, 1H), 3.03-2.86 (m, 2H), 2.46-2.31 (m, 4H), 2.31-2.18 (m, 2H). | 208 [M + H]⁺, 1.11 |
| 6 | (structure: 1-benzyl-4-(2-fluorophenyl) piperidin-4-amine) | $C_{18}H_{21}FN_2$ | 284.16 | 1-benzyl-4-(2-fluorophenyl) piperidin-4-amine | ¹H NMR (400 MHz, CDCl₃) δ 7.46-7.19 (m, 7H), 7.12 (td, J = 7.6, 1.4 Hz, 1H), 7.05 (ddd, J = 13.2, 8.1, 1.4 Hz, 1H), 3.61 (s, 2H), 2.81-2.69 (m, 2H), 2.68-2.53 (m, 2H), 2.27 (td, J = 12.4, 11.3, 4.2 Hz, 2H), 2.04-1.84 (m, 2H). | 285 [M + H]⁺, 1.70 |

TABLE 7

| Molecular Structure | Molecular Formula | MW | Name | ¹H-NMR | UPLC/MS [m/z, rt (min)] |
|---|---|---|---|---|---|
| (structure: N-[4,4-difluoro-1-(2-fluorophenyl) cyclohexyl]-2-fluoro-acetamide) | $C_{14}H_{15}ClF_3NO$ | 305.08 | N-[4,4-difluoro-1-(2-fluorophenyl) cyclohexyl]-2-fluoro-acetamide | ¹H NMR (400 MHz, CDCl₃) δ 7.43 (td, J = 8.2, 1.8 Hz, 1H), 7.32-7.26 (m, 1H), 7.16 (td, J = 7.6, 1.3 Hz, 1H), 7.11-7.01 (m, 1H), 6.91 (s, 1H), 2.90-2.69 (m, 2H), 2.34-1.92 (m, 8H), 1.55 (s, 3H). | 306 [M + H]⁺, 2.43 |

TABLE 8

| Amine Intermediate | Molecular Structure | Molecular Formula | MW | Name | ¹H-NMR | UPLC/MS [m/z, rt (min)] |
|---|---|---|---|---|---|---|
| 7 | (structure) | C₁₂H₁₄F₃N | 229.11 | 4,4-difluoro-1-(2-fluorophenyl)cyclohexanamine | ¹H NMR (400 MHz, CDCl₃) δ 7.38 (ddd, J = 8.5, 7.7, 1.8 Hz, 1H), 7.31-7.23 (m, 1H), 7.14 (td, J = 7.6, 1.4 Hz, 1H), 7.07 (ddd, J = 13.2, 8.1, 1.4 Hz, 1H), 2.51-2.28 (m, 2H), 2.29-2.13 (m, 2H), 2.07-1.87 (m, 4H), 1.62 (bs, 2H). | 230 [M + H]⁺, 1.60 |

TABLE 9

| Molecular Structure | Molecular Formula | MW | Name | ¹H-NMR | UPLC/MS [m/z, rt (min)] |
|---|---|---|---|---|---|
| (structure) | C₁₄H₂₀N₂O₂ | 248.15 | methyl 3-[(4-methyl-piperazin-1-yl)-methyl]benzoate | ¹H NMR (400 MHz, DMSO-d₆) δ 7.89 (d, J = 1.7, Hz, 1H), 7.85 (dt, J = 7.6, 1.5 Hz, 1H), 7.57 (dt, J = 7.6, 1.5 Hz, 1H), 7.48 (t, J = 7.6 Hz, 1H), 3.86 (s, 3H), 3.52 (s, 2H), 2.47-2.19 (m, 8H), 2.15 (s, 3H). | 249 [M + H]⁺, 1.36 |
| (structure) | C₁₅H₂₂N₂O₃ | 278.16 | methyl 4-methoxy-3-[(4-methyl-piperazin-1-yl)methyl]benzoate | ¹H NMR (400 MHz, DMSO-d₆) δ 7.93 (d, J = 2.3, Hz, 1H), 7.87 (dd, J = 8.6, 2.3 Hz, 1H), 7.10 (d, J = 8.6 Hz, 1H), 3.86 (s, 3H), 3.82 (s, 3H), 3.48 (s, 2H), 2.48-2.27 (m, 8H), 2.18 (s, 3H). | 279 [M + H]⁺, 1.41 |

TABLE 10

| Molecular Structure | Molecular Formula | MW | Name | ¹H-NMR | UPLC/MS [m/z, rt (min)] |
|---|---|---|---|---|---|
| (structure) | C₁₃H₂₀N₂O | 220.16 | [3-[(4-methyl-piperazin-1-yl)methyl]phenyl]methanol | ¹H NMR (400 MHz, DMSO-d₆) δ 7.30-7.22 (m, 2H), 7.18 (dt, J = 7.5, 1.6 Hz, 1H), 7.14 (dt, J = 7.5, 1.6 Hz, 1H), 5.14 (t, J = 5.8 Hz, 1H), 4.48 (d, J = 5.7 Hz, 2H), 3.43 (s, 2H), 2.43-2.23 (m, 8H), 2.15 (s, 3H). | 221 [M + H]⁺, 0.97 |

TABLE 10-continued

| Molecular Structure | Molecular Formula | MW | Name | ¹H-NMR | UPLC/MS [m/z, rt (min)] |
|---|---|---|---|---|---|
| (structure: 4-methoxy-3-[(4-methylpiperazin-1-yl)methyl]phenyl methanol) | C₁₄H₂₂N₂O₂ | 250.17 | [4-methoxy-3-[(4-methyl-piperazin-1-yl)methyl]phenyl]methanol | ¹H NMR (400 MHz, DMSO-d₆) δ 7.93 (d, J = 2.3, Hz, 1H), 7.87 (dd, J = 8.6, 2.3 Hz, 1H), 7.10 (d, J = 8.6 Hz, 1H), 3.86 (s, 3H), 5.10 (t, J = 5.6 Hz, 1H), 4.50 (d, J = 5.6 Hz, 2H), 2.48-2.27 (m, 8H), 2.18 (s, 3H). | 251 [M + H]⁺, 1.08 |

TABLE 11

| Aldehyde Intermediate | Molecular Structure | Molecular Formula | MW | Name | ¹H-NMR | UPLC/MS [m/z, rt (min)] |
|---|---|---|---|---|---|---|
| 16 | (structure) | C₁₃H₁₈N₂O | 218.14 | 3-[(4-methylpiperazinlyl)methyl]benzaldehyde | ¹H NMR (400 MHz, DMSO-d₆) δ 10.02 (s, 1H), 7.85-7.77 (m, 2H), 7.64 (dt, J = 7.6, 1.5 Hz, 1H), 7.56 (t, J = 7.5 Hz, 1H), 3.55 (s, 2H), 2.45-2.23 (bm, 8H), 2.15 (s, 3H). | 219 [M + H]⁺, 1.16 |
| 17 | (structure) | C₁₄H₂₀N₂O₂ | 249.15 | 4-methoxy-3-[(4-methylpiperazin-1-yl)methyl]benzaldehyde | — | 249 [M + H]⁺, 1.20 |

TABLE 12

| Molecular Structure | Molecular Formula | MW | Name | ¹H-NMR | UPLC/MS [m/z, rt (min)] |
|---|---|---|---|---|---|
| (structure: Br⁻ Ph₃P⁺-CH₂-C₆H₄-CO₂Me) | C₂₇H₂₅O₂P | 491.08 | methyl 3-[(triphenyl-5-phosphanyl)methyl]benzoate bromide | ¹H NMR (400 MHz, CDCl₃) δ 7.90 (ddt, J = 7.9, 2.5, 1.3 Hz, 1H), 7.85-7.71 (m, 10H), 7.70-7.59 (m, 8H), 7.42 (q, J = 2.0 Hz, 1H), 5.60 (d, J = 14.5 Hz, 2H), 3.81 (s, 3H). | 411 [M]+, 2.29 |

TABLE 13

| Molecular Structure | Molecular Formula | MW | Name | ¹H-NMR | UPLC/MS [m/z, rt (min)] |
|---|---|---|---|---|---|
| 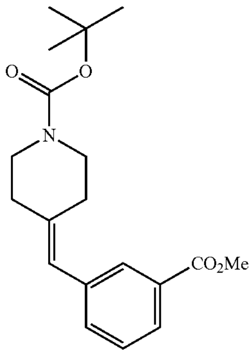 [SMILES: COC(=O)c1cccc(C=C2CCN(C(=O)OC(C)(C)C)CC2)c1] | $C_{19}H_{25}NO_4$ | 331.17 | tert-butyl 4-[(3-methoxycarbonylphenyl)methylene]piperidine-1-carboxylate | ¹H NMR (400 MHz, CDCl₃) δ 7.94-7.86 (m, 2H), 7.45-7.38 (m, 2H), 6.40 (s, 1H), 3.94 (s, 3H), 3.54 (dd, J = 6.9, 4.8 Hz, 2H), 3.50-3.39 (m, 2H), 2.52-2.42 (m, 2H), 2.42-2.30 (m, 2H), 1.50 (s, 9H). | 332 [M + H]⁺, 3.14 |

TABLE 14

| Molecular Structure | Molecular Formula | MW | Name | ¹H-NMR | UPLC/MS [m/z, rt (min)] |
|---|---|---|---|---|---|
| 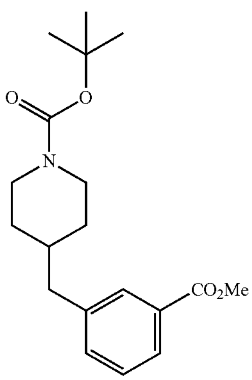 [SMILES: COC(=O)c1cccc(CC2CCN(C(=O)OC(C)(C)C)CC2)c1] | $C_{19}H_{27}NO_4$ | 333.19 | tert-butyl 4-[(3-methoxycarbonylphenyl)methyl]piperidine-1-carboxylate | ¹H NMR (400 MHz, CDCl₃) δ 7.90 (dt, J = 7.2, 1.8 Hz, 1H), 7.85 (t, J = 1.3 Hz, 1H), 7.41-7.33 (m, 2H), 3.94 (s, 3H), 2.66-2.63 (m, 2H), 2.61 (d, J = 7.1 Hz, 2H), 1.75-1.54 (m, 5H), 1.47 (s, 9H), 1.26-1.09 (m, 2H). | 334 [M + H]⁺, 3.14 |

TABLE 15

| Molecular Structure | Molecular Formula | MW | Name | ¹H-NMR | UPLC/MS [m/z, rt (min)] |
|---|---|---|---|---|---|
| 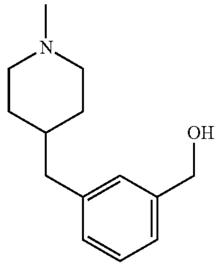 [SMILES: CN1CCC(Cc2cccc(CO)c2)CC1] | $C_{14}H_{21}NO$ | 219.16 | [3-[(1-methyl-4-piperidyl)methyl]phenyl]methanol | ¹H NMR (400 MHz, CDCl₃) δ 7.33-7.23 (m, 1H), 7.25-7.15 (m, 2H), 7.14-7.05 (m, 1H), 4.68 (s, 2H), 2.83 (dt, J = 11.6, 3.2 Hz, 2H), 2.56 (d, J = 7.0 Hz, 2H), 2.25 (s, 3H), 1.87 (td, J = 11.7, 2.6 Hz, 2H), 1.70-1.61 (m, 2H), 1.57-1.49 (m, 1H), 1.42-1.23 (m, 2H). | 220 [M + H]⁺, 1.18 |

TABLE 16

| Aldehyde Intermediate | Molecular Structure | Molecular Formula | MW | Name | $^1$H-NMR | UPLC/MS [m/z, rt (min)] |
|---|---|---|---|---|---|---|
| 18 | 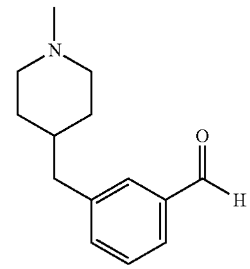 [SMILES: CN1CCC(Cc2cccc(C=O)c2)CC1] | $C_{14}H_{19}NO$ | 217.14 | 3-[(1-methyl-4-piperidyl)methyl]benzaldehyde | $^1$H NMR (400 MHz, CDCl$_3$) δ 10.03 (s, 1H), 7.74 (dt, J = 7.2, 1.6 Hz, 1H), 7.71-7.67 (m, 1H), 7.55-7.34 (m, 2H), 2.90 (dt, J = 11.9, 3.1 Hz, 2H), 2.66 (d, J = 6.9 Hz, 2H), 2.31 (s, 3H), 2.06-1.87 (m, 2H), 1.57 (dtt, J = 14.4, 7.0, 3.7 Hz, 1H), 1.49-1.31 (m, 2H). | 218 [M + H]$^+$, 1.35 |

TABLE 17

| Example | Molecular Structure | Molecular Formula | MW | Name |
|---|---|---|---|---|
| 21 | •2 HCl | $C_{24}H_{31}FN_2$•2HCl | 439.44 | 1-(2-fluorophenyl)-N-[[3-(1-piperidylmethyl)phenyl]methyl]cyclopentanamine dihydrochloride |
| 22 | •3 HCl | $C_{24}H_{32}FN_3O$•3HCl | 506.91 | 4-[[[1-(3-fluorophenyl)cyclopentyl]amino]methyl]-2-[(4-methylpiperazin-1-yl)methyl]phenol trihydrochloride |
| 23 | •3 HCl | $C_{24}H_{32}FN_3O$•3HCl | 506.91 | 4-[[[1-(4-fluorophenyl)cyclopentyl]amino]methyl]-2-[(4-methylpiperazin-1-yl)methyl]phenol trihydrochloride |
| 24 | •HCl | $C_{26}H_{34}FN$•HCl | 416.01 | 1-(2-fluorophenyl)-N-[[3-[(4-methylcyclohexyl)methyl]phenyl]methyl]cyclopentanamine hydrochloride (1:1 cis:trans ratio) |

TABLE 17-continued

| Example | Molecular Structure | Molecular Formula | MW | Name |
|---|---|---|---|---|
| 25 | 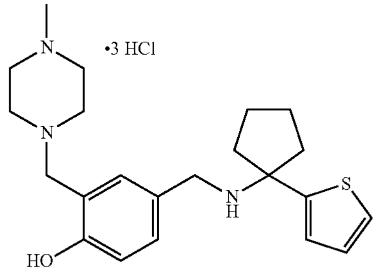 [SMILES: CN1CCN(Cc2cc(CNC3(c4cccs4)CCCC3)ccc2O)CC1 ; "·3 HCl"] | $C_{23}H_{31}N_3OS \cdot 3HCl$ | 494.94 | 2-[(4-methylpiperazin-1-yl)methyl]-4-[[[1-(2-thienyl)cyclopentyl]amino]methyl] phenol trihydrochloride |
| 26 | 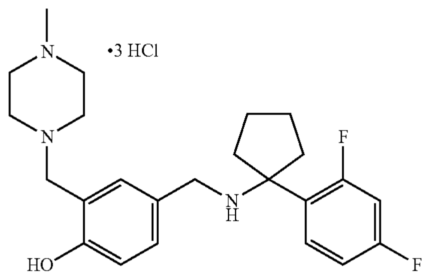 [SMILES: CN1CCN(Cc2cc(CNC3(c4ccc(F)cc4F)CCCC3)ccc2O)CC1 ; "·3 HCl"] | $C_{24}H_{31}F_2N_3O \cdot 3HCl$ | 524.90 | 4-[[[1-(2,4-difluorophenyl)cyclopentyl]amino]methyl]-2-[(4-methylpiperazin-1-yl)methyl] phenol trihydrochloride |
| 27 | 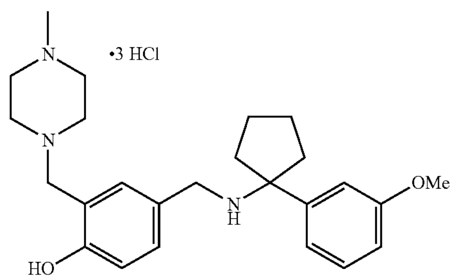 [SMILES: COc1cccc(C2(NCc3ccc(O)c(CN4CCN(C)CC4)c3)CCCC2)c1 ; "·3 HCl"] | $C_{25}H_{35}N_3O_2 \cdot 3HCl$ | 518.94 | 4-[[[1-(3-methoxyphenyl)cyclopentyl]amino]methyl]-2-[(4-methylpiperazin-1-yl)methyl]phenol trihydrochloride |
| 28 | 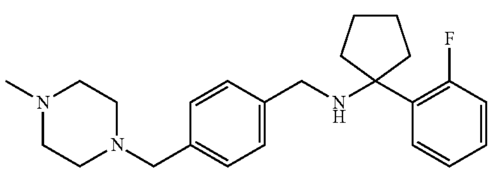 | $C_{24}H_{32}FN_3 \cdot 3HCl$ | 490.91 | 1-(2-fluorophenyl)-N-[[4-[(4-methylpiperazin-1-yl)methyl]phenyl]methyl]cyclopentanamine trihydrochloride |
| 29 | 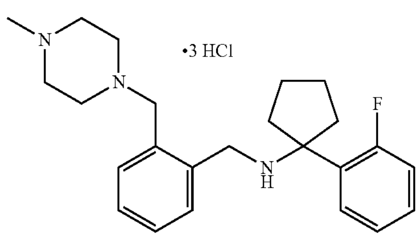 [SMILES: CN1CCN(Cc2ccccc2CNC2(c3ccccc3F)CCCC2)CC1 ; "·3 HCl"] | $C_{24}H_{32}FN_3 \cdot 3HCl$ | 490.91 | 1-(2-fluorophenyl)-N-[[2-[(4-methylpiperazin-1-yl)methyl]phenyl]methyl]cyclopentanamine trihydrochloride |
| 30 | 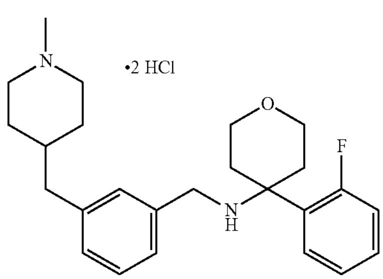 [SMILES: CN1CCC(Cc2cccc(CNC3(c4ccccc4F)CCOCC3)c2)CC1 ; "·2 HCl"] | $C_{25}H_{33}FN_2O \cdot 2HCl$ | 469.46 | 4-(2-fluorophenyl)-N-[[3-[(1-methyl-4-piperidyl)methyl]phenyl]methyl]tetrahydropyran-4-amine dihydrochloride |

TABLE 17-continued

| Example | Molecular Structure | Molecular Formula | MW | Name |
|---|---|---|---|---|
| 31 | 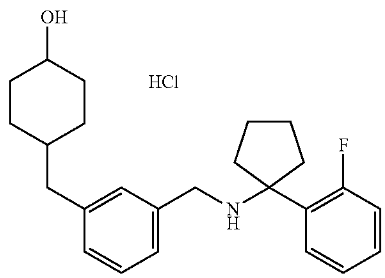 [SMILES: OC1CCC(Cc2cccc(CNC3(c4ccccc4F)CCCC3)c2)CC1 ; Cl] | $C_{25}H_{32}FNO \cdot 2HCl$ | 417.98 | 4-[[3-[[[1-(2-fluorophenyl)-cyclopentyl]amino]methyl]phenyl]methyl]cyclohexanol hydrochloride |
| 32 | 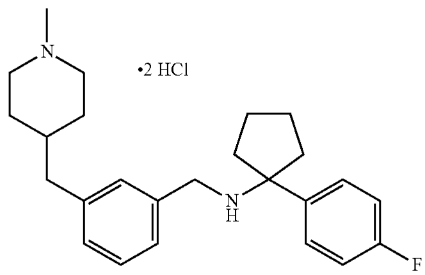 [SMILES: CN1CCC(Cc2cccc(CNC3(c4ccc(F)cc4)CCCC3)c2)CC1 ; "·2 HCl"] | $C_{25}H_{33}FN_2 \cdot 2HCl$ | 453.46 | 1-(4-fluorophenyl)-N-[[3-[(1-methyl-4-piperidyl)methyl]phenyl]methyl]cyclopentanamine dihydrochloride |
| 33 | 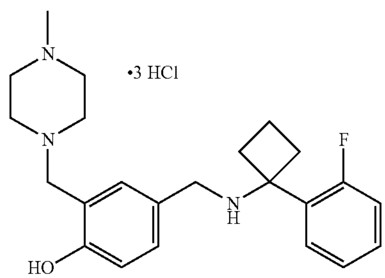 [SMILES: CN1CCN(Cc2cc(CNC3(c4ccccc4F)CCC3)ccc2O)CC1 ; "·3 HCl"] | $C_{23}H_{30}FN_3O \cdot 3HCl$ | 492.88 | 4-[[[1-(2-fluorophenyl)cyclobutyl]amino]methyl]-2-[(4-methylpiperazin-1-yl)methyl]phenol trihydrochloride |

TABLE 18

| Molecular Structure | Molecular Formula | MW | Name | $^1$H-NMR | UPLC/MS [m/z, rt (min)] |
|---|---|---|---|---|---|
| | $C_{11}H_{13}FO$ | 180.22 | 1-(3-fluorophenyl)cyclopentanol | $^1$H NMR (400 MHz, CDCl$_3$) δ 7.36-7.30 (m, 1H), 7.29-7.21 (m, 2H), 6.96 (tdd, J = 8.0, 2.6, 1.2 Hz, 1H), 2.09-1.93 (m, 6H), 1.93-1.80 (m, 2H). | 163 [M − OH]$^+$, 2.28 |
| | $C_{11}H_{13}FO$ | 180.22 | 1-(4-fluorophenyl)cyclopentanol | $^1$H NMR (400 MHz, CDCl$_3$) δ 7.84-7.34 (m, 2H), 7.17-6.84 (m, 2H), 2.05-1.95 (m, 6H), 1.93-1.80 (m, 2H). | — |

TABLE 18-continued

| Molecular Structure | Molecular Formula | MW | Name | ¹H-NMR | UPLC/MS [m/z, rt (min)] |
|---|---|---|---|---|---|
| 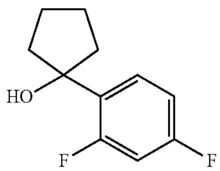 [SMILES: OC1(c2ccc(F)cc2F)CCCC1] | $C_{11}H_{12}F_2O$ | 198.21 | 1-(2,4-difluorophenyl)cyclopentanol | ¹H NMR (400 MHz, CDCl$_3$) δ 7.08-6.98 (m, 1H), 6.93-6.85 (m, 1H), 6.70 (tt, J = 8.8, 2.3 Hz, 1H), 2.41-2.30 (m, 2H), 2.24-2.09 (m, 2H), 2.09-1.72 (m, 4H). | — |
| 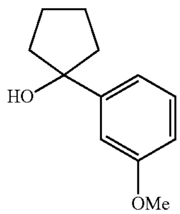 [SMILES: COc1cccc(C2(O)CCCC2)c1] | $C_{12}H_{16}O_2$ | 192.25 | 1-(3-methoxyphenyl)cyclopentanol | ¹H NMR (400 MHz, CDCl$_3$) δ 7.38-7.27 (m, 1H), 7.22 (ddd, J = 8.1, 7.4, 1.8 Hz, 1H), 7.00-6.85 (m, 2H), 6.44 (m, 1H), 3.90 (s, 3H), 2.84-2.74 (m, 2H), 2.58 (m, 2H), 2.06-1.92 (m, 4H). | 175 [M − OH]⁺, 2.37 |
| 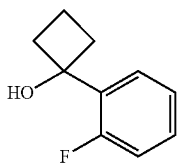 [SMILES: OC1(c2ccccc2F)CCC1] | $C_{10}H_{11}FO$ | 166.19 | 1-(2-fluorophenyl)cyclobutanol | ¹H NMR (400 MHz, CDCl$_3$) δ 7.39 (td, J = 7.8, 1.8 Hz, 1H), 7.34-7.26 (m, 1H), 7.16 (td, J = 7.5, 1.2 Hz, 1H), 7.09 (ddd, J = 11.4, 8.1, 1.2 Hz, 1H), 2.72-2.63 (m, 2H), 2.46-2.35 (m, 2H), 2.25-2.07 (m, 1H), 1.82-1.71 (m, 1H). | 149 [M − OH]⁺, 1.99 |

TABLE 19

| Molecular Structure | Molecular Formula | MW | Name | ¹H-NMR |
|---|---|---|---|---|
| | $C_{11}H_{12}FN_3$ | 205.23 | 1-(1-azidocyclopentyl)-3-fluoro-benzene | ¹H NMR (400 MHz, CDCl$_3$) δ 7.37 (td, J = 8.0, 6.0 Hz, 1H), 7.22 (ddd, J = 7.8, 1.8, 1.0 Hz, 1H), 7.18-7.11 (m, 1H), 7.03 (tdd, J = 8.3, 2.6, 1.0 Hz, 1H), 2.36-2.15 (m, 2H), 2.06-1.78 (m, 6H). |
| | $C_{11}H_{12}FN_3$ | 205.23 | 1-(1-azidocyclopentyl)-4-fluoro-benzene | ¹H NMR (400 MHz, CDCl$_3$) δ 7.51-7.36 (m, 2H), 7.16-6.99 (m, 2H), 2.29-2.20 (m, 2H), 2.07-1.80 (m, 6H). |
| 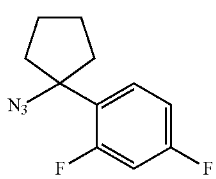 [SMILES: [N-]=[N+]=NC1(c2ccc(F)cc2F)CCCC1] | $C_{11}H_{11}F_2N_3$ | 223.32 | 1-(1-azidocyclopentyl)-2,4-difluoro-benzene | ¹H NMR (400 MHz, CDCl$_3$) δ 7.19-7.12 (m, 1H), 6.98-6.87 (m, 1H), 6.77 (tt, J = 8.6, 2.3 Hz, 1H), 2.37-2.25 (m, 1H), 2.15-1.98 (m, 4H), 1.96-1.79 (m, 1H). |
| 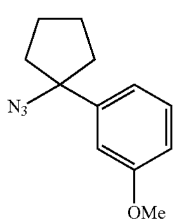 [SMILES: COc1cccc(C2(N=[N+]=[N-])CCCC2)c1] | $C_{12}H_{15}N_3O$ | 217.27 | 1-(1-azidocyclopentyl)-3-methoxy-benzene | ¹H NMR (400 MHz, CDCl$_3$) δ 7.35-7.30 (m, 1H), 7.27-7.20 (m, 1H), 6.99-6.90 (m, 2H), 3.62 (s, 3H), 2.08-1.89 (m, 2H), 1.89-1.66 (m, 6H). |

TABLE 19-continued

| Molecular Structure | Molecular Formula | MW | Name | ¹H-NMR |
|---|---|---|---|---|
| (N₃-cyclobutyl-2-fluorophenyl) | $C_{10}H_{10}FN_3$ | 191.20 | 1-(1-azidocyclobutyl)-2-fluoro-benzene | ¹H NMR (400 MHz, CDCl₃) δ 7.37-7.30 (m, 1H), 7.28-7.23 (m, 1H), 7.18 (td, J = 7.5, 1.2 Hz, 1H), 7.11 (ddd, J = 10.8, 8.2, 1.2 Hz, 1H), 2.76-2.63 (m, 2H), 2.59-2.50 (m, 2H), 2.39-2.32 (m, 1H), 1.90 (dtt, J = 11.2, 8.8, 4.3 Hz, 1H). |

TABLE 20

| Amine Intermediate | Molecular Structure | Molecular Formula | MW | Name | ¹H-NMR | UPLC/MS [m/z, rt (min)] |
|---|---|---|---|---|---|---|
| 19 | H₂N-cyclopentyl-(3-fluorophenyl) | $C_{11}H_{14}FN$ | 179.11 | 1-(3-fluorophenyl)cyclopentanamine | ¹H NMR (400 MHz, CDCl₃) δ 7.35-7.29 (m, 1H), 7.28-7.23 (m, 1H), 7.19 (dt, J = 10.8, 2.2 Hz, 1H), 6.93 (ddt, J = 8.6, 7.1, 1.3 Hz, 1H), 2.10-1.91 (m, 4H), 1.98-1.75 (m, 4H), 1.67-1.47 (m, 2H). | 180 [M + H]⁺, 1.18 |
| 20 | H₂N-cyclopentyl-(4-fluorophenyl) | $C_{11}H_{14}FN$ | 179.11 | 1-(4-fluorophenyl)cyclopentanamine | ¹H NMR (400 MHz, CDCl₃) δ 7.50-7.40 (m, 2H), 7.08-6.94 (m, 2H), 2.08-1.75 (m, 8H). | 180 [M]⁺, 1.45 |
| 21 | H₂N-cyclopentyl-(2-thienyl) | $C_9H_{13}NS$ | 167.14 | 1-(2-thienyl)cyclopentanamine | ¹H NMR (400 MHz, CDCl₃) δ 7.18 (dd, J = 4.1, 2.3 Hz, 1H), 6.98-6.93 (m, 2H), 2.19-2.01 (m, 2H), 2.01-1.78 (m, 6H). | 168 [M + H]⁺, 1.29 |
| 22 | H₂N-cyclopentyl-(2,4-difluorophenyl) | $C_{11}H_{13}F_2N$ | 197.12 | 1-(2,4-fluorophenyl)cyclopentanamine | ¹H NMR (400 MHz, CDCl₃) δ 7.18 (dd, J = 4.1, 2.3 Hz, 1H), 6.98-6.93 (m, 2H), 2.19-2.01 (m, 2H), 2.01-1.78 (m, 6H). | 198 [M + H]⁺, 1.41 |
| 23 | H₂N-cyclopentyl-(3-methoxyphenyl) | $C_{12}H_{17}NO$ | 191.18 | 1-(3-methoxyphenyl)cyclopentanamine | ¹H NMR (400 MHz, CDCl₃) δ 7.31-7.21 (m, 1H), 7.08-7.00 (m, 2H), 6.77 (ddd, J = 8.3, 2.4, 1.0 Hz, 1H), 3.82 (s, 3H), 2.07-1.85 (m, 6H), 1.85-1.71 (m, 2H). | 192 [M + H]⁺, 1.45 |
| 24 | H₂N-cyclobutyl-(2-fluorophenyl) | $C_{11}H_{14}FN$ | 165.11 | 1-(2-fluorophenyl)-cyclobutanamine | ¹H NMR (400 MHz, CDCl₃) δ 7.25-7.16 (m, 2H), 7.09 (td, J = 7.5, 1.2 Hz, 1H), 7.01 (ddd, J = 11.3, 8.1, 1.2 Hz, 1H), 2.67-2.47 (m, 2H), 2.31-2.14 (m, 3H), 1.90-1.72 (m, 1H). | 166 [M + H]⁺, 1.27 |

TABLE 21

| Molecular Structure | Molecular Formula | MW | Name | ¹H-NMR | UPLC/MS [m/z, rt (min)] |
|---|---|---|---|---|---|
| (piperidine-CH₂-C₆H₄-CO₂Me, meta) | $C_{14}H_{19}NO_2$ | 233.30 | methyl 3-(1-piperidylmethyl)benzoate | ¹H NMR (400 MHz, CDCl₃) δ 8.02-7.96 (m, 2H), 7.70-7.63 (m, 1H), 7.46 (t, J = 8.1 Hz, 1H), 3.95 (s, 3H), 3.71 (s, 2H), 2.68-2.45 (m, 4H), 1.75-1.63 (m, 4H), 1.55-1.43 (m, 2H). | 234 [M + H]⁺, 1.40 |
| (4-methylpiperazine-CH₂-C₆H₄-CO₂Me, para) | $C_{14}H_{20}N_2O_2$ | 248.30 | methyl 4-[(4-methylpiperazin-1-yl)methyl]benzoate | — | 249 [M + H]⁺, 1.37 |
| (4-methylpiperazine-CH₂-C₆H₄-CO₂Me, ortho) | $C_{14}H_{20}N_2O_2$ | 248.30 | methyl 2-[(4-methylpiperazin-1-yl)methyl]benzoate | ¹H NMR (400 MHz, CDCl₃) δ 7.74 (dd, J = 7.5, 1.3 Hz, 1H), 7.48-7.39 (m, 2H), 7.34 (td, J = 7.3, 1.9 Hz, 1H), 3.90 (s, 1H), 2.90-2.55 (m, 8H), 2.49 (s, 3H). | 249 [M + H]⁺, 1.46 |

TABLE 22

| Molecular Structure | Molecular Formula | MW | Name | ¹H-NMR | UPLC/MS [m/z, rt (min)] |
|---|---|---|---|---|---|
| (piperidine-CH₂-C₆H₄-CH₂OH, meta) | $C_{13}H_{19}NO$ | 205.30 | [3-(1-piperidylmethyl)phenyl]methanol | ¹H NMR (400 MHz, CDCl₃) δ 7.44-7.36 (m, 1H), 7.36-7.27 (m, 3H), 4.73 (s, 2H), 3.56 (s, 2H), 2.54-2.38 (m, 4H), 1.70-1.58 (m, 4H), 1.53-1.43 (m, 2H). | 206 [M + H]⁺, 0.98 |
| (4-methylpiperazine-CH₂-C₆H₄-CH₂OH, para) | $C_{13}H_{20}N_2O$ | 220.30 | [4-[(4-methylpiperazin-1-yl)methyl]phenyl]methanol | — | 221 [M + H]⁺, 0.90 |
| (4-methylpiperazine-CH₂-C₆H₄-CH₂OH, ortho) | $C_{13}H_{20}N_2O$ | 220.30 | [2-[(4-methylpiperazin-1-yl)methyl]phenyl]methanol | — | 221 [M + H]⁺, 0.90 |

TABLE 23

| Aldehyde Intermediate | Molecular Structure | Molecular Formula | MW | Name | ¹H-NMR | UPLC/MS [m/z, rt (min)] |
|---|---|---|---|---|---|---|
| 25 | 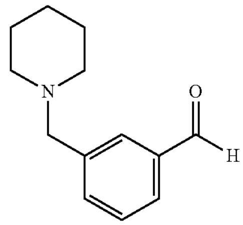 [SMILES: O=Cc1cccc(CN2CCCCC2)c1] | $C_{13}H_{17}NO$ | 203.13 | 3-(1-piperidyl methyl) benzaldehyde | ¹H NMR (400 MHz, CDCl₃) δ 10.05 (s, 1H), 7.87-7.85 (m, 1H), 7.79 (dt, J = 7.5, 1.5 Hz, 1H), 7.64 (d, J = 7.6 Hz, 1H), 7.50 (t, J = 7.6 Hz, 1H), 3.56 (s, 2H), 2.41 (bs, 4H), 1.67-1.65 (m, 4H), 1.50-1.44 (m, 2H). | 204 [M + H]⁺, 1.12 |
| 26 | 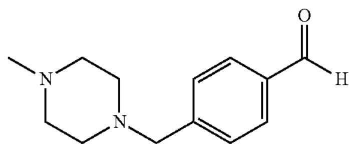 [SMILES: CN1CCN(Cc2ccc(C=O)cc2)CC1] | $C_{13}H_{18}N_2O$ | 218.14 | 4-[(4-methylpiperazin-1-yl)methyl] benzaldehyde | — | 219 [M + H]⁺, 1.10 |
| 27 | 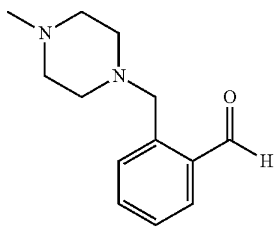 [SMILES: CN1CCN(Cc2ccccc2C=O)CC1] | $C_{13}H_{18}N_2O$ | 218.14 | 2-[(4-methyl piperazin-1-yl)methyl] benzaldehyde | ¹H NMR (400 MHz, CDCl₃) δ 10.40 (s, 1H), 7.90 (dd, J = 7.6, 1.5 Hz, 1H), 7.61-7.52 (m, 1H), 7.48 (t, J = 7.5 Hz, 1H), 7.41-7.35 (m, 1H), 3.71 (s, 2H), 2.45-2.26 (bs, 8H), 2.18 (s, 3H). | 219 [M + H]⁺, 1.26 |

TABLE 24

| Molecular Structure | Molecular Formula | MW | Name | ¹H-NMR | UPLC/MS [m/z, rt (min)] |
|---|---|---|---|---|---|
| 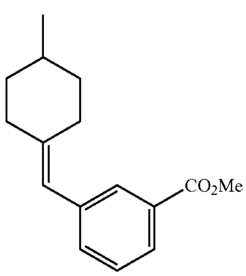 [SMILES: COC(=O)c1cccc(C=C2CCC(C)CC2)c1] | $C_{16}H_{20}O_2$ | 244.30 | methyl 3-[(4-methylcyclohexylidene) methyl]benzoate | ¹H NMR (400 MHz, CDCl₃) δ 7.93-7.83 (m, 2H), 7.43-7.37 (m, 2H), 6.27 (s, 1H), 3.93 (s, 3H), 2.88-2.72 (m, 1H), 2.42-2.33 (m, 1H), 2.30-2.19 (m, 1H), 2.04-1.91 (m, 1H), 1.87 (dddd, J = 13.7, 6.6, 3.5, 2.1 Hz, 1H), 1.82-1.73 (m, 1H), 1.71-1.58 (m, 1H), 1.15 (tdd, J = 12.7, 11.1, 4.2 Hz, 1H), 1.04 (tdd, J = 12.9, 11.2, 4.0 Hz, 1H), 0.95 (d, J = 6.5 Hz, 3H). | 2.40 Not ionizable |
| * | $C_{17}H_{20}O_4$ | 274.30 | 3-(1,4-dioxaspiro[4.5] decan-8-ylidene methyl)benzoic acid | ¹H NMR (400 MHz, CDCl₃) δ 8.03-7.90 (m, 2H), 7.51-7.43 (m, 2H), 6.36 (s, 1H), 4.02 (s, 4H), 2.85-2.77 (m, 1H), 2.78-2.68 (m, 1H), 2.62-2.52 (m, 2H), 2.52-2.40 (m, 1H), 2.10-1.99 (m, 1H), 1.86-1.82 (m, 1H), 1.75-1.72 (m, 1H). | 275 [M + H]⁺, 1.84 |

* This intermediate was synthesized following the general procedure for the synthesis of aldehydes of Formula IIc, with a slight modification in step 2 in which were used as starting material methyl 3-(dimethoxyphosphorylmethyl)benzoate and 1,4-dioxaspiro[4.5]decan-8-one in the presence of NaH (4.0 equiv.) as base.

TABLE 25

| Molecular Structure | Molecular Formula | MW | Name | $^1$H-NMR | UPLC/MS [m/z, rt (min)] |
|---|---|---|---|---|---|
| (4-methylcyclohexylmethyl benzoate structure, CO₂Me) | $C_{16}H_{22}O_2$ | 246.30 | methyl 3-[(4-methylcyclohexyl)methyl] benzoate (1:1 cis:trans ratio) | $^1$H NMR (400 MHz, CDCl$_3$) δ 8.01-7.68 (m, 4H), 7.51-7.26 (m, 4H), 3.93 (s, 6H), 2.64 (d, J = 7.5 Hz, 2H), 2.55 (d, J = 7.1 Hz, 2H), 1.82-1.73 (m, 2H), 1.73-1.63 (m, 4H), 1.56-1.42 (m, 8H),1.41-1.24 (m, 6H), 0.96 (d, J = 6.9 Hz, 3H), 0.88 (d, J = 6.6 Hz, 3H). | 2.41 Not ionizable |
| (dioxaspiro decane methyl benzoic acid structure, CO₂H) | $C_{16}H_{20}O_4$ | 276.30 | 3-(1,4-dioxaspiro [4.5]decan-8-ylmethyl) benzoic acid | $^1$H NMR (400 MHz, CDCl$_3$) δ 7.97-7.92 (m, 1H), 7.90 (s, 1H), 7.46-7.38 (m, 2H), 3.96 (s, 4H), 2.62 (d, J = 6.9 Hz, 2H), 1.80-1.66 (m, 4H), 1.65-1.57 (m, 1H), 1.52 (td, J = 13.1, 3.8 Hz, 2H), 1.40-1.25 (m, 2H). | 277 [M + H]⁺, 1.90 |

TABLE 26

| Molecular Structure | Molecular Formula | MW | Name | $^1$H-NMR |
|---|---|---|---|---|
| (4-methylcyclohexylmethyl phenylmethanol structure, OH) | $C_{15}H_{22}O$ | 218.30 | [3-[(4-methyl cyclohexyl)methyl] phenyl]methanol (1:1 cis:trans ratio) | $^1$H NMR (400 MHz, CDCl$_3$) δ 7.33-7.26 (m, 2H), 7.25-7.17 (m, 4H), 7.15-7.07 (m, 2H), 4.70 (s, 4H), 2.61 (d, J = 7.5 Hz, 2H), 2.51 (d, J = 7.1 Hz, 2H), 1.81-1.65 (m, 4H), 1.63-1.53 (m, 4H), 1.52-1.43 (m, 4H), 1.43-1.25 (m, 8H), 0.96 (d, J = 6.8 Hz, 3H), 0.88 (d, J = 6.5 Hz, 3H). |
| (4-hydroxycyclohexylmethyl phenyl methanol structure, OH, OH) | $C_{14}H_{20}O_2$ | 220.30 | 4-[[3-(hydroxyl methyl)phenyl] methyl] cyclohexanol | $^1$H NMR (400 MHz, CDCl$_3$) δ 7.33-7.29 (m, 1H), 7.25-7.19 (m, 1H), 7.17 (s, 1H), 7.12-7.07 (m, 1H), 3.59 (tt, J = 10.8, 4.3 Hz, 1H), 2.52 (d, J = 7.1 Hz, 2H), 2.05-1.90 (m, 2H), 1.84-1.69 (m, 2H), 1.60-1.42 (m, 2H), 1.34-1.17 (m, 2H), 1.13-0.93 (m, 2H). |

TABLE 27

| Aldehyde Intermediate | Molecular Structure | Molecular Formula | MW | Name | ¹H-NMR | UPLC/MS [m/z, rt (min)] |
|---|---|---|---|---|---|---|
| 28 | 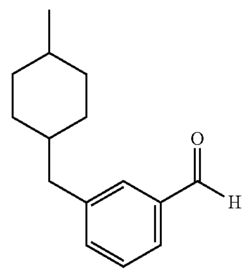 [SMILES: CC1CCC(Cc2cccc(C=O)c2)CC1] | $C_{14}H_{19}NO$ | 216.15 | 3-[(4-methylcyclohexyl)methyl]benzaldehyde (1:1 cis:trans ratio) | ¹H NMR (400 MHz, CDCl₃) δ 10.03 (s, 2H), 7.79-7.64 (m, 4H), 7.52-7.38 (m, 4H), 2.68 (d, J = 7.5 Hz, 2H), 2.59 (d, J = 7.1 Hz, 2H), 1.86-1.74 (m, 1H), 1.74-1.63 (m, 4H), 1.55-1.43 (m, 6H), 1.43-1.25 (m, 6H), 1.09-0.92 (m, 3H), 0.96 (d, J = 4.0 Hz, 3H), 0.87 (d, J = 4.0 Hz, 3H). | Rt 2.07 min, not ionizable |
| 29 | 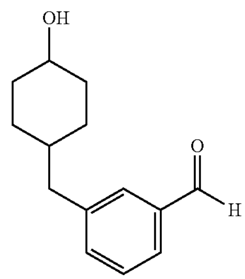 [SMILES: O=Cc1cccc(CC2CCC(O)CC2)c1] | $C_{14}H_{18}O_2$ | 218.13 | 3-[(4-hydroxycyclohexyl)methyl]benzaldehyde | ¹H NMR (400 MHz, CDCl₃) δ 10.03 (s, 1H), 7.73 (dt, J = 7.5, 1.6 Hz, 1H), 7.71-7.66 (m, 1H), 7.50-7.41 (m, 2H), 3.59 (tt, J = 10.8, 4.3 Hz, 1H), 2.60 (d, J = 7.2 Hz, 2H), 2.04-1.92 (m, 2H), 1.81-1.69 (m, 2H), 1.55-1.53 (m, 2H), 1.31-1.19 (m, 2H), 1.16-0.96 (m, 2H). | Rt 2.06 min, not ionizable |

The invention claimed is:

1. A compound of Formula (I) or a pharmaceutically acceptable salt or solvate thereof:

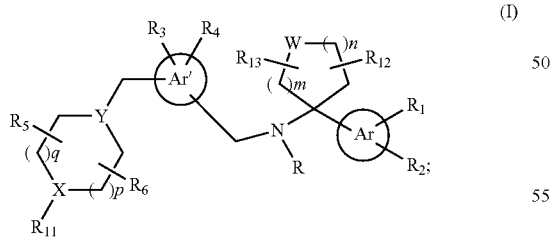

(I)

wherein Ar and Ar' are independently selected from the group consisting of a 5- to 10-membered aromatic and heteroaromatic single or fused rings comprising up to 3 heteroatoms selected from N, O and S;

R is selected from the group consisting of hydrogen, a linear or branched unsubstituted or substituted $C_{1-6}$ alkyl and an unsubstituted or substituted aryl $C_{1-6}$ alkyl;

$R_1$, $R_2$, $R_3$ and $R_4$ are independently selected from the group consisting of H, halogen, linear or branched, unsubstituted or substituted $C_{1-6}$ alkyl, $C_{1-6}$ alkoxy, hydroxy $C_{1-6}$ alkyl, OH, CN, fluoro $C_{1-6}$ alkyl and fluoro $C_{1-6}$ alkoxy; $R_1$, $R_2$, $R_3$ and $R_4$ can be attached to any position of Ar and Ar' group, respectively;

Y is selected from the group consisting of N and CH;

X is selected from the group consisting of CH and N;

$R_5$ and $R_6$ are independently selected from the group consisting of H, halogen, unsubstituted or substituted linear or branched $C_{1-6}$ alkyl, =O, unsubstituted or substituted aryl, unsubstituted or substituted aryl $C_{1-6}$ alkyl, hydroxy $C_{1-6}$ alkyl, $C_{1-6}$ alkylCO, unsubstituted or substituted arylCO, unsubstituted or substituted aryl $C_{1-6}$ alkylCO, $COOR_7$, $CONR_8R_9$ and $SO_2R_{10}$ wherein $R_7$, $R_8$, $R_9$, and $R_{10}$ are independently selected from the group consisting of hydrogen and linear or branched $C_{1-6}$ alkyl; $R_5$ and $R_6$ can be attached to any carbon atom of the ring to which they are connected and they may be connected to the same carbon atom or to different carbon atoms of the ring; and $R_{11}$ is selected from the group consisting of H, linear or branched $C_{1-6}$ alkyl, $C_{1-6}$ alkylCO, aryl and aryl $C_{1-6}$ alkyl;

or $R_5$ and $R_6$, or $R_5$ and $R_{11}$ or $R_6$ and $R_{11}$ are linked together to form an unsubstituted or substituted 4- to 10-membered ring, saturated or unsaturated, and containing up to two nitrogen atoms;

q and p are, independently, 0 or an integer from 1 to 2 with the proviso that when both Y and X are N, neither q and p are 0;

$R_{12}$ and $R_{13}$ are independently selected from the group consisting of H, F, $C_{1-6}$ alkyl, $C_{1-6}$ alkyl-OH, =O, OH, COOH, $CO_2Me$, $CONH_2$, CONHMe and $CONMe_2$ and can be attached to any position of the ring to which they are connected and they may be connected to the same carbon atom or to different carbon atoms of the ring;

W is selected from the group consisting of a bond and a heteroatom selected from the group consisting of O, S and $NR_{14}$, wherein $R_{14}$ is selected from the group consisting of H, linear or branched $C_{1-6}$ alkyl, $C_{1-6}$ alkylCO, unsubstituted or substituted aryl, unsubstituted or substituted aryl $C_{1-6}$ alkyl, unsubstituted or substituted arylCO, $SO_2R_{15}$, $CONR_{16}R_{17}$ and $COOR_{18}$, wherein $R_{15}$, $R_{16}$, $R_{17}$ and $R_{18}$ are independently selected from the group consisting of H and linear or branched $C_{1-6}$ alkyl;

m is an integer from 1 to 3, n is 0 or an integer from 1 to 3 with the proviso that when W is bond, n is not 0;

provided that the compound of Formula (I) is not:

4-[[[1-(4-methoxyphenyl)cyclopentyl]amino]methyl]-2-[(4-methyl-1-piperazinyl)methyl]-phenol;

4-[[[1-(2-fluorophenyl)cyclopentyl]amino]methyl]-2-[(4-methyl-1-piperazinyl)methyl]-phenol or 4-[[[1-(2-methoxyphenyl)cyclopentyl]amino]methyl]-2-[(4-methyl-1-piperazinyl)methyl]-phenol.

2. The compound according to claim 1 wherein:

Ar and Ar' are, independently, selected from benzene, pyridine, naphthalene and thiophene rings;

R is selected from the group consisting of H, $CH_3$ and unsubstituted or substituted phenyl$CH_2$;

$R_1$, $R_2$, $R_3$ and $R_4$ are independently selected from the group consisting of H, F, Cl, $CH_3$, OH, $OCH_3$, $CH_2OH$, $CF_3$, $CHF_2$, $CH_2F$, $CF_2CF_3$, $OCF_3$, $OCF_2CF_3$ and CN;

$R_5$ and $R_6$ are independently selected from the group consisting of H, F, $CH_3$, =O, unsubstituted or substituted phenyl, unsubstituted or substituted pyridyl, unsubstituted or substituted phenyl$CH_2$, $CH_2OH$, $CH_3CO$, unsubstituted or substituted phenylCO, unsubstituted or substituted phenyl$CH_2CO$, $COOR_7$, $CONR_8R_9$ and $SO_2R_{10}$ wherein $R_7$, $R_8$, $R_9$, and $R_{10}$ are independently selected from the group consisting of H and $CH_3$;

$R_{11}$ is selected from the group consisting of H, $CH_3$, Et, i-Pr, phenyl$C_{1-6}$ alkyl, $CH_3CO$ and phenyl;

or $R_5$ and $R_6$, or $R_5$ and $R_{11}$ or $R_6$ and $R_{11}$ are linked together to form a ring and thus the moiety:

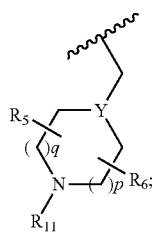

has a meaning selected from the group consisting of:

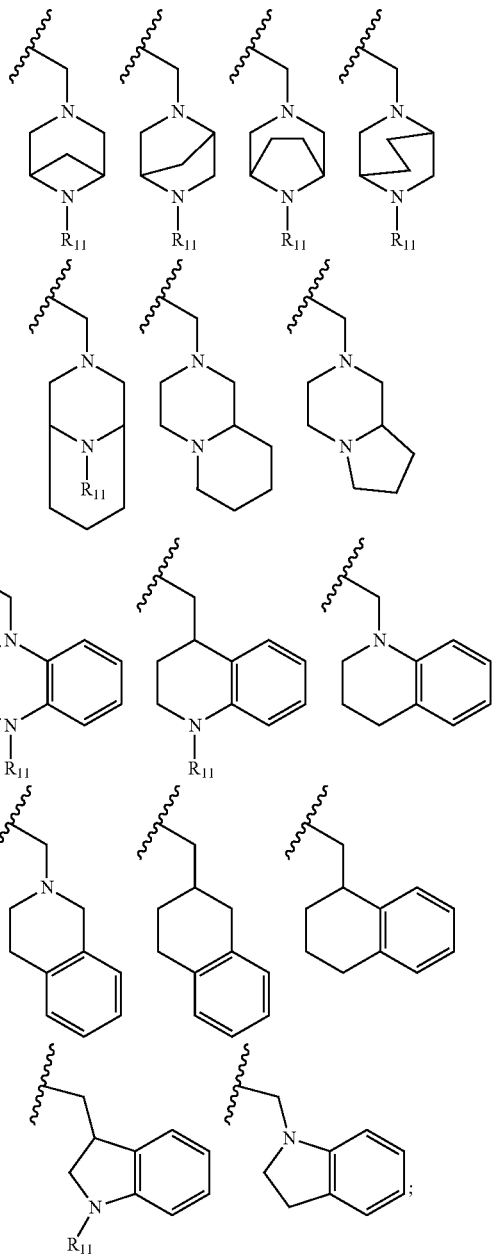

p and q are, independently, 0 or 1;

$R_{12}$ and $R_{13}$ are independently selected from the group consisting of H, F, $CH_3$, $CH_2OH$, OH and =O, and are connected to the same carbon atom or to different carbon atoms of the ring;

W is selected from the group consisting of a bond and a heteroatom selected from the group consisting of O and $NR_{14}$, wherein $R_{14}$ is H, $CH_3$, $COCH_3$, unsubstituted or substituted phenyl, unsubstituted or substituted phenyl $CH_2$, unsubstituted or substituted phenylCO, $SO_2R_{15}$, $CONR_{16}R_{17}$ and $COOR_{18}$, wherein $R_{15}$, $R_{16}$, $R_{17}$ and $R_{18}$ are independently selected from the group consisting of H and $CH_3$;

m is an integer from 1 to 3, and n is an integer from 1 to 2.

3. The compound according to claim 1 wherein W is selected from the group consisting of a bond, O, NH, NCH$_3$, NCOCH$_3$ and NCH$_2$phenyl.

4. The compound according to claim 1, having the Formula (I'):

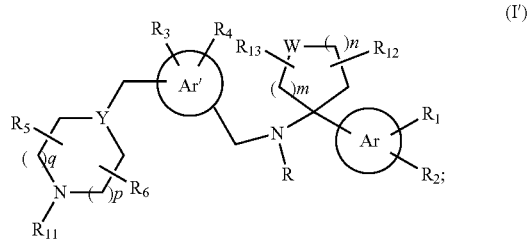

wherein:
Ar and Ar' are, independently, selected from benzene, pyridine, naphthalene and thiophene rings;
R is selected from the group consisting of H and CH$_3$;
R$_1$ and R$_3$ are independently selected from the group consisting of H, F, CH$_3$, OCH$_3$, OH, CF$_3$ and CN;
R$_2$ and R$_4$ are, independently, H or F;
p and q are equal to 1, m is an integer from 1 to 2, n is an integer from 1 to 2;
R$_{12}$ and R$_{13}$ are independently selected from the group consisting of H, F, CH$_3$, CH$_2$OH, =O and OH, and they are connected to the same carbon atom or to different carbon atoms of the ring;
W is a bond, O, NH, NCH$_3$, NCOCH$_3$ or NCH$_2$phenyl;
Y is selected from the group consisting of N and CH;
R$_5$ and R$_6$ are independently selected from the group consisting of H, F, CH$_3$, =O, phenyl, pyridyl, phenylCH$_2$, CH$_2$OH, CH$_3$CO and COOH;
R$_{11}$ is selected from the group consisting of H, CH$_3$, Et, i-Pr, phenylCH$_2$, CH$_3$CO, phenyl and phenyl(CH$_2$)$_2$;
or R$_5$ and R$_6$, R$_5$ and R$_{11}$ or R$_6$ and R$_{11}$ are linked together to form an unsubstituted or substituted 4- to 10-membered ring wherein the moiety:

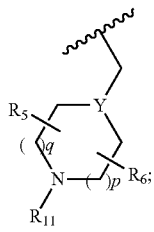

has a meaning selected from the group consisting of:

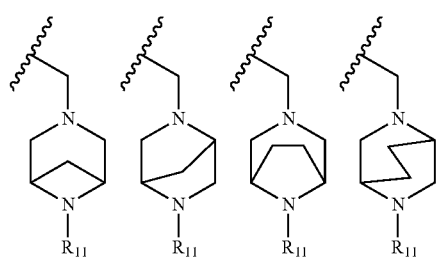

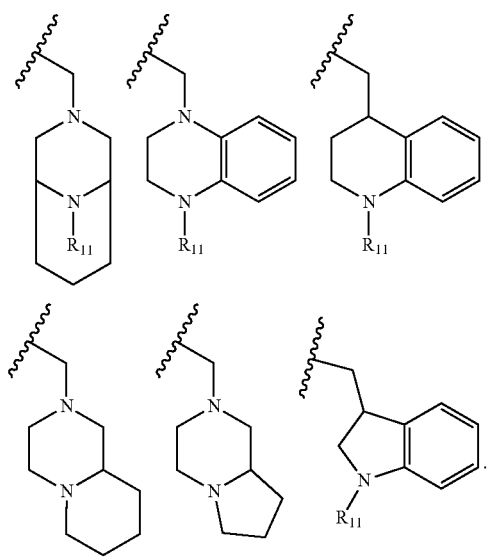

5. The compound according to claim 4 wherein R$_5$ and R$_6$, or R$_5$ and R$_{11}$ or R$_6$ and R$_{11}$ are linked together to form an unsubstituted or substituted 4- to 10-membered ring wherein the moiety:

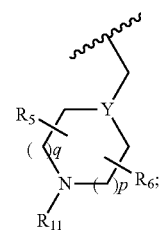

has a meaning selected from the group consisting of:

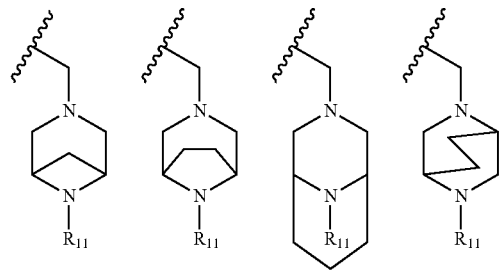

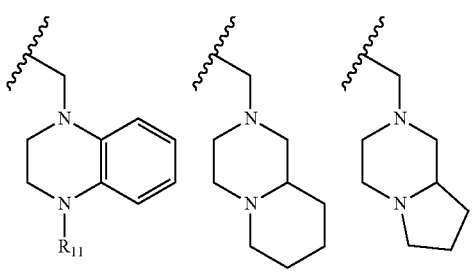

-continued

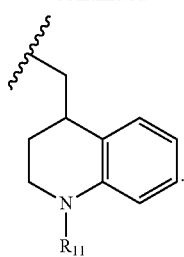

6. The compound according to claim 1, having the Formula (I''):

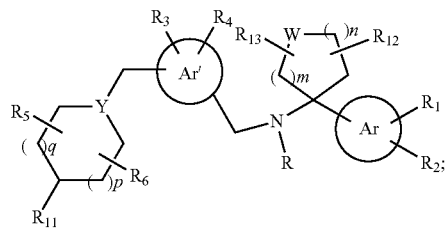

wherein Ar and Ar' are, independently, selected from benzene, pyridine, naphthalene and thiophene rings;

R is H and $CH_3$;

$R_1$ and $R_3$ are independently selected from the group consisting of H, F, $CH_3$, $OCH_3$, OH and $CF_3$;

$R_2$ and $R_4$ are both H;

p and q are equal to 1, m is an integer from 1 to 2, n is an integer from 1 to 2;

$R_{12}$ and $R_{13}$ are independently selected from the group consisting of H, F, $CH_3$, $CH_2OH$, =O and OH, or $R_{12}$ and $R_{13}$ are connected to the same carbon atom and have both the same meaning selected from F and $CH_3$;

W is a bond, O, NH, $NCH_3$, $NCOCH_3$ or $NCH_2phenyl$;

Y is N or CH;

$R_5$ and $R_6$ are independently selected from the group consisting of H, F, $CH_3$, =O, phenyl, pyridyl, phenyl$CH_2$, $CH_2OH$, $CH_3CO$ and COOH;

$R_{11}$ is selected from the group consisting of H, $CH_3$, Et, i-Pr, phenyl$CH_2$, $CH_3CO$ and phenyl;

or $R_5$ and $R_6$, $R_5$ and $R_{11}$ or $R_6$ and $R_{11}$ are linked together to form an unsubstituted or substituted 4- to 10-membered ring wherein the moiety:

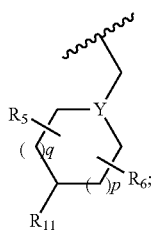

has a meaning selected from the group consisting of:

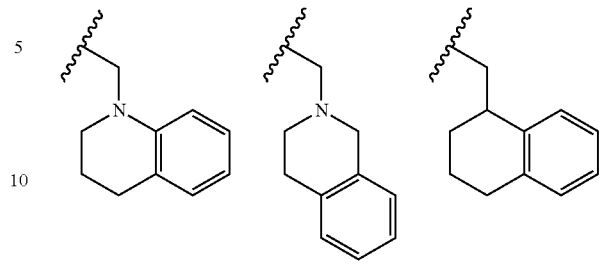

7. The compound according to claim 6 wherein Ar and Ar' are benzene rings.

8. The compound according to claim 6 wherein $R_5$ and $R_6$, or $R_5$ and $R_{11}$ or $R_6$ and $R_{11}$ are linked together to form an unsubstituted or substituted 4- to 10-membered ring wherein the moiety:

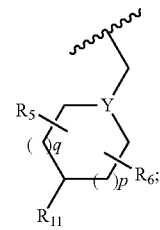

has a meaning selected from the group consisting of:

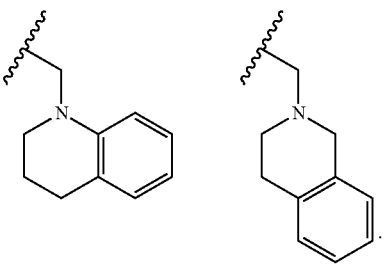 [SMILES: *CN1CCCc2ccccc21 ; *CN1CCc2ccccc2C1]

9. The compound according to claim 1, selected from the group consisting of:

4-[[[1-(2-fluorophenyl)cyclopentyl]amino]methyl]-2-(1-piperidylmethyl)phenol dihydrochloride;

4-[[[1-(2-fluorophenyl)cyclohexyl]amino]methyl]-2-[(4-methylpiperazin-1-yl)methyl]phenol trihydrochloride;

1-(2-fluorophenyl)-N-[[3-[(4-methylpiperazin-1-yl)methyl]phenyl]methyl]cyclopentanamine trihydrochloride;

1-(2-fluorophenyl)-N-[[4-methoxy-3-[(4-methylpiperazin-1-yl)methyl]phenyl]methyl]cyclopentanamine trihydrochloride;
4-[[[1-(2-fluorophenyl)cyclopentyl]-methyl-amino]methyl]-2-[(4-methylpiperazin-1-yl)methyl]phenol trihydrochloride;
2-[(4-methylpiperazin-1-yl)methyl]-4-[[(1-phenylcyclopentyl)amino]methyl]phenol trihydrochloride;
1-[4-[[5-[[[1-(2-fluorophenyl)cyclopentyl]amino]methyl]-2-hydroxyphenyl]methyl]piperazin-1-yl]ethanone dihydrochloride;
4-[[[1-(2-fluorophenyl)cyclopentyl]amino]methyl]-2-[(4-phenylpiperazin-1-yl)methyl]phenol trihydrochloride;
2-[(4-ethylpiperazin-1-yl)methyl]-4-[[[1-(2-fluorophenyl)cyclopentyl]amino]methyl]phenol trihydrochloride;
4-[[[1-(2-fluorophenyl)cyclopentyl]amino]methyl]-2-(piperazin-1-ylmethyl) phenol;
2-[(4-benzylpiperazin-1-yl)methyl]-4-[[[1-(2-fluorophenyl)cyclopentyl]amino]methyl]phenol trihydrochloride;
4-[[[1-(2-fluorophenyl)cyclopentyl]amino]methyl]-2-[(4-isopropylpiperazin-1-yl)methyl]phenol trihydrochloride;
4-[[[1-(2-fluorophenyl)tetrahydropyran-4-yl]amino]methyl]-2-[(4-methylpiperazin-1-yl)methyl]phenol trihydrochloride;
4-(2-fluorophenyl)-4-[[4-hydroxy-3-[(4-methylpiperazin-1-yl)methyl]phenyl]methylamino]cyclohexanone trihydrochloride;
4-[[[4,4-difluoro-1-(2-fluorophenyl)cyclohexyl]amino]methyl]-2-[(4-methyl-piperazin-1-yl)methyl]phenol trihydrochloride;
1-(2-fluorophenyl)-N-[[3-[(1-methyl-4-piperidyl)methyl]phenyl]methyl]cyclopentanamine dihydrochloride;
1-(2-fluorophenyl)-N-methyl-N-[[3-[(1-methyl-4-piperidyl)methyl]phenyl]methyl]cyclopentanamine dihydrochloride;
4-[[[1-benzyl-4-(2-fluorophenyl)-4-piperidyl]amino]methyl]-2-[(4-methylpiperazin-1-yl)methyl]phenol tetrahydrochloride;
4-[[[1-(2,4-difluorophenyl)cyclopentyl]amino]methyl]-2-[(4-methylpiperazin-1-yl)methyl]phenol trihydrochloride;
4-[[[1-(3-fluorophenyl)cyclopentyl]amino]methyl]-2-[(4-methylpiperazin-1-yl)methyl]phenol trihydrochloride;
4-[[[1-(4-fluorophenyl)cyclopentyl]amino]methyl]-2-[(4-methylpiperazin-1-yl)methyl]phenol trihydrochloride;
2-[(4-methylpiperazin-1-yl)methyl]-4-[[[1-(3-thienyl)cyclopentyl]amino]methyl]phenol trihydrochloride;
2-[[[1-(2-fluorophenyl)cyclohexyl]amino]methyl]-6-[(4-methylpiperazin-1-yl)methyl]phenol;
1-(2-fluorophenyl)-N-[[2-[(4-methylpiperazin-1-yl)methyl]-4-pyridyl]methyl]cyclohexanamine;
4-[[[1-(2-fluorophenyl)cyclohexyl]amino]methyl]-2-[(5-methyl-2,5-diazabicyclo[2.2.2]octan-2-yl)methyl]phenol;
4-[[[1-(2-fluorophenyl)cyclohexyl]amino]methyl]-2-[(4-methyl-2,3-dihydroquinoxalin-1-yl)methyl]phenol;
2-(1,3,4,6,7,8,9,9a-octahydropyrido[1,2-a]pyrazin-2-ylmethyl)-4-[[[1-(2-fluorophenyl)cyclohexyl]amino]methyl]phenol;
4-[[[1-(2-fluorophenyl)cyclohexyl]amino]methyl]-2-[(9-methyl-3,9-diazabicyclo[3.3.1]nonan-3-yl)methyl]phenol;
4-[[[1-(2-fluorophenyl)cyclohexyl]amino]methyl]-2-[(8-methyl-3,8-diazabicyclo[3.2.1]octan-3-yl)methyl]phenol;
4-[[[1-(3,5-difluorophenyl)cyclopentyl]amino]methyl]-2-[(4-methylpiperazin-1-yl)methyl]phenol;
4-[[[1-(3-fluoro-2-naphthyl)cyclohexyl]amino]methyl]-2-[(4-methylpiperazin-1-yl)methyl]phenol;
4-[[[1-(2-fluorophenyl)cyclohexyl]amino]methyl]-3-[(4-methylpiperazin-1-yl)methyl]phenol;
2-[[[1-(2-fluorophenyl)cyclohexyl]amino]methyl]-4-[(4-methylpiperazin-1-yl)methyl]phenol;
4-[[[1-(2-hydroxyphenyl)cyclohexyl]amino]methyl]-2-[(4-methylpiperazin-1-yl)methyl]phenol;
4-[[[1-(2-fluorophenyl)-4-methyl-cyclohexyl]amino]methyl]-2-[(4-methylpiperazin-1-yl)methyl]phenol;
4-[[[1-(2-fluorophenyl)-4-(hydroxymethyl)cyclohexyl]amino]methyl]-2-[(4-methylpiperazin-1-yl)methyl]phenol;
4-[[[1-(2-fluorophenyl)-4-hydroxy-cyclohexyl]amino]methyl]-2-[(4-methylpiperazin-1-yl)methyl]phenol;
1-(2-fluorophenyl)-N-[[3-[(1-phenethyl-4-piperidyl)methyl]phenyl]methyl]cyclohexanamine;
4-[[[1-(2-fluorophenyl)-4-hydroxy-4-methyl-cyclohexyl]amino]methyl]-2-[(4-methylpiperazin-1-yl)methyl]phenol;
4-[[[1-(2-fluorophenyl)-4,4-dimethyl-cyclohexyl]amino]methyl]-2-[(4-methylpiperazin-1-yl)methyl]phenol;
4-[[5-[[[1-(2-fluorophenyl)cyclohexyl]amino]methyl]-2-hydroxy-phenyl]methyl]-1-methyl-piperidine-2-carboxylic acid;
1-(2-fluorophenyl)-N-[[3-[(1-methyl-4-piperidyl)methyl]phenyl]methyl]cyclohexanamine;
1-(3-fluorophenyl)-N-[[3-[(1-methyl-4-piperidyl)methyl]phenyl]methyl]cyclopentanamine;
N-[[3-[(1-benzyl-4-piperidyl)methyl]phenyl]methyl]-1-(2-fluorophenyl)cyclohexanamine;
1-(2-fluorophenyl)-N-[[3-[(1-methyl-3,4-dihydro-2H-quinolin-4-yl)methyl]phenyl]methyl]cyclohexanamine;
N-[[3-(cyclohexylmethyl)phenyl]methyl]-1-(2-fluorophenyl)cyclohexanamine; and
1-(2-fluorophenyl)-N-[[3-[(4-methylcyclohexyl)methyl]phenyl]methyl]cyclohexanamine.

10. A pharmaceutical composition comprising a compound of Formula (I) or a pharmaceutically acceptable salt or solvate thereof:

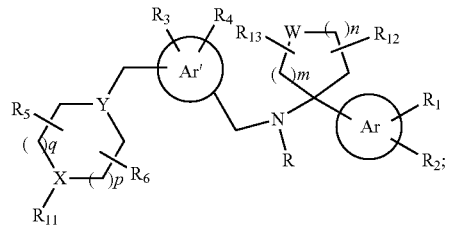

wherein Ar and Ar' are independently selected from the group consisting of a 5- to 10-membered aromatic or heteroaromatic single or fused rings comprising up to 3 heteroatoms selected from N, O and S;
R is selected from the group consisting of hydrogen, a linear or branched unsubstituted or substituted $C_{1-6}$ alkyl and an unsubstituted or substituted aryl $C_{1-6}$ alkyl;
$R_1$, $R_2$, $R_3$ and $R_4$ are independently selected from the group consisting of H, halogen, linear or branched, unsubstituted or substituted $C_{1-6}$ alkyl, $C_{1-6}$ alkoxy, hydroxy $C_{1-6}$alkyl, OH, CN, fluoro $C_{1-6}$ alkyl and fluoro $C_{1-6}$ alkoxy; $R_1$, $R_2$, $R_3$ and $R_4$ can be attached to any position of Ar and Ar' group, respectively;

Y is selected from the group consisting of N and CH;

X is selected from the group consisting of CH and N;

$R_5$ and $R_6$ are independently selected from the group consisting of H, halogen, unsubstituted or substituted linear or branched $C_{1-6}$ alkyl, =O, unsubstituted or substituted aryl, unsubstituted or substituted aryl $C_{1-6}$ alkyl, hydroxy $C_{1-6}$ alkyl, $C_{1-6}$ alkylCO, unsubstituted or substituted arylCO, unsubstituted or substituted aryl $C_{1-6}$ alkylCO, $COOR_7$, $CONR_8R_9$ and $SO_2R_{10}$ wherein $R_7$, $R_8$, $R_9$ and $R_{10}$ are independently selected from the group consisting of hydrogen and linear or branched $C_{1-6}$ alkyl; $R_5$ and $R_6$ can be attached to any carbon atom of the ring to which they are connected and they may be connected to the same carbon atom or to different carbon atoms of the ring; and $R_{11}$ is selected from the group consisting of H, linear or branched $C_{1-6}$ alkyl, $C_{1-6}$alkylCO, aryl and aryl $C_{1-6}$ alkyl;

or $R_5$ and $R_6$, or $R_5$ and $R_{11}$ or $R_6$ and $R_{11}$ are linked together to form an unsubstituted or substituted 4- to 10-membered ring, saturated or unsaturated, and containing up to two nitrogen atoms;

q and p are, independently, 0 or an integer from 1 to 2 with the proviso that when both Y and X are N, neither q and p are 0;

$R_{12}$ and $R_{13}$ are independently selected from the group consisting of H, F, $C_{1-6}$ alkyl, $C_{1-6}$ alkyl-OH, =O, OH, COOH, $CO_2Me$, $CONH_2$, CONHMe and $CONMe_2$ and can be attached to any position of the ring to which they are connected and they may be connected to the same carbon atom or to different carbon atoms of the ring;

W is selected from the group consisting of a bond and a heteroatom selected from the group consisting of O, S and $NR_{14}$, wherein $R_{14}$ is selected from the group consisting of H, linear or branched $C_{1-6}$ alkyl, $C_{1-6}$ alkylCO, unsubstituted or substituted aryl, unsubstituted or substituted aryl $C_{1-6}$ alkyl, unsubstituted or substituted arylCO, $SO_2R_{15}$, $CONR_{16}R_{17}$ and $COOR_{18}$, wherein $R_{15}$, $R_{16}$, $R_{17}$ and $R_{18}$ are independently selected from the group consisting of H and linear or branched $C_{1-6}$ alkyl;

m is an integer from 1 to 3, n is 0 or an integer from 1 to 3 with the proviso that when W is bond, n is not 0;

and a pharmaceutically acceptable carrier, stabilizer, diluent or excipient thereof.

11. A method of treating breast cancer associated with REV-ERBs activity in a mammal, wherein the method comprises administering to the mammal an effective amount of a compound of Formula (I) or a pharmaceutically acceptable salt or solvate thereof:

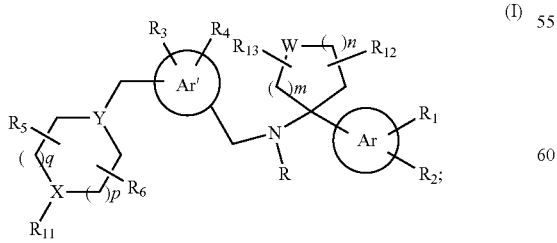

(I)

wherein Ar and Ar' are independently selected from the group consisting of a 5- to 10-membered aromatic and heteroaromatic single or fused rings comprising up to 3 heteroatoms selected from N, O and S;

R is selected from the group consisting of hydrogen, a linear or branched unsubstituted or substituted $C_{1-6}$ alkyl and an unsubstituted or substituted aryl $C_{1-6}$ alkyl;

$R_1$, $R_2$, $R_3$ and $R_4$ are independently selected from the group consisting of H, halogen, linear or branched, unsubstituted or substituted $C_{1-6}$ alkyl, $C_{1-6}$ alkoxy, hydroxy $C_{1-6}$ alkyl, OH, CN, fluoro $C_{1-6}$ alkyl and fluoro $C_{1-6}$ alkoxy; $R_1$, $R_2$, $R_3$ and $R_4$ can be attached to any position of Ar and Ar' group, respectively;

Y is selected from the group consisting of N and CH;

X is selected from the group consisting of CH and N;

$R_5$ and $R_6$ are independently selected from the group consisting of H, halogen, unsubstituted or substituted linear or branched $C_{1-6}$alkyl, =O, unsubstituted or substituted aryl, unsubstituted or substituted aryl $C_{1-6}$ alkyl, hydroxy $C_{1-6}$ alkyl, $C_{1-6}$ alkylCO, unsubstituted or substituted arylCO, unsubstituted or substituted aryl $C_{1-6}$ alkylCO, $COOR_7$, $CONR_8R_9$ and $SO_2R_{10}$ wherein $R_7$, $R_8$, $R_9$ and $R_{10}$ are independently selected from the group consisting of hydrogen and linear or branched $C_{1-6}$ alkyl; $R_5$ and $R_6$ can be attached to any carbon atom of the ring to which they are connected and they may be connected to the same carbon atom or to different carbon atoms of the ring; and $R_{11}$ is selected from the group consisting of —H, linear or branched $C_{1-6}$ alkyl, $C_{1-6}$ alkylCO, aryl and aryl $C_{1-6}$ alkyl;

or $R_5$ and $R_6$, or $R_5$ and $R_{11}$ or $R_6$ and $R_{11}$ are linked together to form an unsubstituted or substituted 4- to 10-membered ring, saturated or unsaturated, and containing up to two nitrogen atoms;

q and p are, independently, 0 or an integer from 1 to 2 with the proviso that when both Y and X are N, neither q and p are 0;

$R_{12}$ and $R_{13}$ are independently selected from the group consisting of H, F, $C_{1-6}$ alkyl, $C_{1-6}$ alkyl-OH, =O, OH, COOH, $CO_2Me$, $CONH_2$, CONHMe and $CONMe_2$ and can be attached to any position of the ring to which they are connected and they may be connected to the same carbon atom or to different carbon atoms of the ring;

W is selected from the group consisting of a bond and a heteroatom selected from the group consisting of O, S and $NR_{14}$, wherein $R_{14}$ is selected from the group consisting of H, linear or branched $C_{1-6}$ alkyl, $C_{1-6}$ alkylCO, unsubstituted or substituted aryl, unsubstituted or substituted aryl $C_{1-6}$ alkyl, unsubstituted or substituted arylCO, $SO_2R_{15}$, $CONR_{16}R_{17}$ and $COOR_{18}$, wherein $R_{15}$, $R_{16}$, $R_{17}$ and $R_{18}$ are independently selected from the group consisting of H and linear or branched $C_{1-6}$ alkyl;

m is an integer from 1 to 3, n is 0 or an integer from 1 to 3 with the proviso that when W is bond, n is not 0;

or a pharmaceutical composition according to claim 10.

* * * * *

UNITED STATES PATENT AND TRADEMARK OFFICE
CERTIFICATE OF CORRECTION

PATENT NO. : 9,611,245 B2
APPLICATION NO. : 15/027951
DATED : April 4, 2017
INVENTOR(S) : Benedetto Grimaldi et al.

Page 1 of 1

It is certified that error appears in the above-identified patent and that said Letters Patent is hereby corrected as shown below:

In the Claims

Claim 2, Column 97, Line 60:

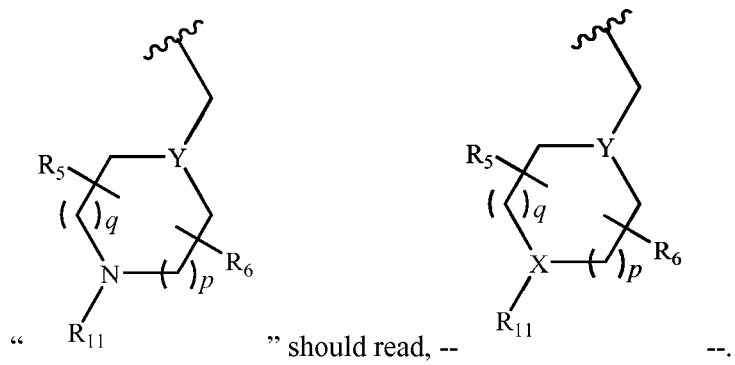

Claim 11, Column 106, Line 32:
"$R_{11}$ is selected from the group consisting of –H, linear or" should read, --$R_{11}$ is selected from the group consisting of H, linear or--.

Signed and Sealed this
Twentieth Day of March, 2018

Andrei Iancu
*Director of the United States Patent and Trademark Office*